United States Patent
Giroux et al.

(10) Patent No.: US 7,905,229 B2
(45) Date of Patent: Mar. 15, 2011

(54) AEROSOL GENERATING AND DELIVERY DEVICE

(75) Inventors: Marc Giroux, Lynnwood, WA (US); William A. DeGroodt, Mill Creek, WA (US); Joseph R. Pearce, Duvall, WA (US); Robert W. Kamp, North Bend, WA (US); Finn O. Rinne, Redmond, WA (US); Paul C. Leung, Seattle, WA (US)

(73) Assignee: Kurve Technology, Inc., Bothell, WA (US)

( * ) Notice: Subject to any disclaimer, the term of this patent is extended or adjusted under 35 U.S.C. 154(b) by 0 days.

(21) Appl. No.: 11/848,225

(22) Filed: Aug. 30, 2007

(65) Prior Publication Data

US 2008/0054099 A1    Mar. 6, 2008

Related U.S. Application Data

(60) Provisional application No. 60/824,017, filed on Aug. 30, 2006.

(51) Int. Cl.
*A61M 11/00* (2006.01)
*B05B 1/26* (2006.01)

(52) U.S. Cl. ............................. 128/200.21; 128/200.18

(58) Field of Classification Search ............ 128/200.14, 128/200.21, 200.18, 203.19, 204.24; 239/338, 239/340, 341, 346, 347, 369; 222/108, 109, 222/635

See application file for complete search history.

(56) References Cited

U.S. PATENT DOCUMENTS

| | | | |
|---|---|---|---|
| 2,819,716 A | | 1/1958 | Miller |
| 2,951,644 A | * | 9/1960 | Mahon et al. ............... 239/308 |
| 3,362,405 A | | 1/1968 | Hazel |
| 3,762,409 A | | 10/1973 | Lester |
| 3,836,079 A | * | 9/1974 | Huston ..................... 239/74 |
| 3,858,615 A | | 1/1975 | Weigl |

(Continued)

FOREIGN PATENT DOCUMENTS

EP    0539674    5/1993

(Continued)

OTHER PUBLICATIONS

Hess et al., "Medication Nebulizer Performance," Chest, 2006, pp. 498-505, vol. 110.

(Continued)

*Primary Examiner* — Tatyana Zalukaeva
*Assistant Examiner* — Kristen C Matter
(74) *Attorney, Agent, or Firm* — Barry L. Davison; Davis Wright Tremaine LLP

(57) ABSTRACT

Particular aspects provide novel atomizers for generating particles over a broad range of MMAD size distributions, the eliminating the requirement for an impaction baffle in generating the desired particle sizes. In particular aspects, the atomization means communicates with a remote particle filter member configured and positioned to provide for particle size filtering. In additional aspects, the atomization means communicates with a particle dispersion chamber suitable to impart a desired particle flow pattern to particles within and exiting the dispersion chamber. In further aspects, the atomization means communicates with a nasal, ocular, oral or 'vicinity' adapter. The novel devices provide for targeted (e.g., nasal, ocular, oral, local vicinity), systemic, and/or topical delivery of an atomized liquid (e.g., via the nasal cavity, olfactory region, and mouth). Further exemplary aspects relate to aerosolization and delivery of perfume, fragrance, essential oil or cosmeceutical agents and the like.

62 Claims, 22 Drawing Sheets

U.S. PATENT DOCUMENTS

| | | | |
|---|---|---|---|
| 4,052,985 A * | 10/1977 | Coleman et al. | 128/200.18 |
| 4,119,096 A | 10/1978 | Drews | |
| 4,150,071 A | 4/1979 | Pecina | |
| 4,198,969 A | 4/1980 | Virag | |
| 4,299,784 A | 11/1981 | Hense | |
| 4,454,880 A | 6/1984 | Muto | |
| 4,461,425 A | 7/1984 | Miller | |
| 4,702,415 A | 10/1987 | Hughes | |
| 4,809,692 A | 3/1989 | Nowacki | |
| 4,809,706 A | 3/1989 | Watson | |
| 4,865,027 A | 9/1989 | Laanen | |
| 4,938,209 A | 7/1990 | Fry | |
| 4,953,545 A | 9/1990 | McCarty | |
| 4,972,830 A | 11/1990 | Wong | |
| 5,063,922 A | 11/1991 | Häkkinen | |
| 5,201,726 A | 4/1993 | Kirkham | |
| 5,203,323 A | 4/1993 | Tritle | |
| 5,241,954 A | 9/1993 | Glenn | |
| 5,287,847 A | 2/1994 | Piper | |
| 5,301,663 A | 4/1994 | Small | |
| 5,309,900 A | 5/1994 | Knoch | |
| 5,388,574 A | 2/1995 | Ingebrethsen | |
| 5,392,767 A | 2/1995 | Bianco | |
| 5,427,089 A | 6/1995 | Kraemer | |
| 5,435,282 A | 7/1995 | Haber | |
| 5,437,267 A | 8/1995 | Weinstein | |
| 5,458,135 A | 10/1995 | Patton | |
| 5,476,093 A | 12/1995 | Lankinen | |
| 5,479,920 A | 1/1996 | Piper | |
| 5,485,828 A | 1/1996 | Hauser | |
| 5,487,378 A | 1/1996 | Robertson | |
| 5,490,630 A | 2/1996 | Hecker | |
| 5,497,765 A | 3/1996 | Praud | |
| 5,497,944 A | 3/1996 | Weston | |
| 5,505,193 A | 4/1996 | Ballini | |
| 5,520,167 A | 5/1996 | Hamilton | |
| 5,577,497 A | 11/1996 | Mecikalski | |
| 5,584,285 A | 12/1996 | Salter | |
| 5,586,551 A | 12/1996 | Hilliard | |
| 5,588,564 A | 12/1996 | Hutson | |
| 5,685,291 A | 11/1997 | Marsh | |
| 5,687,912 A | 11/1997 | Denyer | |
| 5,724,965 A | 3/1998 | Handke | |
| 5,743,250 A | 4/1998 | Gonda | |
| 5,755,218 A | 5/1998 | Johansson | |
| 5,775,320 A | 7/1998 | Patton | |
| 5,785,049 A | 7/1998 | Smith | |
| 5,855,202 A | 1/1999 | Andrade | |
| 5,875,774 A | 3/1999 | Clementi | |
| 5,906,198 A | 5/1999 | Flickinger | |
| 5,950,623 A | 9/1999 | Michell | |
| 5,954,049 A | 9/1999 | Foley | |
| 6,062,214 A | 5/2000 | Howlett | |
| 6,073,629 A | 6/2000 | Hardy | |
| 6,076,520 A | 6/2000 | Cooper | |
| 6,085,740 A | 7/2000 | Ivri | |
| 6,095,141 A | 8/2000 | Armer | |
| 6,112,746 A | 9/2000 | Kwok | |
| 6,119,694 A | 9/2000 | Correa | |
| 6,131,568 A * | 10/2000 | Denyer et al. | 128/200.21 |
| 6,158,428 A | 12/2000 | Mecikalski | |
| 6,192,876 B1 | 2/2001 | Denyer | |
| 6,202,643 B1 | 3/2001 | Sladek | |
| 6,223,744 B1 | 5/2001 | Garon | |
| 6,234,459 B1 | 5/2001 | Rock | |
| 6,240,917 B1 | 6/2001 | Andrade | |
| 6,244,573 B1 | 6/2001 | Rock | |
| 6,338,443 B1 | 1/2002 | Piper | |
| 6,347,629 B1 | 2/2002 | Braithwaite | |
| 6,367,471 B1 | 4/2002 | Genosar | |
| 6,394,085 B1 | 5/2002 | Hardy | |
| 6,412,488 B1 | 7/2002 | Barnett | |
| 6,418,925 B1 | 7/2002 | Genova | |
| 6,470,882 B1 | 10/2002 | Newhouse | |
| 6,550,472 B2 | 4/2003 | Litherland | |
| 6,576,224 B1 | 6/2003 | Osbakken | |
| 6,651,655 B1 | 11/2003 | Licalsi | |
| 6,702,997 B2 | 3/2004 | Chaudry | |
| 6,749,597 B2 | 6/2004 | Frank | |
| 6,796,513 B2 | 9/2004 | Fraccaroli | |
| 6,810,872 B1 | 11/2004 | Ohki | |
| RE38,700 E | 2/2005 | Briggs | |
| 6,851,626 B2 | 2/2005 | Patel | |
| 6,883,517 B2 | 4/2005 | Halamish | |
| 6,948,491 B2 | 9/2005 | Loeffler | |
| 6,994,083 B2 | 2/2006 | Foley | |
| 2002/0124843 A1 | 9/2002 | Skiba | |
| 2003/0078551 A1 | 4/2003 | Hochrainer | |
| 2004/0025871 A1 | 2/2004 | Davies | |
| 2004/0164099 A1 | 8/2004 | Diestelhorst | |

FOREIGN PATENT DOCUMENTS

| | | |
|---|---|---|
| EP | 0734719 | 10/1996 |
| EP | 0747078 | 12/1996 |
| GB | 1069048 | 5/1967 |
| JP | 8280809 | 10/1996 |
| WO | WO 98/26827 | 6/1998 |
| WO | WO 99/47273 | 9/1999 |
| WO | WO 01/02024 | 1/2001 |
| WO | WO 01/36033 | 5/2001 |
| WO | WO 01/49350 | 7/2001 |
| WO | WO 03/026559 | 4/2003 |
| WO | WO 2005/023335 | 3/2005 |

OTHER PUBLICATIONS

Hess, "Nebulizers: Principles and Performance," Respiratory Care, 2000, pp. 609-622, vol. 45.

Loffert et al., "A Comparison of Commercial Jet Nebulizers," Chest, 1994, pp. 1788-1792, vol. 106.

O'Callaghan et al., "The science of nebulised drug delivery," Thorax, 1997, pp. S31-S44, vol. 52, Supplement 2.

Zhao et al., "Effect of Anatomy of Human Nasal Air flow and Odorant Transport Patterns: Implications for Olfaction," Chemical Senses, 2004, pp. 365-379, vol. 29.

* cited by examiner

AEROSOL GENERATING AND DELIVERY DEVICE

CROSS-REFERENCE TO RELATED APPLICATIONS

This application claims the benefit of priority to U.S. Provisional Patent Application Ser. No. 60/824,017, filed 30 Aug. 2006, which is incorporated by reference herein in its entirety.

FIELD OF THE INVENTION

Particular exemplary aspects relate generally to aerosolized particle generation and delivery of same to a user, and more particularly to novel devices and apparatus for atomized particle generation, and to novel integrated particle generation, dispersion and delivery devices suitable for targeted delivery to a user including, but not limited to the nasal cavity or regions thereof of a user, the inside of the mouth of a user, the skin of the user, the surface of the eye of a user, and the vicinity of a user. Additional exemplary aspects relate to novel methods for administration of therapeutic agents to the nasal cavity, deep nasal cavity and paranasal sinuses of a user (e.g., a patient) using the novel devices, and to ocular and oral delivery using the novel devices. Further exemplary aspects relate to aerosolization and delivery of perfume, fragrance, essential oil or cosmeceutical agents and the like.

BACKGROUND

In the United States, sixty million people suffer from chronic sinusitis and allergic rhinitis and are treated by means of topically applied antihistamines, antibiotics, decongestants, and pain relievers. Many of these drugs would work more effectively in relieving symptoms if they could be applied directly to all of the affected areas. However, the devices utilized thus far to deliver these drugs have proven to be extremely inadequate, if not useless, in reaching all areas needed especially the deep nasal cavity, olfactory region, and paranasal sinuses critical to the treatment of some of these diseases and conditions. In addition to topically applied drugs (e.g., such as particular drugs in the categories listed above), there are a wide variety of systemically-absorbed drugs that are delivered intranasally. Moreover, a completely new field of nose to brain drug delivery is emerging. Current devices utilized for such systemically-absorbed drugs have also proven to be inadequate for many applications.

Current delivery systems comprise, for example, metered dose spray bottles and pneumatic (e.g., compressed air) atomizers that eject the medicine into the nostrils in large particles, or streams of atomized liquid. While a substantial mass of aerosolized particles can be quickly ejected or projected from such devices, the ejected or projected particles are relatively large, such that the efficacy of medicine administered in this manner is limited because of variable user skill and inadequate delivery and/or target distribution. For example, because of the relatively large particle sizes and the velocity vectors and characteristics of the particles, medicines delivered in this manner reach very little of the nasal mucosa and essentially no part of paranasal sinuses. Instead, such devices spray the particles into, for example, the anterior nasal cavity where the substantial mass of the particles impact the surfaces and drip out the nostril, or quickly clear along the floor of the nasal cavity. In cases of severe congestion or nasal polyps, the medicine often does not proceed beyond the nostril and has no chance of being effectively absorbed into the bloodstream in the necessary area of the nasal cavity. Therefore, while current prior art metered dose spray bottles and pneumatic atomization systems allow for rapid mass delivery, they are typically of relatively crude simplistic design, and substantially waste medicament because they do not provide adequate particle size distributions or delivery targeting for many purposes (e.g., they do not allow for particles to penetrate or reach high into the nasal cavity, and be retained therein, as required for systemic nose to brain delivery, or for paranasal sinus delivery.

As an improvement, pneumatic (e.g., compressed air) nebulizers have been developed and are familiar in the art. Fundamentally, nebulizers are distinguished from simple atomizers by the presence in the former of an 'impaction or stagnation baffle' placed, adjacent the compressed gas orifice, in the aerosol stream. Typically, for pneumatic nebulizers, compressed gas is delivered through a compressed air channel and orifice (et) of a compound integrated aerosolization nozzle causing a region of negative pressure (Venturi effect) in close proximity to a restricted liquid/solution channel or capillary. The liquid to be aerosolized is entrained, by virtue of its proximity to the restricted liquid channel within the nozzle configuration, into the jet orifice gas stream and is sheared into a liquid film or ligaments that may collapse into initial droplets under the influence of surface tension. While a small proportion of the initial droplets are smaller (e.g., 5 µm or less), the predominant portion of such initial droplets and/or film/ligaments are substantially larger and are subsequently violently shattered upon impaction with the closely spaced impaction/stagnation baffle, which serves to provide for production of smaller droplets and for return of larger droplets to the liquid reservoir. For efficacy in optimizing smaller particle production, the impaction/stagnation baffle is placed extremely close to the compressed air orifice, typically within a fraction of a millimeter from the jet or nozzle orifice. Because of the close spacing, the impaction/stagnation baffle also serves to redirect compressed gas flow laterally toward the walls of the atomization chamber, and smaller particles (e.g., 5 µm or less, corresponding to both shattered and initially atomized small unshattered particles) are thereby carried laterally toward the walls of the nebulization chamber. While most of such laterally directed particles are thereafter collisionally 'consumed' by walls/surfaces of the atomization chamber, a small proportion of such laterally-directed particles are again redirected toward the user by the user's inhalation stream and are thereby rendered deliverable to the user (e.g., deliverable as a mist or vapor of very tiny particles to the lungs by means of a user breathing the medicine-containing particles from a pipe attachment or, in the case of young children, a face mask, e.g., inhalation of nebulized particles during an asthma attack).

Therefore, prior art closely spaced impaction/stagnation baffles provide two functions: (i) shattering of larger particles into smaller particles; and (ii) laterally redirecting smaller particles. However, in either instance, the deliverable particles do not have, upon generation, a velocity vector path in the direction of the user that is not obstructed by the impaction/stagnation baffle, and the particle velocity vectors are such that the particles thus either impact on the baffle, laterally impact on the atomization chamber wall/surfaces, or are laterally directed and subsequently directed toward the user. Significantly, therefore, with prior art nebulizers, there are no particles that have, as initially generated, velocity vectors with paths toward the user that are not obstructed by the impaction/stagnation baffle, and delivery of such particles is thus entirely dependent upon redirecting particles around the baffle by inhalation facilitated flow redirection. Significantly therefore, not only is the size range of deliverable particles limited by such designs (e.g., to those small enough to be laterally directed and redirected toward the user (e.g., 5 μm or less) by the inhalation stream, but the delivery efficiency is limited because of the small percentage of particles that avoid being 'consumed' on the baffle, and on the walls and surfaces of the atomization chamber because of the indirect paths that the deliverable particles must take. This is a significant limitation of prior art devices.

Fundamentally, with prior art pneumatic nebulizers, while the impaction/stagnation baffle serves to redirect the compressed air flow direction (typically at right angles to the longitudinal jet axis) and return larger droplets to the liquid reservoir for re-entrainment, the creation and size of the generated deliverable particles are entirely determined by violent impaction with the baffle subsequent to entrainment of the solution by the compressed air jet of the nozzle, and those shattered particles that don't then impact the side-walls are drawn to the user during user inhalation. Droplet size is typically reported as mean mass aerodynamic diameter (MMAD), which is the diameter around which the mass of the aerosol is equally divided; that is, the calculated aerodynamic diameter that divides the particles of an aerosol (a gaseous suspension of fine liquid or solid particles) in half, based on the mass of the particles (by mass, 50% of the particles will be larger than the MMAD and 50% of the particles will be smaller than the MMAD). Therefore MMAD is used to characterize a population of droplets produced, and does not refer to the size of individual droplets. The particle size distribution of any aerosol may thus be statistically described by the median aerodynamic diameter along with the geometric standard deviation (GSD) based on the weight and size of the particles. Significantly, it should be appreciated, that because the volume (and hence the mass) of the droplet is determined by the cube of the radius ($v=4/3\,\pi r^3$), most of the particles will be smaller than the MMAD. The respirable dose is sometimes reported as the respirable mass, which is the output of droplets from the nebulizer in, for example, a respirable range of 1-5 um. Therefore, with prior art pneumatic nebulizers, the size and output of droplets comprising the respirable mass is entirely determined by the impaction and shattering function of the closely opposed impaction/stagnation baffle, and where a small but deliverable proportion of the laterally-directed particles avoid impacting the side-walls of the atomization chamber and are rather carried to the user in the user's inhalation stream.

Typically, a device selected for administration of pharmacologically active aerosol to the lung parenchyma should produce particle sizes with a mass median aerodynamic diameter (MMAD) of 1-3 microns. For airway deposition MMAD should be around 2-5 microns. Relatively small particle size is important for lung delivery in that, for example, it allows passage of the drug through heavily congested airways over a sufficient period (e.g., of about 10 minutes), to allow for deep lung penetration. Such nebulizers are used, for example, by asthmatics in response to an asthma attack.

With reference to FIG. 1, such prior art pneumatic nebulizers generally have, in addition to a closely opposed impaction element/baffle, a compound integrated aerosol nozzle comprising a compressed air or fluid channel with an end orifice, along with an integrated solution channel in communication with a liquid or solution (e.g., medicine solution). Moreover, such nebulizers generally correspond to one of two types; namely an 'internal mixing' (FIG. 1A) design or an 'external mixing' (FIG. 1B) design (see, e.g., Hess, D. R., *Respiratory Care,* 435:609-622, 2000 for a discussion of nebulizer designs incorporated herein by reference). Generally speaking, with internal mixing designs, gas flow interacts with the solution prior to leaving the nozzle exit orifice. For example, in FIG. 1A, the nozzle is concentrically mounted around a compressed gas delivery tube/channel (with end orifice) such that between the tube and nozzle there is a narrow interspace channel in communication with a liquid/solution reservoir. The exit of compressed gas from the gas delivery tube orifice causes solution to be drawn up through the restricted interspace to form an ascending stream of air and solution which leaves from the nozzle orifice and strikes the baffle to cause atomization of the particles (see also FIG. 1 of U.S. Pat. No. 6,796,513). By contrast, with external mixing, jet gas and the solution interact after both leave the nozzle. For example, in FIG. 1B, the nozzle orifice is a compound orifice, comprising a gas delivery tube/channel (with end orifice) that is coplanar with respect to a concentric solution channel orifice. In such designs fluid must leave the solution channel orifice (and the nozzle) before it can interact with the jet gas. The exit of compressed gas from the gas delivery tube orifice (and thus from the nozzle) causes solution to be drawn from the narrow solution channel and orifice (and thus from the nozzle) where it subsequently interacts with the jet gas to form a stream of air and solution which strikes the baffle to cause atomization of the particles. Different jet nebulizers have different output characteristics determined by the design of the air jet and capillary tube orifices, their geometric relationship with each other and with the closely opposed impaction baffles. In such prior art configurations, the major output determinant is generally the level/strength of the driving gas flow. So-called open 'vented' versions of these nebulizer designs allow for intake of ambient air during user inhalation to increase particle flow to the user and thus increase, at least to some extent, the effective nebulizer output at least during the inhalation phase.

Unfortunately, conventional jet nebulizers, including open vented versions, are highly inefficient because much of the aerosol is wasted during exhalation or excessively recycled within the nebulizer. In particular nebulizer designs, some aerosol waste is prevented by having one-way valves near the mouthpiece that redirect exhalation so that is does not substantially exhaust through the open inhalation vent in the primary aerosol generation chamber. However, even in these designs, between 93 and 99% of the primary droplets are caught on the internal baffles and structures and typically returned to the solution reservoir for re-entrainment, resulting in low output and/or protracted nebulization times. Additionally, in view of the pervasive use of restricted or narrow liquid feed channels to the medicament reservoirs means, while prior art atomizers and nebulizers are adequate for generating particles from low viscosity solutions (e.g., up to 5 centipoise), they are incapable of delivery of more viscous solutions (e.g., 5-105 centipoise). Thus, most such currently used nebulizers are not sufficiently effective at delivering enough medicament formulation (especially viscous drug solutions) in a practical or reasonable time-period because of restrictive liquid feed channels and the requirement for impaction/stagnation baffle configurations to shatter and size the particles. Additionally, even if more powerful compressor means were to be employed in such designs, there would be attendant increases in device size, weight and expense, and also (at least in particular designs) an increase the aerosol waste during exhalation phases. Moreover, increased compressed air flow would not eliminate the excessive 93 to 99% recycling of impacted medicine droplets returned to the solution reservoir from the impaction baffles. Additionally, even if there was an amount and/or quality of output sufficient for particle delivery to the lungs, absent an appropriate particle generation and dispersion means (as taught herein below by applicants), such prior art nebulizers are not effective for nasal delivery of drugs (e.g., antibiotics, etc.), because the generated particles are (i) not appropriately sized or dispersed to effectively penetrate into the nasal cavity and/or paranasal sinuses, and (ii) not delivered in a direct flow path to enable efficient delivery of sufficient quantities of medicament in a practical time-frame.

There is, therefore, a pronounced need in the art for delivery methods and devices that enable more efficient output and delivery of aerosolized particles. There is a pronounced need for devices that reduce or eliminate the dependence on baffle impaction and flow redirectioning for generation and determination of particle size, not only to reduce the extent/amount of recycling and re-entrainment of baffle-impacted solution droplets to allow for shorter, more user-friendly delivery periods, but also to provide for generation of a broader range of particle sizes to enhance dynamic output.

There is a pronounced need in the art for more effective methods and devices for delivery of aerosolized medicaments of higher viscosity.

There is a pronounced need in the art for more effective methods and devices for delivery of medicament to treat patients for certain conditions without taking the medicament orally or through the lungs. There is a pronounced need for more effective and efficient delivery to all areas of the nasal cavity and paranasal sinuses, and for more strategic or targeted delivery of medicament to specific regions of the nasal cavity, nasal olfactory region and paranasal sinuses. There is a pronounced need in the art for more effective methods and devices to effectively administer therapeutic agents systemically via the nasal passages, through the various channels from the olfactory region to the brain and the deep paranasal sinuses. There is a pronounced need for more effective methods and devices to for delivery of drugs to the brain to treat conditions of the central nervous system (CNS); that is, for 'Nose-to-Brain' delivery (e.g., to bypass the so-called blood brain barrier). There is a pronounced need for ocular and oral delivery using more efficient devices, and more efficient means for aerosolization and delivery of perfume, fragrance, essential oil or cosmeceutical agents and the like to the vicinity or surfaces or users or targets.

SUMMARY OF THE INVENTION

Particular aspects generally provide novel particle generating devices, and in more particular aspects, novel, more efficient atomization devices that are capable of atomizing and effectively delivering liquids, and particularly those having increased viscosity relative to those liquids usable with prior art nebulization and atomization devices.

Additional aspects provide particle generation and delivery devices comprising the novel particle generating apparatus in combination with a conduit for delivering of the airborne (e.g., atomized) particles. Preferably, the inventive particle generation and delivery devices are for delivery of appropriately sized aerosolized particles to a user, and preferably delivery is to the nasal cavity, or region thereof, of the user by means of a nasal adapter, or for oral or ocular delivery.

Additional aspects provide novel integrated devices and apparatus comprising novel particle generation means (e.g., atomization), particle dispersion chamber, and adapter means for targeted delivery of aerosolized dispersed particles to a user, and preferably to the nasal cavity or regions thereof of the user. Preferably, the integrated devices are suitable for the targeted administration of therapeutic agents to the nasal cavity and paranasal sinuses of a patient. In preferred embodiments, such integrated devices comprise, in addition to particle generation and dispersion means, an aerodynamic 'particle size filter' or 'splitter' and a nasal, oral or ocular adapter.

According to preferred aspects, particle size, velocity characteristics and nostril entry location determine whether a majority of a medicament will reach a productive target area (e.g., deep nasal cavities, olfactory region, paranasal sinuses, etc.), or unproductively impact and deposit in the nasal aperture to drip back down the nose with minimal productive delivery and deposition in the nasal cavity.

Particular aspects provide an aerosol generating device comprising: an upright liquid feed tube having a liquid exit orifice and a sidewall; and an upright compressed fluid feed channel having a compressed fluid exit orifice, the compressed fluid exit orifice being spaced from a portion of the sidewall, the compressed fluid exit orifice being configured to direct a stream of compressed fluid toward the portion of the sidewall, the portion of the sidewall being configured to disrupt a portion of the stream of compressed fluid, the disrupted portion of the stream of compressed fluid being configured to atomize a liquid from the liquid exit orifice. In certain aspects, the atomized liquid comprises particles, and the device further comprises a filtering member configured aerodynamically to filter particles from the atomized liquid having a size greater than a predetermined maximum size. Particular embodiments further comprise a particle dispersion chamber configured to receive the atomized liquid and impart a predetermined flow pattern thereto. In certain aspects, the predetermined flow pattern is vortical. In certain embodiments, the upright liquid feed tube comprises a liquid supply member comprising a liquid feed channel, the feed channel having an inlet, a liquid supply member exit orifice, and a supply member end-wall face having an outside diameter disposed about the liquid supply member exit orifice, the liquid supply member feed channel defining a projected axis L, wherein the end wall face liquid feed channel exit orifice is separated by a distance of at least H from the compressed fluid channel exit orifice, H being measured along a projected axis F that is normal to a plane P defined by the compressed fluid channel exit orifice, H is equal to or greater than ¼, ½ or 1× the inner diameter D1 of the compressed fluid channel adjacent the compressed fluid channel exit orifice, the projected longitudinal axis L intersects the projected axis F at a right, acute or obtuse angle, defining an intersection plane I, and wherein at the distance H along projected axis F, the plane I-intersecting portion of the perimeter of the end-wall face is positioned at a distance S in a normal direction from the projected axis F, S being equal to or less than 2× the inner diameter D1 of the primary compressed fluid channel. In certain aspects, the liquid comprises at least one selected from the group consisting of medicaments, small or large molecule pharmaceutical agents, liquids, solutions, suspensions, emulsions, perfumes, fragrances, essential oils, cosmeceutical agents, oils, cosmeceutical agents, moisturizing agents, water, lotions, air fresheners, deionizing agents, aromatherapeutic agents, beverages, and skin treatments. In particular embodiments, the device further comprises a nasal, ocular, oral or 'vicinity' adapter in communication with the atomization means.

Additional embodiments provide an aerosol generating device comprising: a reservoir configured to hold a liquid; a liquid supply member comprising a diverting portion and a feed channel, the feed channel having an inlet in communication with the reservoir and an liquid supply member exit orifice, the feed channel being configured to draw liquid from the reservoir and transport it to the exit aperture for aerosolization therefrom by a compressed fluid; and a compressed fluid supply member comprising a compressed fluid channel having an exit orifice, the diverting portion being located between the exit orifice of the feed channel and the exit orifice of the compressed fluid channel, the compressed fluid channel being configured to receive a compressed fluid and conduct a portion of the compressed fluid through the exit orifice and into engagement with the diverting portion of the liquid supply member, the portion of the compressed fluid engaging the diverting portion being diverted by the diverting portion before aerosolizing the liquid from the exit aperture of the feed channel. In certain aspects, the compressed fluid channel and the diverting portion are configured such that a second portion of the compressed fluid conducted through the compressed fluid exit orifice does not engage the diverting portion of the liquid supply member. In particular embodiments, the diverting portion has a surface, the portion of the compressed fluid engaging the diverting portion engages the surface of the diverting portion, and the surface is configured to divert the portion of the compressed fluid engaging it non-uniformly. In certain aspects, the liquid supply member comprises a tube section, the feed channel comprises a first portion disposed inside the tube section, the exit aperture of the feed channel is formed in the tube section, and the tube section comprises an outside surface, and the diverting portion comprises a portion of the outside surface of the tube section located between the exit orifice of the feed channel and the exit orifice of the compressed fluid channel. In some embodiments, the portion of the compressed fluid conducted through the compressed fluid exit orifice exits the orifice along an axis "F," the liquid feed channel has a longitudinal axis "L," and the axis "F" intersects the axis "L." In particular aspects, the liquid supply member comprises an anchor portion and a free end portion, the anchor portion is located between the inlet of the liquid supply member and the exit orifice of the liquid supply member, the anchor portion is coupled to the compressed fluid supply member; and the free end portion comprises the inlet of the liquid supply member and is supported by the anchor portion within the reservoir. In some embodiments, the device further comprises a particle dispersion chamber configured to impart a flow pattern to the aerosolized liquid. Particular embodiments comprise a supply member end-wall face having an outside diameter disposed about the liquid supply member orifice, wherein the liquid supply member feed channel defines a projected axis L, the end wall face and the orifice are separated by a distance of at least H from compressed fluid channel exit orifice, H being measured along a projected axis F that is normal to a plane P defined by the compressed fluid channel exit orifice, H is equal to or greater than ¼, ½ or 1× the inner diameter D2 of the compressed fluid channel adjacent the compressed fluid channel exit orifice, the projected longitudinal axis L intersects the projected axis F at a right, acute or obtuse angle, defining an intersection plane I, and wherein at the distance H along projected axis F, the plane I-intersecting portion of the perimeter of the end-wall face is positioned at a distance S in a normal direction from the projected axis F, S being equal to or less than 2× the inner diameter D1 of the primary compressed fluid channel. In certain aspects, the liquid for which the reservoir is configured to hold comprises at least one selected from the group consisting of medicaments, small or large molecule pharmaceutical agents, liquids, solutions, suspensions, emulsions, perfumes, fragrances, essential oils, cosmeceutical agents, oils, cosmeceutical agents, moisturizing agents, water, lotions, air fresheners, deionizing agents, aromatherapeutic agents, beverages, and skin treatments. Certain embodiments further comprise a nasal, ocular, oral or 'vicinity' adapter in communication with the atomization means.

Yet additional embodiments provide an aerosol generating device comprising: a reservoir configured to hold a liquid; a liquid supply member comprising a feed channel comprising: a first portion with a first diameter and an exit orifice, and a second portion with a second diameter and an inlet aperture in communication with the reservoir, the first portion diameter being smaller than the second portion diameter, the feed channel being configured to draw liquid from the reservoir into the inlet aperture of the second portion and transport it to the exit orifice of the first portion for aerosolization therefrom by a compressed fluid; and a compressed fluid supply member comprising a compressed fluid channel and compressed fluid channel exit orifice configured to direct a compressed fluid flow passed the exit orifice of the first portion of the feed channel thereby aerosolizing the liquid therefrom. In certain aspects, the liquid held in the reservoir has a surface, at least a portion of the liquid supply member is located inside the reservoir, a first section of the second portion is below the surface of the liquid, and a second section of the second portion is above the surface of the liquid. Particular embodiments comprise a supply member end-wall face having an outside diameter disposed about the liquid supply member orifice, wherein the liquid supply member feed channel first portion defines a projected axis L, the end wall face and the orifice are separated by a distance of at least H from compressed fluid channel exit orifice, H being measured along a projected axis F that is normal to a plane P defined by the compressed fluid channel exit orifice, H is equal to or greater than ¼, ½ or 1× the inner diameter D1 of the compressed fluid channel adjacent the compressed fluid channel exit orifice, the projected longitudinal axis L intersects the projected axis F at a right, acute or obtuse angle, defining an intersection plane I, and wherein at the distance H along projected axis F, the plane I-intersecting portion of the perimeter of the end-wall face is positioned at a distance S in a normal direction from the projected axis F, S being equal to or less than 2× the inner diameter D1 of the primary compressed fluid channel. In certain embodiments, the liquid for which the reservoir is configured to hold comprises at least one selected from the group consisting of medicaments, small or large molecule pharmaceutical agents, liquids, solutions, suspensions, perfume, fragrance, essential oil or cosmeceutical agents, oils, cosmeceutical agents, moisturizing agents, water, lotions, air fresheners, deionizing agents and skin surface treatments. Certain aspects further comprise a nasal, ocular, oral or 'vicinity' adapter.

Further embodiments provide an aerosolization device having an aerosolization assembly configured to produce a stream of aerosolized particles from a liquid stored in a reservoir, the device comprising: a filtering member spaced apart from the aerosolization assembly and located within the stream of aerosolized particles, the filtering member being configured aerodynamically to separate the aerosolized particles within the stream of aerosolized particles having a size greater than a predetermined size from the aerosolized particles within the stream of aerosolized particles having a size less than or equal to the predetermined size, to collect the aerosolized particles having a size greater than a predetermined size and return them to the reservoir, and to permit the aerosolized particles having a size less than or equal to the predetermined size to pass thereby. In certain embodiments, the filtering member is configured aerodynamically to avoid collisions with the aerosolized particles of the stream of aerosolized particles. In certain aspects, at least 20%, at least 30%, at least 40%, at least 50%, or at least 60% of the aerosolized particles within the stream of aerosolized particles pass by the filtering member without colliding therewith. Particular aspects further comprise a particle dispersion chamber configured to receive the particles that pass by the filter member and impart a predetermined flow pattern to the particles. In particular implementations, the aerosolization assembly comprises a liquid supply member comprising a liquid feed channel, the feed channel having an inlet in communication with the reservoir, an liquid supply member exit orifice, and a supply member end-wall face having an outside diameter disposed about the liquid supply member exit orifice, the liquid supply member feed channel defining a projected axis L, wherein the assembly further comprises a compressed fluid supply member comprising a compressed fluid channel having an exit orifice, wherein the end wall face and liquid feed channel exit orifice are separated by a distance of at least H from compressed fluid channel exit orifice, H being measured along a projected axis F that is normal to a plane P defined by the compressed fluid channel exit orifice, H is equal to or greater than $¼$, $½$ or $1×$ the inner diameter D1 of the compressed fluid channel adjacent the compressed fluid channel exit orifice, the projected longitudinal axis L intersects the projected axis F at a right, acute or obtuse angle, defining an intersection plane I, and wherein at the distance H along projected axis F, the plane I-intersecting portion of the perimeter of the end-wall face is positioned at a distance S in a normal direction from the projected axis F, S being equal to or less than $2×$ the inner diameter D1 of the primary compressed fluid channel. In certain aspects, the liquid for which the reservoir is configured to hold comprises at least one selected from the group consisting of medicaments, small or large molecule pharmaceutical agents, liquids, solutions, suspensions, emulsions, perfumes, fragrances, essential oils, cosmeceutical agents, oils, cosmeceutical agents, moisturizing agents, water, lotions, air fresheners, deionizing agents, aromatherapeutic agents, beverages, and skin treatments. Particular aspects further comprise a nasal, ocular, oral or 'vicinity' adapter in communication with the atomization means.

Particular aspects provide an aerosol generating and delivery device, comprising: a housing having a wall defining an atomization chamber in which a liquid or solution is atomizable, and having holding means suitable for holding a liquid or solution to be atomized; the device further comprising atomization means comprising a primary compressed fluid feed channel having a length and inner diameter, and a primary orifice at a first end thereof in fluid communication with the atomization chamber and defining a primary orifice plane "P", the channel at a second end in fluid communication with a compressed fluid source and defining a projectable compressed fluid feed channel axis "F", the atomization means further comprising a primary liquid feed channel having a length, inner diameter and channel wall, and at a first channel end having a channel end-wall face having an outside diameter disposed about a liquid feed channel orifice in fluid communication with the atomization chamber, the primary liquid feed channel at a second end in communication with the liquid holding means, the primary liquid feed channel defining a projectable longitudinal liquid feed channel axis "L", wherein the channel end wall face and the liquid feed channel orifice are separated by a distance of at least H from the primary orifice plane "P", H being measured along the projected axis "F" and H being equal to or greater than $¼$, $½$ or $1×$ of the inner diameter D1 of the primary compressed fluid feed channel, wherein the projected longitudinal axis "L" intersects the projected longitudinal axis "F" at an acute angle defining an intersection plane "I", and wherein at the distance "H" along projected longitudinal axis "F", the plane "I"-intersecting portion of the perimeter of the end-wall face is positioned at or within a selected normal distance S from the projected longitudinal axis "F", S being equal to or less than $2×$ the inner diameter D1 of the primary compressed fluid feed channel.

In additional aspects, the aerosol generating and delivery device further comprises an aerodynamic particle size filter member in fluid communication with the particle atomization means, the filter member having an aerodynamic surface contour and positioned at a distance "J" along the projected axis "F" from the primary orifice plane "P" to provide an aerodynamic fluid flow around the surface, wherein the distance "J" is greater than the distance "H".

In further aspects, the aerosol generating and delivery device further comprises a particle dispersion chamber having a chamber wall and having an input opening and an output opening with an internal channel therebetween, the input opening in fluid communication with the atomization chamber, the dispersion chamber having at least one directed fluid output operative to impart a fluid flow pattern (e.g., 'vortical' flow, turbulent flow or randomized flow) to aerosolized particles within and exiting the dispersion chamber output opening.

In particular embodiments, the at least one directed fluid output comprises an ambient air channel that at one end is in communication with ambient air, and having at the other end an ambient air channel orifice in communication with the internal channel. In additional embodiments, the aerosol generating and delivery device further comprises an outer housing having an outer housing wall defining a plenum space between the outer housing wall and the wall of the particle dispersion chamber, the outer housing wall comprising at least one opening (with optional one-way valve) in communication with ambient air, such that the ambient air channel and corresponding orifice communicate with the at least one opening by means of the plenum space.

In some embodiments, the at least one directed fluid output comprises a compressed fluid output channel that at one end is in communication with a source of compressed fluid, and having at the other end a compressed fluid outlet orifice in communication with the internal channel of the particle dispersion chamber.

In particular embodiments, the aerosol generating and delivery device comprises a plurality of directed fluid outputs, the plurality comprising at least one ambient air channel that at one end is in communication with ambient air, and having at the other end an ambient air channel orifice in communication with the internal channel of the particle dispersion chamber, the plurality further comprising at least one compressed fluid output channel that at one end is in communication with a source of compressed fluid, and having at the other end a compressed fluid outlet orifice in communication with the internal channel of the particle dispersion chamber.

In yet further embodiments, the aerosol generating and delivery device further comprises a nasal adapter, oral adapter, ocular adapter, or 'vicinity' or surface adapter (e.g., for aerosolized particle (e.g., perfume, fragrance, essential oil or cosmeceutical agent and the like) delivery to the vicinity of a user or a target surface). in fluid communication with the output opening of the particle dispersion chamber.

Preferred aspects provide novel atomizer embodiments, comprising: a nasal adapter; a particle dispersion chamber in communication with the nasal adapter, the dispersion chamber suitable to impart 'vortical' or other suitable velocity vector pattern of movement (e.g., turbulent, randomized, etc.) to particles within the internal channel of and exiting the dispersion chamber; an atomization chamber having a medicine chamber and a novel particle generating (e.g., atomization) means comprising a liquid feed tube and an air feed tube, the liquid feed tube in communication with the medicament in the medicine chamber, the air feed tube in communication with a source of compressed air (e.g., an air compressor), wherein the unique spatial relationship between output ends of the liquid and air feed tubes, and the aerodynamic particle size filter or 'splitter' element, provides a highly efficient and adjustable means to generate specific and suitable MMAD particle populations without use of a closely opposed impaction baffle and associated excessive medicament solution recycling and re-entrainment. According to preferred aspects, the configuration of the particle dispersion chamber further imparts suitable velocity vector patterns (e.g., vertical flow) to the optimally-sized particle populations for effective targeting of, for example, specific areas of the nasal cavity, olfactory region, and or paranasal sinuses via a nasal adapter.

In preferred aspects, the delivered atomized particles are comprised of particles substantially having a mean diameter of, for example, about 10 μm to about 30 μm. Preferably, the delivered particles are comprised of particles substantially having a mean diameter of about 10 μm to about 15 μm for targeting the olfactory region and the paranasal sinuses, and about 15 μm to about 30 μm for targeting the overall nasal cavity.

According to further aspects, at least one of particle size or delivery rate can be varied, and is determined by at least one variable selected from several factors (in addition to the pressure and/or volume of the compressed fluid flow) including: the internal diameter (e.g., "D1" and "D2") and length ("L1" and "L2") of the primary compressed fluid feed channel 13 and primary liquid feed channel 15, respectively; the outer diameter ("D3") of the primary liquid feed channel 15 at the orifice 17 end; the distance ("H") from the primary orifice plane "P" (defined by the primary compressed fluid channel orifice 7) to the plane-I-intersecting portion (as defined herein below) of the perimeter of the primary liquid feed channel end wall face 23; the angle ("A") of approach between the primary liquid feed channel axis "L" and the primary compressed fluid feed channel axis "F"; the selected distance "S" as defined herein below, the 'offset' distance "O" as defined herein; the internal diameter ("D4") and length ("L4") of the secondary liquid feed channel 5; the distance "J" (as defined herein below) between the primary orifice plane "P" and the aerodynamic particle size filter member 21, and the physical characteristics of the liquid, such as, surface tension, viscosity, density, etc. Additionally, the design and location of the particle size filtering member or 'splitter,' and the design (e.g., length, taper, etc) of the particle dispersion chamber contribute to the output particle size.

Yet further embodiments provide a particle filter assembly configured to be positioned within a stream of aerosolized particles comprising a first group of aerosolized particles having a size greater than a predetermined size and a second group having a size less than or equal to the predetermined size, the particle filter assembly comprising: a filtering member configured aerodynamically to collect the aerosolized particles of the first group and to avoid collisions with the aerosolized particles of the second group permitting the aerosolized particles of the second group to pass thereby; and a support member configured to support the filtering member within the stream of aerosolized particles and to conduct the aerosolized particles of the first group collected by the filtering member to a reservoir. In certain aspects, the support member is configured aerodynamically to avoid collisions with the aerosolized particles of the stream of aerosolized particles. In particular embodiments, the stream of aerosolized particles is produced inside an atomization chamber defined by at least one chamber wall and the support member comprises at least one support arm coupling the filtering member to the at least one chamber wall. In certain aspects, the stream of aerosolized particles is produced inside an atomization chamber and emanates therefrom and the support member positions the filtering member outside the atomization chamber within a portion of the stream outside the atomization chamber. In some implementations, the stream of aerosolized particles is produced inside an atomization chamber having an exit aperture through which the stream may exit the atomization chamber and the support member positions the filtering member within the exit aperture of the atomization chamber. In particular aspects, the stream of aerosolized particles emanate from an aerosolization assembly comprising a liquid supply member comprising a liquid feed channel, the feed channel having an inlet in communication with the reservoir, an liquid supply member exit orifice, and a supply member end-wall face having an outside diameter disposed about the liquid supply member exit orifice, the liquid supply member feed channel defining a projected axis L, wherein the assembly further comprises a compressed fluid supply member comprising a compressed fluid channel having an exit orifice, wherein the end wall face liquid feed channel exit orifice are separated by a distance of at least H from compressed fluid channel exit orifice, H being measured along a projected axis F that is normal to a plane P defined by the compressed fluid channel exit orifice, H is equal to or greater than ¼, ½ or 1× the inner diameter D1 of the compressed fluid channel adjacent the compressed fluid channel exit orifice, and Wherein the support member is configured to support the filtering member within the stream of aerosolized particles at a distance J from the compressed fluid channel exit orifice, J being measured along the projected axis F, and wherein the distance J is greater than the distance H.

Yet additional aspects provide a method of generating aerosol particles comprising: directing a stream of compressed fluid into an atomization chamber; placing a liquid feed member comprising a liquid in the stream of compressed fluid thereby disrupting a portion of the stream of compressed fluid; and using the disrupted portion of the stream of compressed fluid to atomize the liquid in the liquid feed member. Certain aspects comprise filtering particles larger than a predetermined size from the atomized liquid. Particular embodiments, further comprise imparting a predetermined particle flow pattern to the atomized liquid. In certain aspects, the liquid comprises at least one selected from the group consisting of medicaments, small or large molecule pharmaceutical agents, liquids, solutions, suspensions, emulsions, perfumes, fragrances, essential oils, cosmeceutical agents, oils, cosmeceutical agents, moisturizing agents, water, lotions, air fresheners, deionizing agents, aromatherapeutic agents, beverages, and skin treatments. Particular implementations, further comprise use of a nasal, ocular, oral or 'vicinity' adapter in communication with the atomization means. Certain aspects comprise imparting a predetermined particle flow pattern to the atomized liquid and directing the atomized liquid into at least one of a nostril of a user, both nostrils of a user, a mouth of a user, at least one of an eye of a user, and both eyes of a user. Particular aspects further comprise expelling the atomized liquid into the ambient air thereby creating a cloud of atomized liquid.

Yet further embodiments provide a method of nasal delivery of aerosolized particles, comprising: obtaining a subject inspiring through the nose; delivering, over a plurality of nasal inspirations, aerosolized particles of a liquid formulation into at least one nasal passage of the subject, wherein a volume in the range of 0.2 to 2.0 ml, 0.4 to 1.5 ml, 0.6 to 1.2 ml, 0.8 to 1.1 ml, or 0.9 to 1 ml is delivered, wherein the number of inspirations is from about 8 to about 16, and wherein at least about 30%, about 50%, about 60%, about 70%, about 80% about 90% or about 100% of the delivered volume is retained in the at least one nasal passage. In certain aspects, the average tidal volume ($V_t$) is about 0.7 ml/Kg. In particular implementations, a volume in the range of about 0.4 to 1.5 ml, 0.6 to 1.2 ml, 0.8 to 1.1 ml, or 0.9 to 1 ml is delivered.

In preferred aspects, the inventive integrated devices provide appropriately sized particle distributions having suitable dynamic outflow properties to target specific user areas, such as in the nasal cavity or regions thereof, such as the paranasal sinuses.

The foregoing aspects and many of the attendant advantages will become more readily appreciated as the same become better understood by reference to the following detailed description, when taken in conjunction with the accompanying drawings. The discussion below is descriptive, illustrative and exemplary and is not to be taken as limiting the invention.

BRIEF DESCRIPTION OF THE DRAWINGS

FIG. 1A illustrates a typical internal mixing design, whereas FIG. 1B illustrates a typical external mixing design (the designs are taken from Hess, D. R., *Respiratory Care,* 45(6):609-622, 2000).

DETAILED DESCRIPTION OF THE INVENTION

Figure 1:
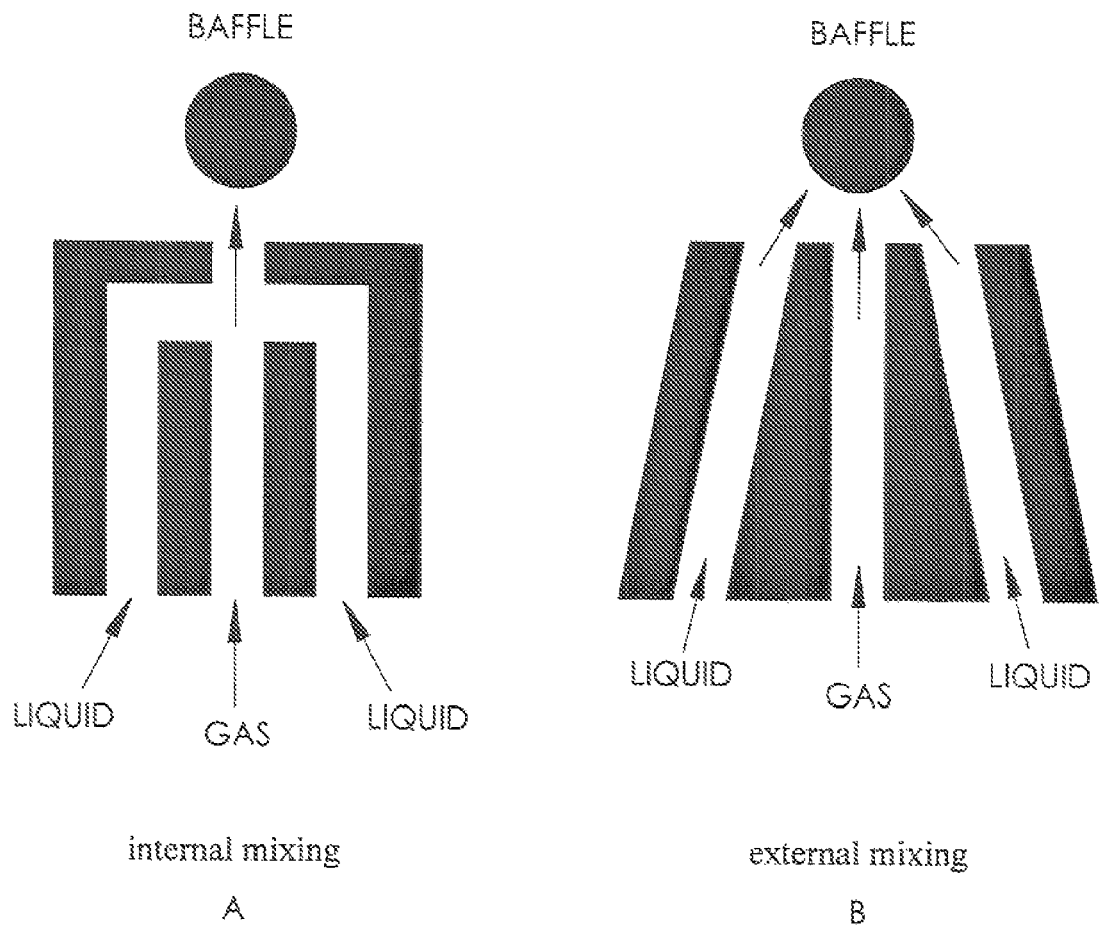
FIGS. 1A and 1B show the two dominant prior-art nebulizer designs.

Aspects of the present invention include aerosol generating and related delivery devices, such as atomizers and nebulizers. Further aspects include a filter member configured for use with such devices. Additional aspects include integrated atomizer and particle dispersion chamber apparatuses. The technology disclosed herein may have medical applications as well as non-medical applications. Further, various adapters may be used to configure the technology to deliver aerosolized particles to specific areas of the human body as well as to configure the technology for specific purposes (e.g., delivery of aerosolized particles to the vicinity of a user or to a target surface).

With respect to exemplary medical uses, prior art topical drug delivery methods are ineffective at penetrating very far into the nasal cavity and not at all into the paranasal sinuses. This is a significant limitation/problem, because systemic delivery via inhalation utilizing the nasal mucosa and mucosa in the paranasal sinuses is highly desirable for many targeted disease states.

Preferred aspects of the present invention provide novel atomizers, and novel integrated atomizers and particle dispersion chamber apparatuses that have the ability to deliver medicaments (e.g., such as the drugs presently prescribed for many diseases and conditions) as doses of very tiny medicine-containing particles over a broad particle range, and with medicament having significant viscosity. Inventive effective delivery is, for example, by using a nasal adapter that, in combination with the inventive particle generation and dispersion aspects, allows more efficacious topical and systemic targeted delivery within the nasal cavity and regions thereof of a user. Alternatively, effective inventive delivery may be by an ocular adaptor, oral adapter, vicinity adapter and the like.

Examples of diseases and/or conditions that can be treated by medicament delivery using the inventive apparatus and methods include, but are not limited to, endocrine and metabolic disorders, sinusitis, infection, migraines, sleep disorders, autoimmune diseases, osteoporosis, neurological diseases and disorders, obesity, sexual dysfunctions, diabetes, cardiovascular diseases and episodes, respiratory diseases, cystic fibrosis, cancer, ocular diseases and/or conditions including, but not limited to allergies, conjunctivitis, corneal infections, dry eye, Fuchs' Dystrophy, and others. Any of the aforementioned diseases and/or conditions that require systemic delivery of medications could also be treated through the mouth. The inventive devices can also be used for aerosolized antigen-mediated immunization, vaccination, etc.

According to preferred aspects, the particle size (e.g., MMAD particle distribution), particle dispersion technology (e.g., velocity vector pattern), and duration of application allow the medicine to reach and permeate the targeted area of the nasal cavity, and thus enable effective systemic delivery of medicament via the nasal cavity, eye, cheeks, and the like. For example, essentially any and all medicines currently applied (e.g., by direct action) to the nasal cavity and paranasal sinuses, including relatively viscous medicines and solutions, can be used or adapted (e.g., formulated) for use with the inventive atomizer and/or integrated atomizer embodiments, including but not limited to over-the-counter nasal medicines (e.g., for allergy and colds and flu) and prescription medicines.

Similarly, essentially any and all medicines currently applied (e.g., by direct action) to the surface of the eye, can be used or adapted (e.g., formulated) for use with the inventive atomizer and/or integrated atomizer embodiments, including but not limited to over-the-counter ocular medicines (e.g., for allergies and eye irritation) and prescription medicines. Further, essentially any and all medicines currently applied (e.g., by direct action) to the inside of the mouth (e.g., the inside of the cheeks), can be used or adapted (e.g., formulated) for use with the inventive atomizer and/or integrated atomizer embodiments, including but not limited to over-the-counter nasal or oral medicines (e.g., for allergies and sores) and prescription medicines. Additionally, medicines currently delivered/taken orally, by skin patch, or parenterally can be adapted (e.g., formulated) for delivery use using the inventive atomizer and integrated atomizer embodiments. In particular embodiments, the technology disclosed herein may be used to generate a cloud or fog of atomized particles or droplets that may be exposed to the skin. Following exposure, one or more liquids, such as a liquid solvent, included in the atomized particles or droplets may dry leaving materials (e.g., medicines, perfume, fragrance, essential oil or cosmeceutical agents, lotions, and the like) behind on the skin, which may remain on the surface of the skin or be absorbed thereby. Alternatively, the user's skin may absorb one or more of the liquids included in the atomized particles or droplets.

Among the many enabled utilities, the instant devices can be used for delivery of drugs to the brain to treat conditions of the central nervous system (CNS); so-called 'Nose-to-Brain' delivery. In this process, drugs delivered to the olfactory region of the nasal cavity (e.g., delivered very high through small passages) can enter the brain and bypass the so-called blood brain barrier. This inventive utility provides a very significant, here-to-fore unavailable method of drug delivery. Significantly, to achieve nose-to-brain delivery, the delivery device must be capable of efficiently providing a dynamic particle population suitable to target and reach this area. Significantly, according to preferred aspects, the inventive integrated atomizer has substantial utility for both topical and systemic delivery of drugs, therapeutics, and other beneficial compounds, and provides for nose-to-brain delivery of drugs, therapeutics and other beneficial compounds.

In particular aspects, and for a user with a secondary condition of nasal polyps, the inventive apparatus and methods allow far more effective application of medicine, which is otherwise blocked or precluded by such secondary conditions using contemporary systems. For example, prior art nasal inhalers and spray bottles are used to deliver corticosteroids, which, at least in theory, is designed to slow re-growth of polyps subsequent to polyp removal. Currently, however, such devices are largely ineffective at accomplishing this, often not slowing polyp growth at all. According to preferred aspects, the inventive apparatus and methods described herein provide for substantially improved and more effective slowing of such polyp re-growth.

According to additional aspects, many of the side effects of particular medicine delivery are precluded or eradicated by the inventive devices and methods. With many sprays, for example, the propellant causes a drying of the nasal passages leading to bleeds. Therefore, with such applications, a secondary spray of saline is added to the treatment in an attempt to control such bleeding. Additionally, for example, steroids in pill form have many unpleasant side effects such as internal bleeding, a redistribution of fluid to the head, neck and back causing unsightly "humps," and easy bruising, to name a few. An effective use of the inventive integrated atomizer for such steroid delivery does not have these attendant pill-based side effects.

Current nasal drug delivery devices deliver droplets in a range from 50 μm to 100 μm. Significantly, due to the size of the droplets and the physical characteristics of the nasal cavity, the maximum dose that can be delivered is 200 μl per nostril. This limitation on the deliverable amount of medicament volume (e.g., mass) restricts the formulation characteristics and limits additives that could assist in achieving the goals of the medication. By contrast, because of its unique and novel configuration, the inventive atomizer generates droplets that are much smaller, and substantially more suitable for deposition on a much larger surface area of the nasal cavity, particularly when an inventive integrated atomizer is used. The inventive atomizer, therefore, can deliver doses up to 2 ml to the nasal cavity, thus allowing for use of optimal/superior formulations and effectiveness.

The inventive devices could also be used to deliver aromatherapy. For example, the inventive apparatuses could be used to expel aerosolized particles into the air (e.g., in the vicinity of the user). These particles are then be perceived by the user located an appropriate distance from the device for an appropriate amount of time to receive a therapeutically significant quantity of aerosolized particles.

Non-medical uses include the aerosolization of perfume, fragrance, essential oil or cosmeceutical agents and the like. By way of example, the inventive apparatuses could be used to expel a cloud of aerosolized particles into the air through which the user to could pass his/her skin, clothes, and/or hair, thereby allowing a portion of the aerosolized particles to settle thereupon. Alternatively, the devices could be used to target surfaces with such aerosolized particles. Flavored particles could be delivered (e.g., to the tongue or nasal cavity, or to other surfaces). Adhesives could be delivered. Paints could be delivered.

Overview

Figure 2:
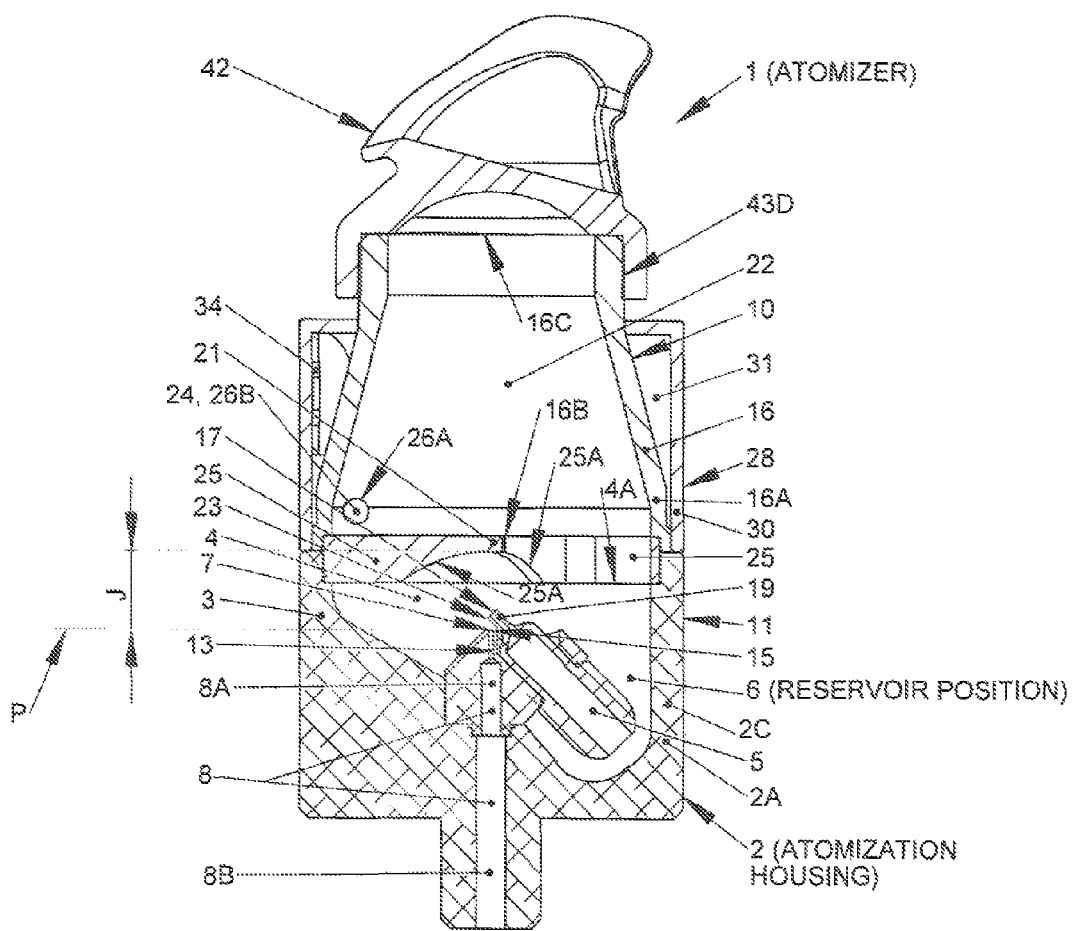
FIG. 2, shows, according to particular aspects of the present invention, a side cross-sectional view of an exemplary nasal atomizer embodiment, comprising: atomization means; aerodynamic particle size filtering means; particle dispersion chamber with plenum member; and nasal adapter.
Figure 3:
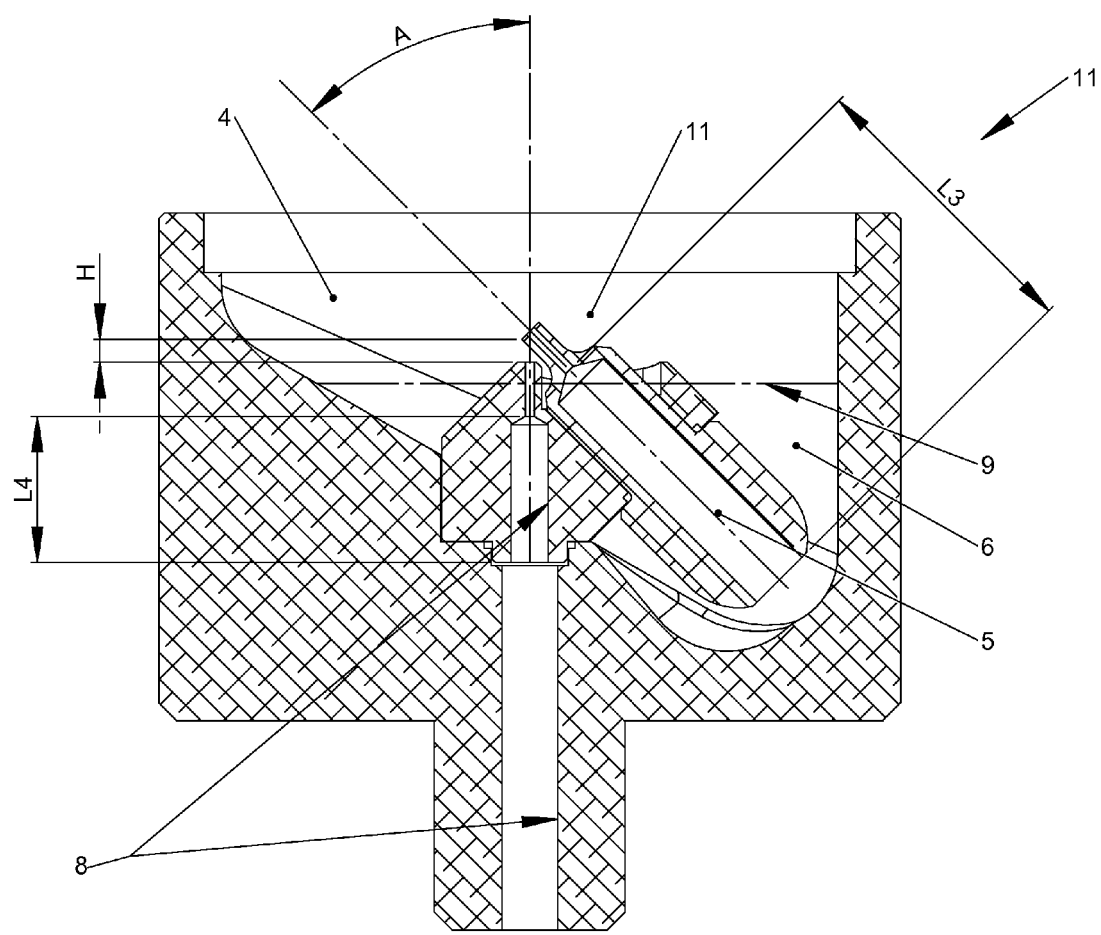
FIG. 3, shows, according to particular aspects of the present invention, a cross-sectional view of an exemplary atomization chamber of the exemplary nasal atomizer embodiment of FIG. 2.
Figure 4:
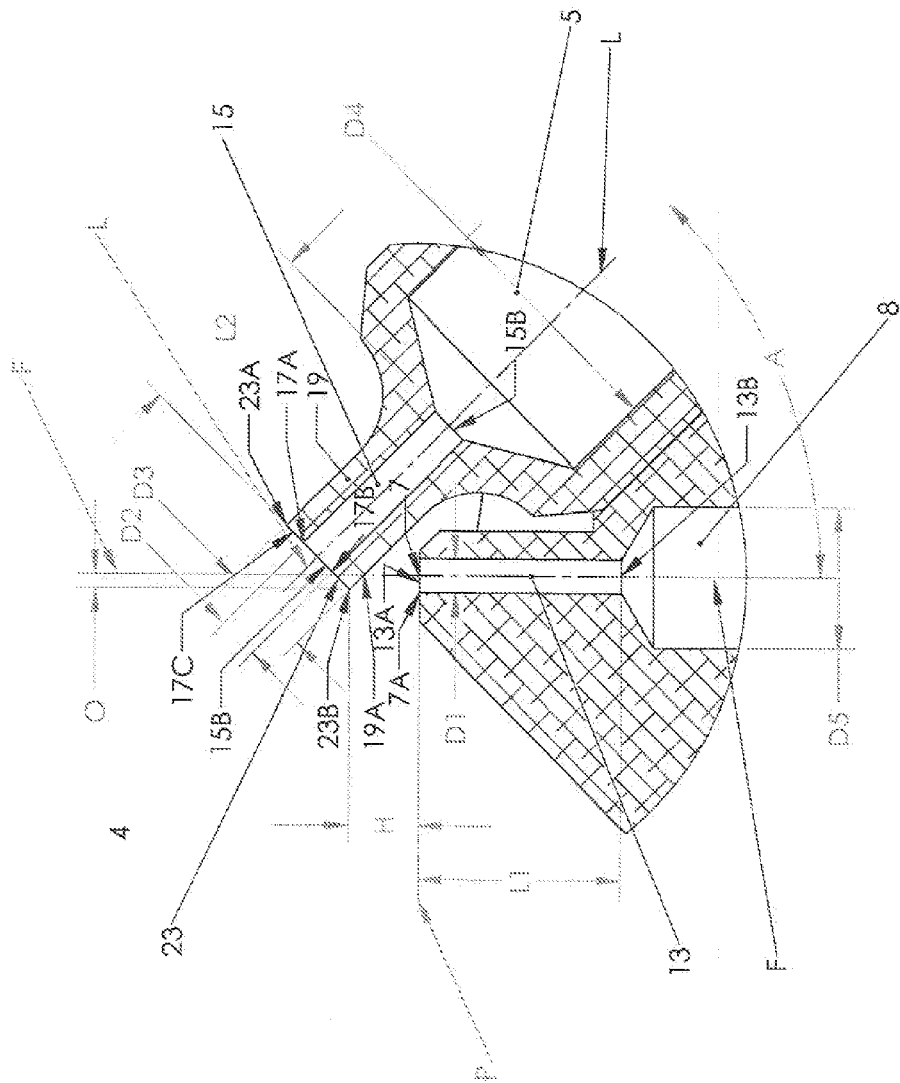
FIG. 4, shows, according to particular aspects of the present invention, a side cross-sectional view of the particle generating portion (atomization means) of the atomization chamber of FIG. 3. The letter designations "O" "D1," "D2," "D3," "D4," "D5," "H," "A," "J," "L1," "L2," "L3," and "L4" delineate particular variable aspects of the particle generation portion that can be adjusted to alter the MMAD particle distribution.

With reference to FIGS. 2-4 and the definitions provided below, an overview of aspects of the present invention will now be described. An exemplary embodiment of an atomizer 1 configured for nasal delivery of aerosolized particles is shown in FIG. 2. The atomizer 1 includes an atomization housing 2 defining an atomization chamber 4 in communication with, or comprising holding means (e.g., a reservoir portion 6) suitable for holding a liquid (e.g., medicament solution), which can be filled to one or another suitable level (e.g., consistent with the configuration, and desired dosage, etc.) identified or marked by reference numeral 9 (FIG. 3).

The atomizer 1 may include an atomization means 11 housed inside the atomization housing 2. The atomization means 11 includes a primary liquid feed channel 15 in communication with the liquid held in the holding means. The primary liquid feed channel 15 may receive the liquid from a secondary liquid feed channel 5 that is in fluid communication with the holding means (e.g., the reservoir portion 6). In other words, the secondary liquid feed channel 5 is intermediate between the primary liquid feed channel 15 and the holding means.

The atomization means 11 may be optionally driven by a compressed fluid source (not shown), inhalation, and the like. For convenience of illustration, the compressed fluid driven embodiments will described first. In such embodiments, the atomization means 11 includes a primary compressed fluid channel 13 in communication with an external or internal compressed fluid source (not shown). As may best be viewed in FIG. 4, the primary compressed fluid channel 13 has a corresponding orifice 7 defining a projectable longitudinal compressed fluid feed channel axis "F," in operative communication with the primary liquid feed channel 15 and its corresponding orifice 17. The primary compressed fluid channel 13 receives compressed fluid from a secondary compressed fluid channel 8 in fluid communication with the compressed fluid source (not shown). In other words, the secondary compressed fluid channel 8 is intermediate between the primary compressed fluid channel 13 and a source of compressed fluid. The atomization means 11 is suitably configured to entrain a liquid in a fluid flow stream (not shown) to generate a particle (e.g., aerosolized liquid droplet) flow along (e.g., centered along) the projected axis "F."

In embodiments driven by inhalation, the secondary compressed fluid channel 8 may be open to the ambient air and inhalation by the user may draw ambient air into the secondary compressed fluid channel 8 and the primary compressed fluid channel 13 couple thereto. In such embodiments, the "compressed fluid" in the primary compressed fluid channel 13 may include air drawn into the device by the user's inhalation.

Returning to FIG. 2, the atomizer 1 may include an aerodynamic particle-size filtering means or filtering member 21 (e.g., air-foil member) suitably configured and positioned at a distance "J" from the primary orifice plane "P" (defined by the primary compressed fluid orifice 7 in a manner explained below) to direct fluid flow around its contour, and thereby non-collisionally redirect particle flow of the desired particle size range around its contour, while simultaneously blocking larger particles for return to the liquid reservoir and re-entrainment. In other words, the filtering member 21 separates particles having a size larger than a predetermined size from particles having a size less than or equal to the predetermined size. The particles having a size larger than the predetermined size are collected by the filtering member 21 and returned to the holding means. The particles having a size less than or equal to the predetermined size pass by the filtering member 21.

Optionally, the atomizer 1 may include a particle dispersion chamber 10 having an optional dispersion chamber outer housing 28, an optional intermediate compressed fluid channel 40, various connector components used to couple these components to the atomization chamber 4, and the like. The dispersion chamber outer housing 28 may be optionally fitted with a nasal adapter 42 (see FIGS. 2 and 7-9), a nasal adapter 60 (see FIGS. 13-17), an ocular adapter 48 (see FIGS. 10 and 11), an oral adapter (see FIGS. 18-21), and the like. As is apparent to those of ordinary skill, atomizers and nebulizers may be configured for use with various accessories, adapters, and the like and the invention is not limited to use with any particular accessories, adapters, and the like.

DEFINITIONS

The term "liquid," as used herein with respect to a liquid to be atomized using the inventive devices and methods, refers to any liquid or solution, including medicament solutions and drug or agent formulations and solutions. Liquid also encompasses liquids and solutions of various viscosities.

The terms "particle filter," "particle size filter" (e.g., aerodynamically particle size filtering means), and "splitting means," as used herein, refer to a particle filter (e.g., an aerodynamic particle size filtering member) suitably configured and positioned at the distance "J" from the primary compressed fluid orifice 7 (e.g., from a primary orifice plane "P", as defined herein) to provide an aerodynamic fluid flow around the surface. Preferably, the particle filter, and/or the configuration and placement thereof, provides for a proportion of atomized particles that collide with the member and a proportion of non-colliding particles with velocity vectors that avoid the surface and/or are carried in the aerodynamic fluid flow around the surface.

The term "holding means" as used herein, refers to a liquid or solution reservoir (e.g., the reservoir portion 6) for holding the liquid or solution to be atomized. Liquid or solution in the holding means is in communication with the atomization means 11 via one or more liquid feed channels (e.g., the secondary liquid feed channel 5). In preferred embodiments, the holding means is configured so that impaction liquid from the inventive filtering member 21 is returnable to the holding means for re-entrainment by the atomization means 11. The holding means can be of any suitable configuration, and, for example, can be configured as part of the atomization chamber 4 per se, or alternatively can be a holding means (e.g., a cartridge, vial or other liquid, solution or medicament container) that is insertable into the atomization chamber 4 so that a liquid, solution or medicament contained therein is in communication with the atomization means 11.

The term "primary orifice plane 'P'" as used herein with respect to particular exemplary embodiments, refers to a positional reference plane normal to the projectable longitudinal compressed fluid feed channel axis "F", definable by the configuration and contour of a perimeter 7A (e.g., circular perimeter, or otherwise) of the primary compressed fluid orifice 7. As shown in the exemplary embodiments described herein, the perimeter 7A of the primary compressed fluid orifice 7 defines a normal, horizontal surface, for which the reference primary orifice plane "P" provide direct reference (e.g., for purposes of describing the distance of a filtering member 21 or other element along the axis "F"). It should be understood, however, that the precise shape of the perimeter 7A of the primary compressed fluid orifice 7 may be other than the exemplary regular, normal or horizontal shape and may assume a variety of suitable configurations, and in such cases the positional reference plane (i.e., the primary orifice plane "P") will still be normal to the projectable longitudinal compressed fluid feed channel axis "F", but will be positioned along the axis "F" at the median position along axis "F" of the primary compressed fluid orifice 7, regardless of the regularity, shape, slope, configuration, etc., thereof. For example, if the primary compressed fluid orifice 7 is circular, but is angled (slopped) rather than normal to the axis "F", then primary orifice plane "P" will be a plane "P" positioned normal to axis "F", but at a position along axis "F" corresponding to the center point of the primary compressed fluid orifice 7. In this manner, the primary orifice plane "P" serves its reference position function with respect to defining a distance to other elements of the inventive devices.

The term "channel end-wall face" as used herein with respect to particular exemplary embodiments, refers to a positional reference plane definable by the configuration and contour of a perimeter 17A of the primary liquid feed channel orifice 17 and the configuration and contour of an end-wall face 23 of the primary liquid feed channel 15. The end-wall face 23 having a perimeter 23A. As shown in particular exemplary preferred embodiments described herein, the perimeter 17A of the primary liquid feed channel orifice 17 and the perimeter 23A of the end-wall face 23 define a surface 17C that is normal to a liquid feed channel axis "L," and that is disposed at an acute angle "A" with respect to the axis "F." It should be understood, however, that the precise shape of the perimeter 17A of the primary compressed fluid orifice 17 and/or the perimeter 23A of the end-wall face 23 may be other than the exemplary regular, normal or horizontal or angled shape and may assume a variety of suitable configurations, and in such cases the end-wall face 23, regular or irregular, may be other that normal to the projectable longitudinal liquid feed channel axis "L". For example, if the primary liquid feed channel orifice 17 and end-wall face 23 is circular, but is but is horizontal (e.g., normal with respect to the axis "F"), then the orifice 17 and end wall face 23 (or a plane representing the average configuration/shape of the orifice and end-wall face) will be normal to axis "F", but at an angel with respect to axis "L". Therefore, a variety of suitable shapes and configurations of the primary compressed fluid orifice 17 and/or the end-wall face 23 are encompassed by the present invention, and these may be disposed at various angels with respect to the axis "F." Therefore, for purposes of the present invention, the positioning, with respect to the projectable axis "F", of the end-wall face 23 and orifice 17 thereof are defined by the positioning, normal to axis "F," of a closest plane "I"-intersecting portion 23B of the perimeter 23A of the end-wall face 23, where plane "I" is a plane defined by the intersection of the axis "F" with the axis "L". In this manner, the distance of the perimeter 23A of the end-wall face 23 from the axis "F" can be defined, regardless of the shape, configuration, or orientation of the end-wall face 23 and the primary liquid feed channel orifice 17 thereof.

Atomization Means 11

As mentioned above, the atomization housing 2 houses the atomization means 11 and defines an atomization chamber 4 in communication with, or comprising holding means. Alternatively, the atomization means 11 may include a housing 2A having a wall 2C defining the atomization chamber 4 in which the liquid or solution is atomizable. In the embodiment depicted in FIG. 2, the atomization chamber 4 includes a reservoir portion 6 that serves as the holding means suitable for holding a liquid or solution to be atomized.

With reference to FIGS. 2, 3, and 4, to allow for compressed fluid-driven (e.g., compressed air-driven) particle generation, the atomization chamber 4 is in communication with the compressed fluid source (e.g., an air compressor, tank, compressed gas cartridge, and the like) via the primary compressed fluid orifice 7, the primary compressed fluid feed channel 13, and, in certain embodiments, a secondary compressed fluid channel 8 that communicates between the primary compressed fluid feed channel 13 and the source of compressed fluid. The primary compressed fluid orifice 7 is located at a first end 13A of the primary compressed fluid feed channel 13, is in fluid communication with the atomization chamber 4, and defines the primary orifice plane "P." A second open end 13B opposite the first end 13A of the channel 13 is in fluid communication with the compressed fluid source (e.g., an air compressor), which may, in certain embodiments, may be via the secondary compressed fluid channel 8. The channel 13 and/or orifice 7 define the projectable compressed fluid feed channel axis "F."

The primary compressed fluid feed channel 13 (e.g., cylinder, tube, channel, bore, etc.) has a length "L2," an inner diameter "D1." The secondary compressed fluid channel 8 has an inner diameter "D5" and a length "L4" (see FIG. 3). In the embodiment depicted in the drawings, the secondary compressed fluid channel 8 has a first portion 8A coupled to the channel 13 and a second larger diameter portion 8B coupled between the first portion 8A and the compressed fluid source (not shown). In the embodiment depicted in FIG. 2, compressed fluid is supplied to the atomization chamber 4 via a channel having three segments of decreasing inner diameter (i.e., the second portion 8B, the first portion 8A, and the primary compressed fluid channel 13). However, as is apparent to those of ordinary skill in the art, embodiments in which the inner diameter "D5" of the first portion 8A is greater than or substantially equal to the inner diameter of the second portion 8B are also within the scope of the present invention.

As may best be viewed in FIG. 4, the primary liquid feed channel 15 (e.g., cylinder, tube, channel, bore, etc.) has a length "L2," an inner diameter "D2," a channel wall 19, and a channel end-wall face 23 at a first end 15A. The channel 15 also includes an outside diameter "D3" disposed about (e.g., radially about) the primary liquid feed channel orifice 17 in fluid communication with the atomization chamber 4. The primary liquid feed channel 15 has a second end 15B in optional communication with a secondary liquid feed channel 5 having a length "L3" (see FIG. 3) and an inner diameter "D4." The secondary liquid feed channel 5 is in communication with the liquid holding means 6. The primary liquid feed channel 15 defines a projectable longitudinal liquid feed channel axis "L."

According to preferred aspects, the inventive, highly efficient atomization means 11 is uniquely configured such that: (a) the channel end wall face 23 with the liquid feed channel orifice 17 is separated by at least a distance "H" (e.g., vertical distance or height, in the case of vertically oriented embodiments) from the a primary orifice plane "P," the distance "H" being measured along the projected longitudinal axis "F"; and (b) the longitudinal axis "L" intersects the longitudinal axis "F" at the acute angle "A." In preferred embodiments, and at the distance "H" along the axis "F," the plane "I"-intersecting portion 23B of the perimeter 23A of the end wall face 23 is positioned within a selected distance "S" from axis "F" (measured perpendicular to the axis "F") and this distance is sometimes referred to herein as the offset distance "O."

In some embodiments, the selected distance "S" is such that there is 'overlap' of axis "F" with the plane "I"-intersecting portion 23B of the perimeter 23A of the end wall face 23, where, as used herein, there is 'overlap,' if the projected axis "F" intersects the end wall face 23 or the liquid feed channel orifice 17 thereof. In such overlapping embodiments the selected distance "S" is sometimes referred to herein as a negative offset "minus O" distance. When there is negative offset (i.e., a minus O distance), the orifice 7 is positioned adjacent to a diverting portion 19A of the wall 19 of the primary liquid feed channel 15 aligning at least a portion of the flow of compressed fluid along axis "F" with the diverting portion 19A of the wall 19 and causing a first portion of the compressed fluid to strike (or impact) the diverting portion 19A of the wall 19. A portion of the compressed fluid is also directed around the outside of the diverting portion 19A of the wall 19. Without being limited by theory, directing the flow of compressed fluid around the diverting portion 19A may disrupt or spread the column of compressed fluid leaving the orifice 7. Therefore, unlike prior art or conventional atomizers and nebulizers that avoid spreading or disrupting the flow of compressed fluid before it strikes the impactor thereby maximizing the portion of the flow of atomized particles that strike the impactor, certain embodiments of the present invention spread the flow of compressed fluid before it engages the liquid to be atomized.

In various embodiments, outside of the diverting portion 19A of the wall 19 may be contoured. As the compressed fluid traverses the contoured surface, the velocity of the fluid is increased and pressure around the diverting portion 19A of the wall 19 may decrease to below that of the uninterrupted flow of compressed fluid. In the embodiment depicted in FIG. 4, the orifice 7, channel 15, and wall 19 thereof are arranged such at the orifice 7 extends substantially between the portion 23B of the perimeter 23A of the channel end face 23 and the center of the channel 15 along plane "P." In this embodiment, the compressed fluid will be traveling at different rates along the diverting portion 19A in the axial direction of axis "F." Specifically, the fluid will be traveling faster near the center of the orifice 7 than near the portion 23B of the perimeter 23A of the end wall face 23 where it traverses a smaller portion of the diverting portion 19A.

In other embodiments, the selected distance "S" is such that there is no 'overlap' of axis "F" with the plane "I"-intersecting portion 23B of the perimeter 23A of the end wall face 23 (i.e., the projected axis "F" does not intersect the end wall face 23 or the liquid feed channel orifice 17 thereof). In such non-overlapping embodiments, the selected distance "S" is sometimes referred to herein as a positive offset "plus O" distance.

In particular embodiments, the selected distance "S" from projected axis "F" is less than or equal to ½×D1, and in instances where there is no overlap as defined herein, this distance would correspond to a "plus O" value that is less than or equal to ½×D1. In alternate embodiments, the selected distance "S" from projected axis "F" is less than or equal to ½×D1, and in instances where there is overlap as defined herein, this distance would correspond to a "minus O" value that is less than or equal to ½×D1 (see, e.g., "O" in FIG. 4). In particular embodiments, offset distance "O" (plus or minus) is less, equal to or greater than ½×D1. In particular embodiments, offset distance "O" (plus or minus) is less than ½×D1, and preferably "minus O" is less than ½×D1. In particular embodiments, neither the plane-I-intersecting portion 23B of the perimeter 23A of the end wall face 23 nor a plane-I-intersecting portion 17B of the perimeter 17A of the liquid feed channel orifice 17 overlap projected axis "F." In other embodiments, the plane-I-intersecting portion 23B of the perimeter 23A of the end wall face 23 overlaps projected axis "F," whereas the plane-I-intersecting portion 17B of the perimeter 17A of the liquid feed channel orifice 17 does not. In yet additional embodiments, both the plane-I-intersecting portion 23B of the perimeter 23A of the end wall face 23 and the plane-I-intersecting portion 17B of the perimeter 17A of the liquid feed channel orifice 17 overlap projected axis "F" (i.e., the projected axis "F" intersects the liquid feed channel orifice 17 of the end wall face 23).

It will be appreciated by those of skill in the art that the precise shape of the primary compressed fluid orifice 7 and/or the primary liquid feed orifice 17 may vary (e.g., circular, ovoid, rectangular, square, etc.), and that the present inventive aspects encompass such variations, and that the shapes may be regular (e.g., flat, smooth, gently curved) or irregular (jagged, abruptly curved, rough, etc.). Additionally, it will be appreciated by those of skill in the art that the precise angular disposition of the primary compressed fluid orifice 7 and/or the primary liquid feed orifice 17 with respect to the axis "F" and axis "L", respectively, may vary (e.g., normal, acute, obtuse), and that the present inventive aspects encompass such variations.

In particular embodiments, distance "H" is less than diameter "D1," equal to diameter "D1," or greater than diameter "D1." In particular embodiments, distance "H" is greater than diameter "D1." Preferably, distance "H" is equal to or greater than diameter "D1."

In some embodiments, distance "H" is less than diameter "D2," equal to diameter "D2," or greater than diameter "D2." In some embodiments, distance "H" is greater than diameter "D2." Preferably, distance "H" is equal to or greater than diameter "D2."

In particular embodiments, distance "H" is less than diameter "D3," equal to diameter "D3," or greater than diameter "D3." In some embodiments, distance "H" is less than diameter "D3." Preferably, distance "H" is equal to or less than diameter "D3."

In some embodiments, distance "H" is less than diameter "D3," but greater than diameter "D1," or distance "H" is less than diameter "D3," but greater than diameter "D2." In some embodiments, diameter "D2" is equal to or greater than diameter "D1." In some embodiments, the distance "H" is equal to or greater than ¼, ½ or 1× the inner diameter "D1" of the primary compressed fluid feed channel 13. In particular aspects, distance "H" is less than diameter "D3," and greater than both diameter "D1" and diameter "D2." In some embodiments, distance "H" is greater than any one of diameter "D1," diameter "D2," and diameter "D3."

In particular embodiments, the atomization means 11 is configured such that, during operation of the atomization device 1, the longitudinal primary fluid feed channel axis "F" of the primary compressed fluid feed channel 13 is vertically oriented, or substantially vertical (e.g., within 5 or 10 degrees of vertical), within the atomization chamber 4.

In particular embodiments, the diameter "D1" of the primary orifice 7 is from about 0.1 mm to about 1 mm, about 0.2 mm to about 0.6 mm, about 0.25 mm to about 0.4 mm, or preferably about 0.29 mm to about 0.46 mm.

In particular embodiments, the diameter "D2" of the primary liquid feed channel orifice 17 is from about 0.15 mm to about 1.5 mm, about 0.25 mm to about 1.0 mm, about 0.3 mm to about 0.75 mm, or preferably about 0.38 mm to about 0.50 mm.

In particular embodiments, the outer diameter "D3" of the primary liquid feed channel end wall face 23 is from about 0.2 mm to about 4.0 mm, about 0.4 mm to about 3.0 mm, about 0.6 mm to about 2.5 mm, or preferably about 0.76 mm to about 2.03 mm.

In other embodiments, diameter "D4" is from about 2 mm to about 2.5 mm. In various embodiments, the inner diameter "D4" is larger than the inner diameter "D2" of the primary liquid feed channel. In particular aspects, diameter "D4" is greater than or equal to 2×D2, 3×D2, 4×D2, 5×D2, 10×D2, 15×D2, 20×D2, 30×D2, 40×D2 or 50×D2. In particular embodiments, in inside diameter "D4" of the secondary liquid feed channel 5 is from about 1.5 mm to about 4 mm, about 1.5 mm to about 3 mm, or about 1.5 mm to about 2.5 mm. In some aspects, diameter "D4" is from about 1 mm to about 5 mm, from about 1.5 mm to about 3 mm, or from about 2 mm to about 2.5 mm. In such preferred embodiments, the relatively large diameter "D4" (i.e., relative to prior art atomization and nebulization devices which have relatively narrow liquid channels) enables atomization and delivery of relatively viscous liquids (e.g., 5-105 centipoise) and solutions that cannot be effectively atomized, nebulized or delivered by devices of the prior art (which cannot effectively atomize, nebulize or deliver particles greater than about 5 centipoise). According to preferred aspects, diameter "D4" is greater than the diameter of corresponding primary and secondary liquid feed channels of conventional prior art atomizers and nebulizers, thereby reducing the liquid flow resistance relative to prior art devices, and allowing for effective atomization and delivery of liquids of substantially increased viscosity relative to those liquids effectively atomizable or nebulizable by prior art devices. This also facilitates a higher rate of delivery (more mass delivered per unit time, relative to prior art devices). In particular embodiments, the distance "H" from the primary orifice plane "P" ranges from about 0.02 mm to about 5.0 mm, about 0.1 mm to about 5.0 mm, about 0.15 mm to about 4.0 mm, about 0.2 mm to about 3.0 mm, or preferably about 0.25 mm to about 2.03 mm.

In particular embodiments, the selected distance "S" or the offset distance "O" (plus or minus) from longitudinal axis "F" is less than, equal to, or greater than ½×D1. Preferably, selected distance "S" or offset distance "O" (plus or minus) is less than or equal to ½×D1. More preferably, selected distance "S" or offset distance "O" (plus or minus) is less than ½×D1. The selected distance "S" may be equal to or less than twice the inner diameter "D1" of the primary compressed fluid feed channel 13.

In particular embodiments, the angle "A" is between about 30 degrees and about 70 degrees, between about 45 degrees and about 70 degrees, or between about 55 degrees and about 65 degrees. In some embodiments, the angle "A" is about 55 degrees.

In particular embodiments, the distance "J" from the primary orifice plane "P" ranges from about 0.1 mm to about 40 mm, 0.1 mm to about 25 mm, 0.1 mm to about 5.0 mm, about 0.15 mm to about 4.0 mm, about 0.2 mm to about 3.0 mm, or preferably about 0.25 mm to about 2.0 mm.

Dispersion Chamber 10

The linear atomizer embodiment 1 of FIG. 2 additionally comprises a particle dispersion chamber 10 in fluid communication with the atomization means 11 of the atomization chamber 4. The particle dispersion chamber 10 imparts a velocity vector or flow pattern (e.g., 'vortical,' randomized, turbulent, etc. flow) to the aerosolized particles (e.g., atomized particles) received within and exiting from the particle dispersion chamber 10. Additionally, the particle dispersion chamber 10 serves to define further the particle size after the droplets are created by and received from the atomization means 11.

The particle dispersion chamber 10 comprises a housing 16 having a wall 16A, an atomization chamber-proximal input opening 16B, an atomization chamber-distal output opening 16C, and an internal particle dispersion channel 22 communicating between the input opening 16B and the output opening 16C. The input opening 16B is in fluid communication with the atomization chamber 4 and the particle dispersion chamber 10 is configured to operatively receive atomized particles therethrough from the atomization means 11. The atomization chamber 4 includes an open portion 4A through which atomized particles may exit the atomization chamber 4 and the particle dispersion chamber 10 includes an atomization chamber-proximal input opening 16B through which atomized particles may enter the particle dispersion chamber 10.

Figure 7:
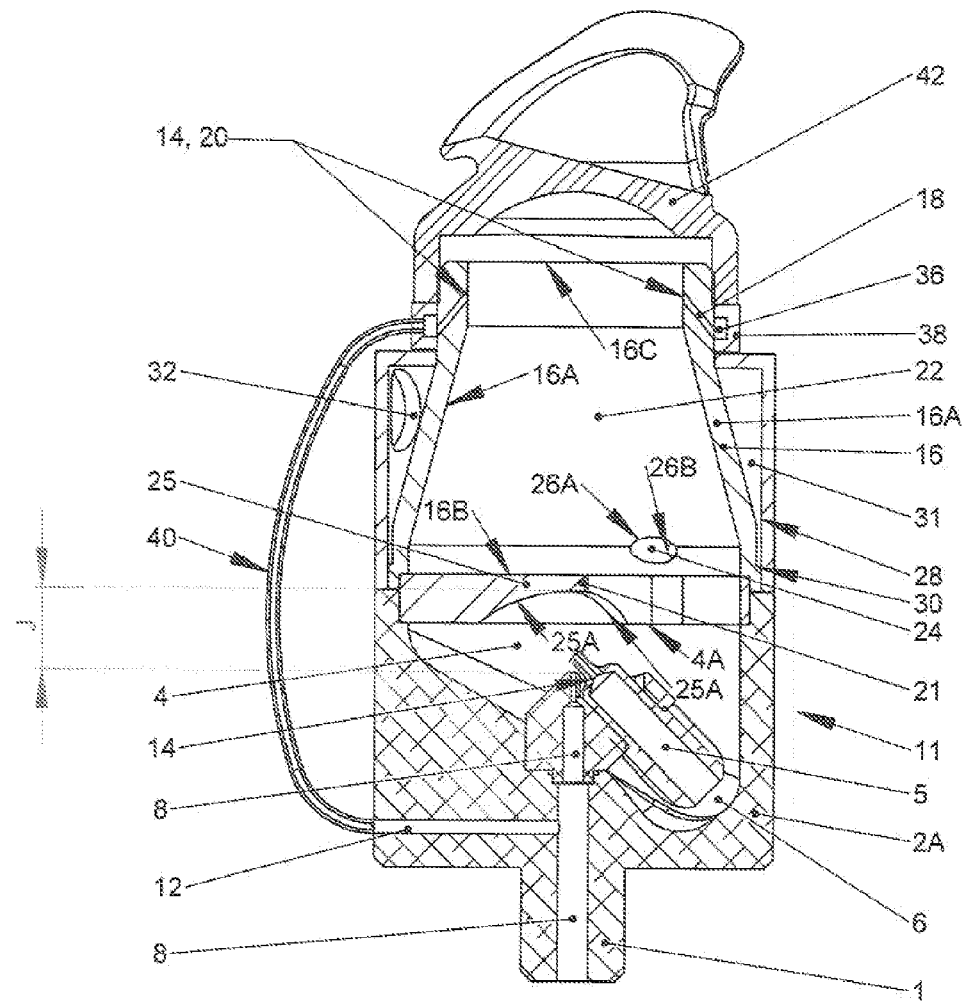
FIG. 7, shows, according to particular aspects of the present invention, a side cross sectional view of another exemplary nasal atomizer embodiment, comprising: atomization means; particle size filtering means; particle dispersion chamber with ambient air plenum member; compressed fluid plenum and compressed fluid outlet; and nasal adapter.
Figure 11:
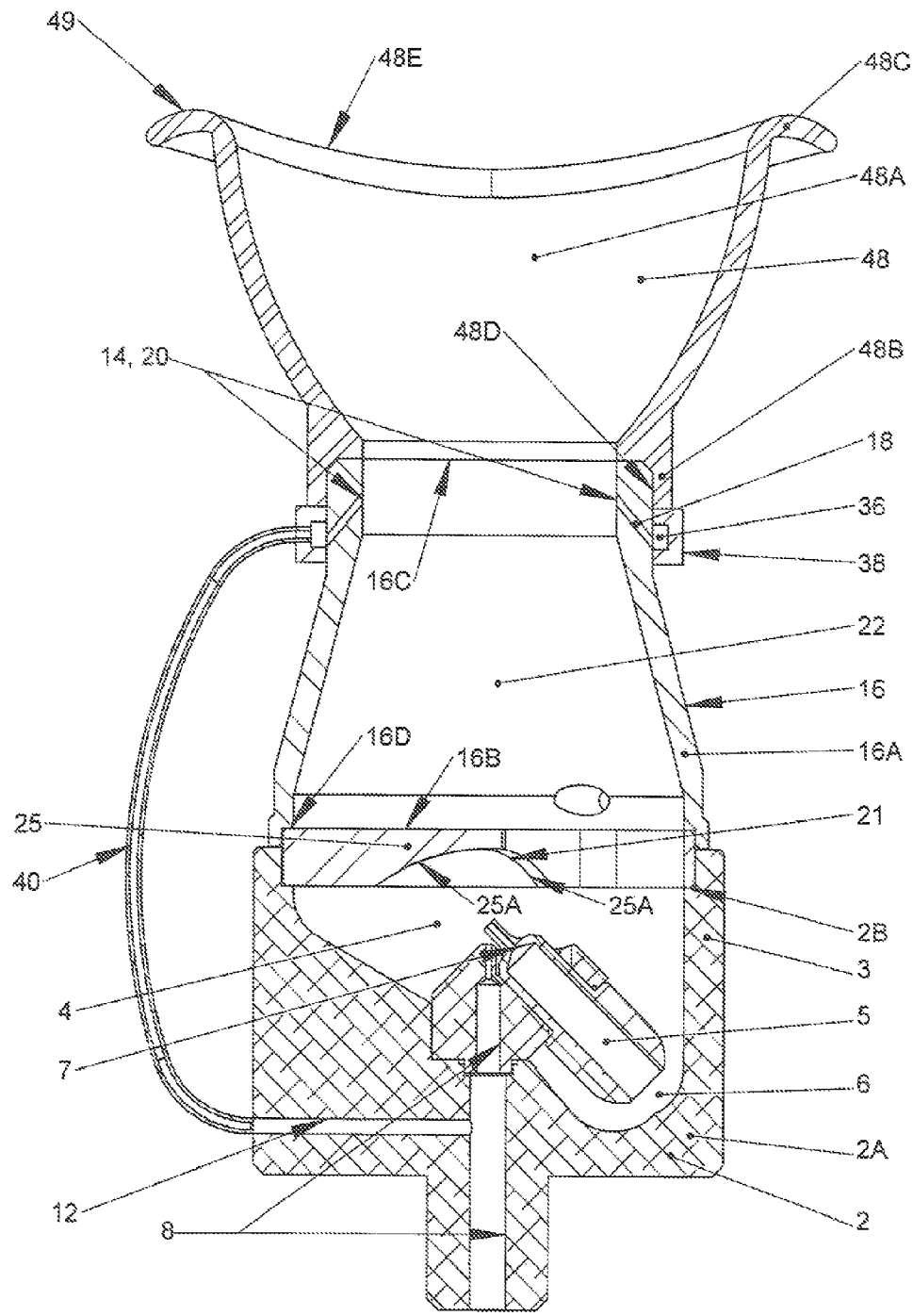
FIG. 11, shows, according to particular aspects of the present invention, a side cross-sectional view of an exemplary ocular atomizer embodiment, comprising: atomization means; aerodynamic particle size filtering means; particle dispersion chamber; and ocular adapter.

In the embodiments depicted in FIGS. 2, 7, and 11, the input opening 16B of the particle dispersion chamber 10 is coupled directly to the open portion 4A of the atomization chamber 4 to allow the passage of atomized particles from the atomization chamber 4 to the particle dispersion chamber 10. For example, the open portion 4A may be formed in the top of the atomization chamber 4 and the particle dispersion chamber 10 attached to the top of the atomization chamber 4 with its input opening 16B juxtaposed with the open portion 4A of the atomization chamber 4.

Figure 12:
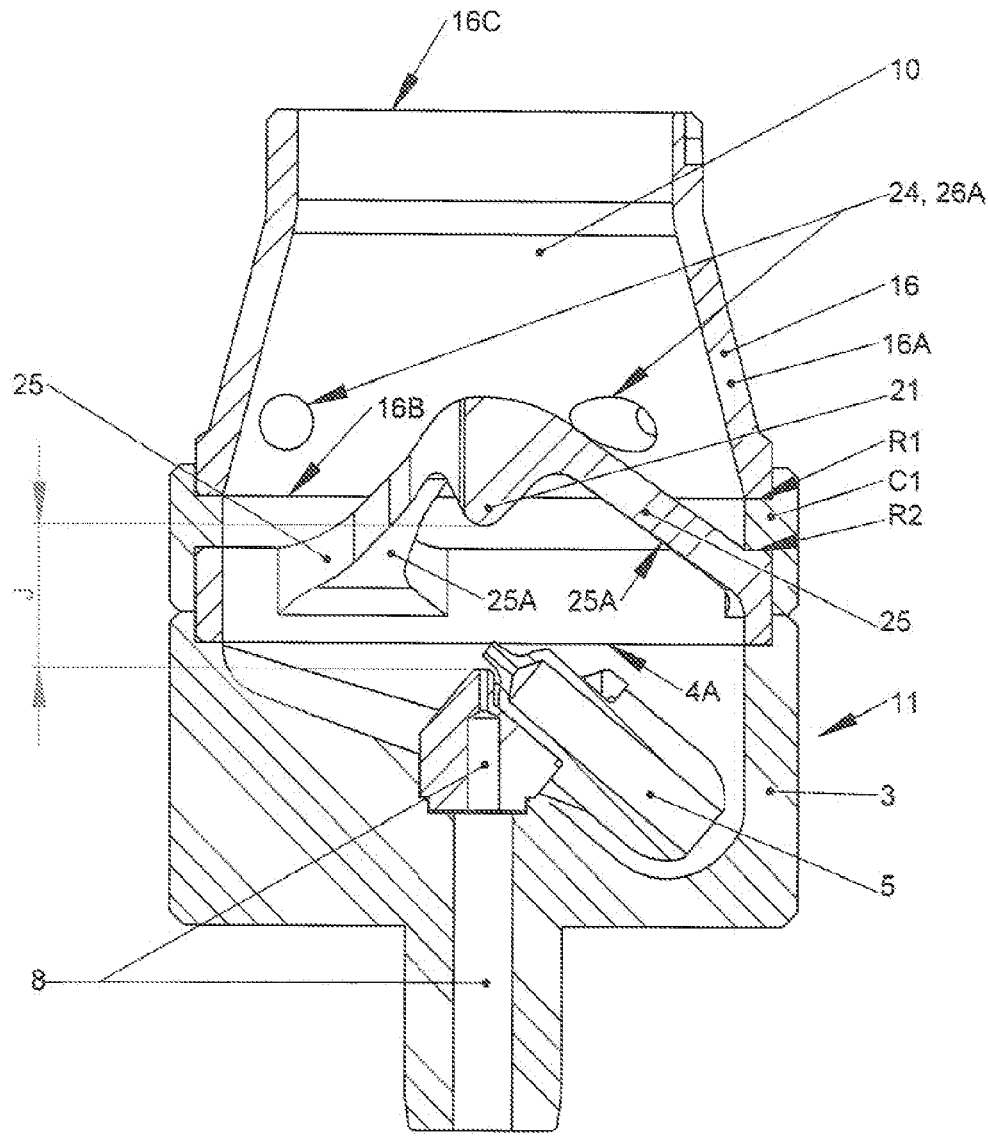
FIG. 12 shows, according to particular aspects of the present invention, a side cross sectional view of yet another exemplary nasal atomizer embodiment, comprising: atomization means; aerodynamic particle size filtering means; and particle dispersion chamber.
Figure 14:
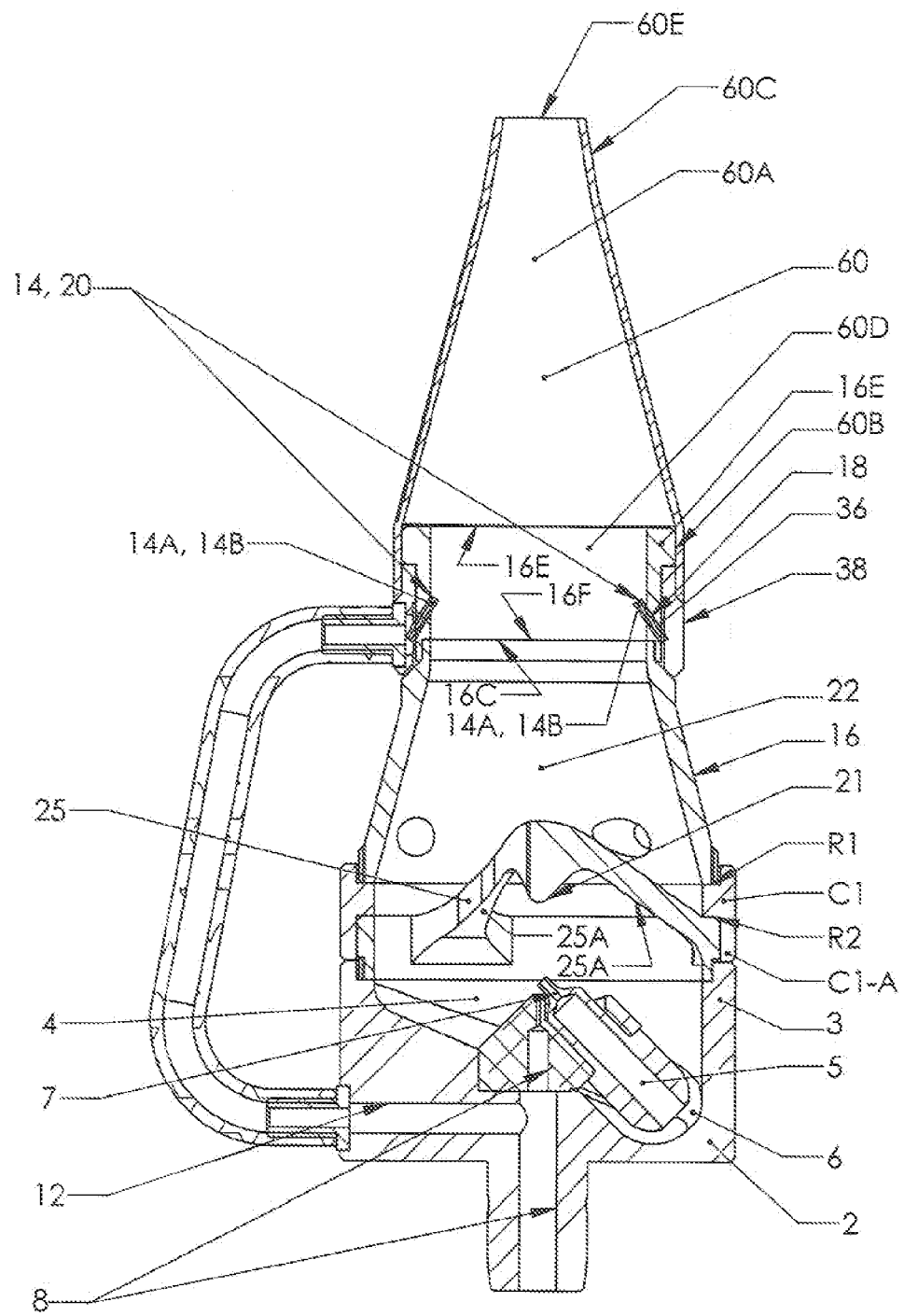
FIG. 14 shows, according to particular aspects of the present invention, a side cross sectional view of yet another exemplary nasal atomizer embodiment, comprising: atomization means; atomization chamber; aerodynamic particle size filtering means; particle dispersion chamber; a second intermediate compressed fluid channel, and a nasal adapter having an interface portion configured to be inserted into a nostril.
Figure 19:
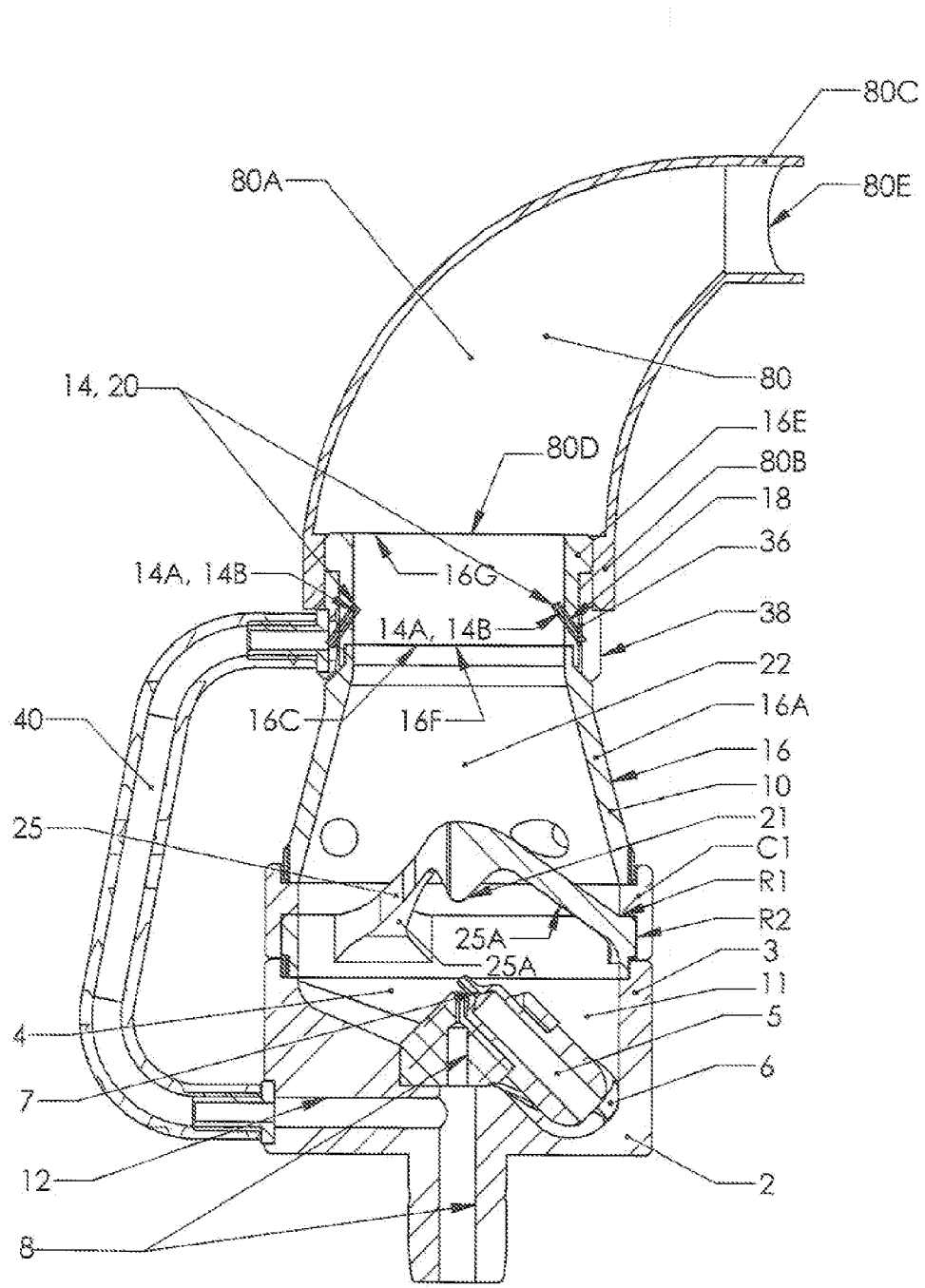
FIG. 19 shows, according to particular aspects of the present invention, a side cross sectional view of another exemplary oral atomizer embodiment, comprising: atomization means; atomization chamber; aerodynamic particle size filtering means; particle dispersion chamber; an intermediate compressed fluid channel, and an oral adapter.
Figure 20:
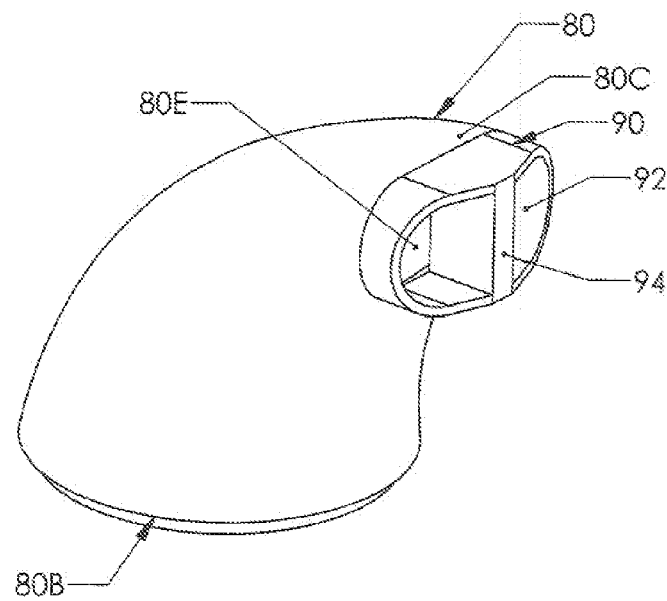
FIG. 20 shows, according to particular aspects of the present invention, an elevational perspective view of an exemplary embodiment of an oral adapter having a mouthpiece configured to be inserted into the mouth of a user. Such laterally deflecting embodiments also serve as vicinity adapters for delivery of aerosolized particles to the vicinity of a user or to desired target surfaces (e.g., for delivery of perfume, fragrance, essential oil or cosmeceutical agent and the like).
Figure 21:
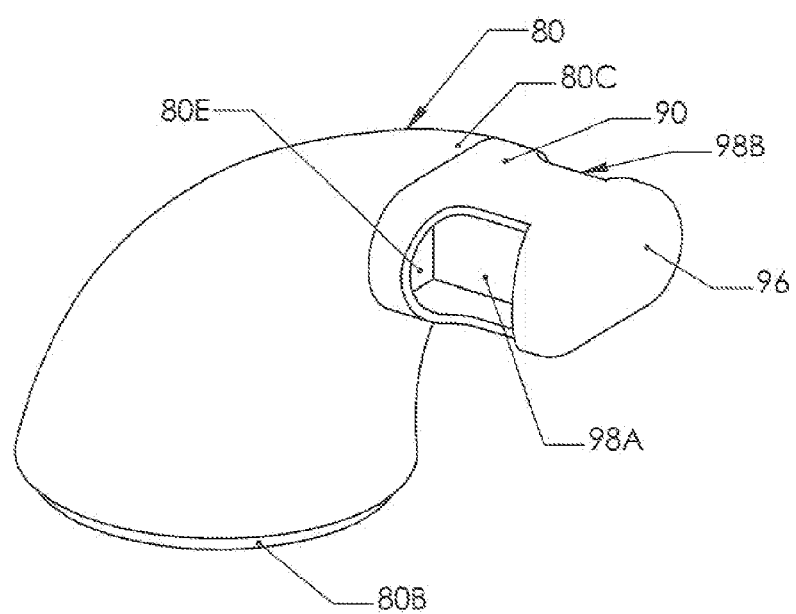
FIG. 21 shows, according to particular aspects of the present invention, an elevational perspective view of an exemplary embodiment of an oral adapter having a mouthpiece configured to be inserted into the mouth of a user. Such laterally deflecting embodiments also serve as vicinity adapters for delivery of aerosolized particles to the vicinity of a user or to target surfaces (e.g., for delivery of perfume, fragrance, essential oil or cosmeceutical agent and the like).

In alternate embodiments depicted in FIGS. 12, 14, and 19, a connector or collar "C1" is disposed between the particle dispersion chamber 10 and the atomization chamber 4. The collar "C1" may include a recessed portion "R1" configured to receive a portion of the particle dispersion chamber 10 and position the input opening 16B of the particle dispersion chamber 10 adjacent to the open portion 4A formed in the top of the atomization chamber 4.

The particle dispersion chamber 10 may additionally include, or communicate with, an aerodynamic particle size filtering member, 'splitter' member, or filtering member 21, suitably configured and positioned at a distance from the primary orifice plane "P" (defined by the primary compressed fluid orifice 7) to non-collisionally redirect flow of the desired particle size range around its contour while simultaneously blocking larger particles for return to the liquid reservoir and re-entrainment. In other words, the filtering member 21 separates particles having a size larger than a predetermined size from particles having a size less than or equal to the predetermined size. The particles having a size larger than the predetermined size are collected by the filtering member 21 and returned to the holding means. The particles having a size less than or equal to the predetermined size pass by the filtering member 21.

In the embodiments depicted in the figures, the filtering member 21 is disposed between the input opening 16B of particle dispersion chamber 10 and the open portion 4A of the atomization chamber 4. In this manner, the filtering member 21 selectively filters particles larger than a predetermined size from the particle stream preventing them from entering the particle dispersion chamber 10 and returning them to the holding means to be re-aerosolized.

An upper portion of the wall 2A defining the atomization chamber 4 may include a lip 2B configured to receive and support the filtering member 21 adjacent the open portion 4A. In the embodiments depicted in FIGS. 2, 5B, 6, 7, and 11, a lower portion of the wall 16A located in the interior of the chamber 10 may include a recessed portion 16D configured to receive a portion of the filtering member 21 and rest thereupon. In alternate embodiments depicted in FIGS. 12, 14, and 19, the collar "C1" includes a recessed portion "R2" configured to receive a portion of the filtering member 21 and rest thereupon.

Preferably, the internal channel 22 of the chamber 10 is configured so as to sustain, and not disrupt, the particle flow or dispersion pattern generated therein and exiting therefrom through the output opening 16C. Preferably, therefore, the internal channel 22 is, for example, cylindrical or substantially cylindrical (e.g., slightly tapered), smooth tapered cylindrical, etc., such that there are no abrupt discontinuities along the internal surface thereof, or surface structures or elements extending within the internal channel 22, or end caps, restrictions or elements that restrict the output opening 16C of the channel 22, that would disrupt the flow pattern imparted to the particles within the internal channel 22 and exiting the output opening 16C thereof.

The particle dispersion chamber 10 additionally comprises one or more directed fluid channels (e.g., 18 or 24) within the wall 16A suitable, in operation, to impart a desired velocity vector flow pattern (e.g., 'vortical,' randomized, turbulent, etc., flow) to aerosolized particles within and exiting the internal channel 22 through its output opening 16C. In particular embodiments, such as those shown in FIGS. 1-6, the wall 16A of the particle dispersion chamber 10 comprises at least one ambient air channel 24 having a first ambient air channel orifice 26A communicating with the internal channel 22 of the particle dispersion chamber 10 and a second ambient air channel orifice 26B in communication with ambient air. In particular embodiments, the at least one ambient air channel 24 and ambient air channel orifice 26A is configured within the wall 16A to operatively direct ambient air (e.g., during user inhalation) tangentially with respect the longitudinal axis of the internal channel 22 of the particle dispersion chamber. In other embodiments, the at least one ambient air channel 24 and ambient air channel orifice 26A are configured within the wall 16A to operatively direct ambient air (e.g., during user inhalation) tangentially and at an acute forward angle with respect a longitudinal axis of the internal channel 22 of the particle dispersion chamber 10; that is, preferably, the ambient air flow vector from the ambient air channel orifice 26A is directed tangentially with respect to the internal channel 22 configuration, and the flow vector has both radial and longitudinal components with respect to the internal channel 22 axis, such that the flow is suitable to impart, for example, a 'vortical' flow to aerosolized particles within and exiting the particle dispersion chamber 10. In alternate embodiments, the ambient air channels 24 and ambient air channel orifices 26A are configured (e.g., within the wall 16A of the particle dispersion chamber 10) to operatively impart a different (e.g., randomized, turbulent, etc.) velocity vector (flow) pattern to aerosolized particles within and exiting the particle dispersion chamber 10. According to preferred aspects, optimal particle size and velocity vector (particle flow) patterns afford efficient and effective targeted delivery of aerosolized particles (e.g., atomized particles) to, for example the nasal cavity and to regions thereof. In particular embodiments, the at least one ambient air channel 24 and orifice 26A are located in the wall 16A at or near the base (input opening) of the particle dispersion chamber 10 and channel 22. Alternatively, the at least one ambient air channel 24 and orifice 26A are located in the wall 16A at any wall position along the longitudinal channel 22 axis suitable to impart a velocity vector flow pattern to particles within and exiting the particle dispersion chamber 10 and channel 22 opening thereof.

Figure 5A:
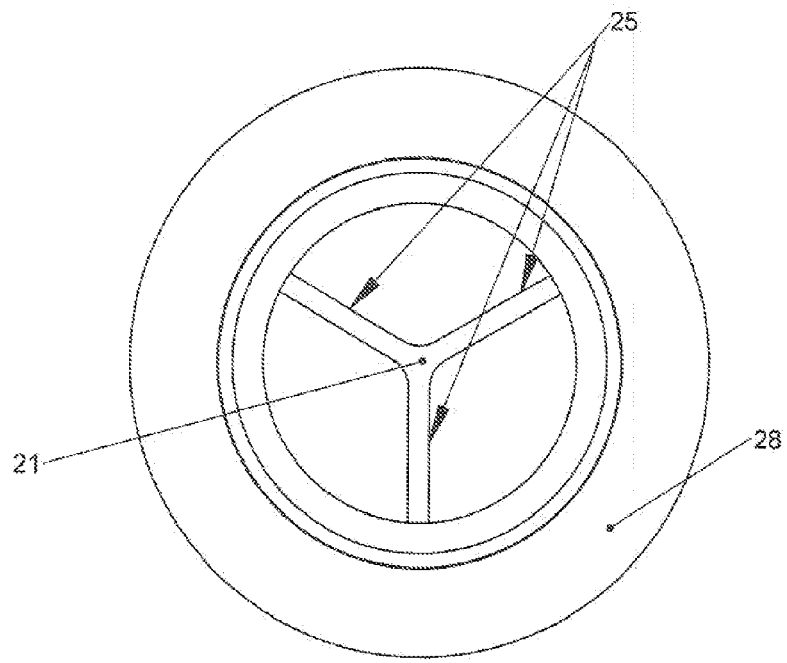
FIGS. 5A and 5B, show, according to particular aspects of the present invention, a top plan view, and a side cross-sectional view, respectively, of an exemplary particle dispersion chamber and aerodynamic particle size filter means of the exemplary nasal atomizer embodiment of FIG. 2.
Figure 5B:
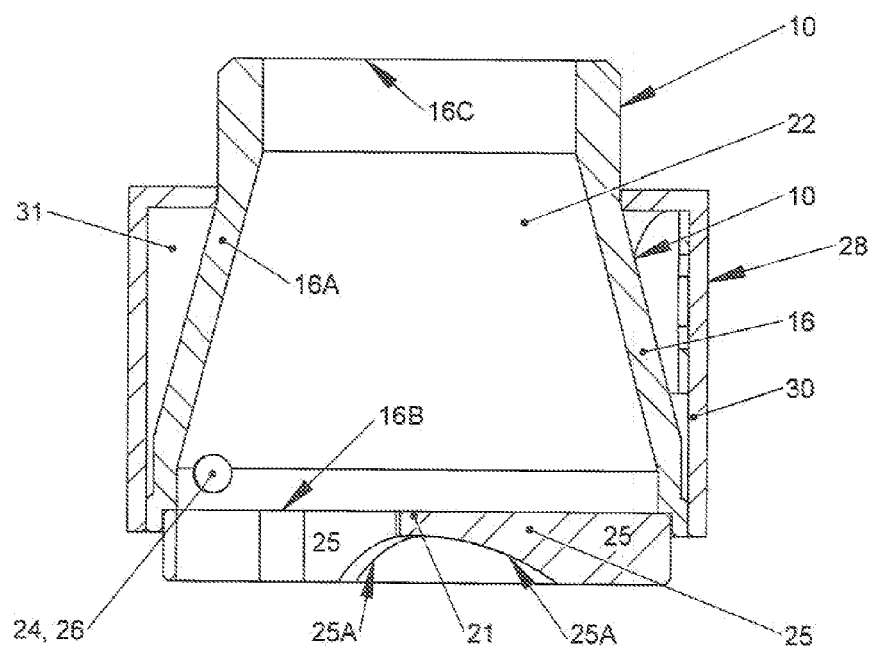
Figure 6:
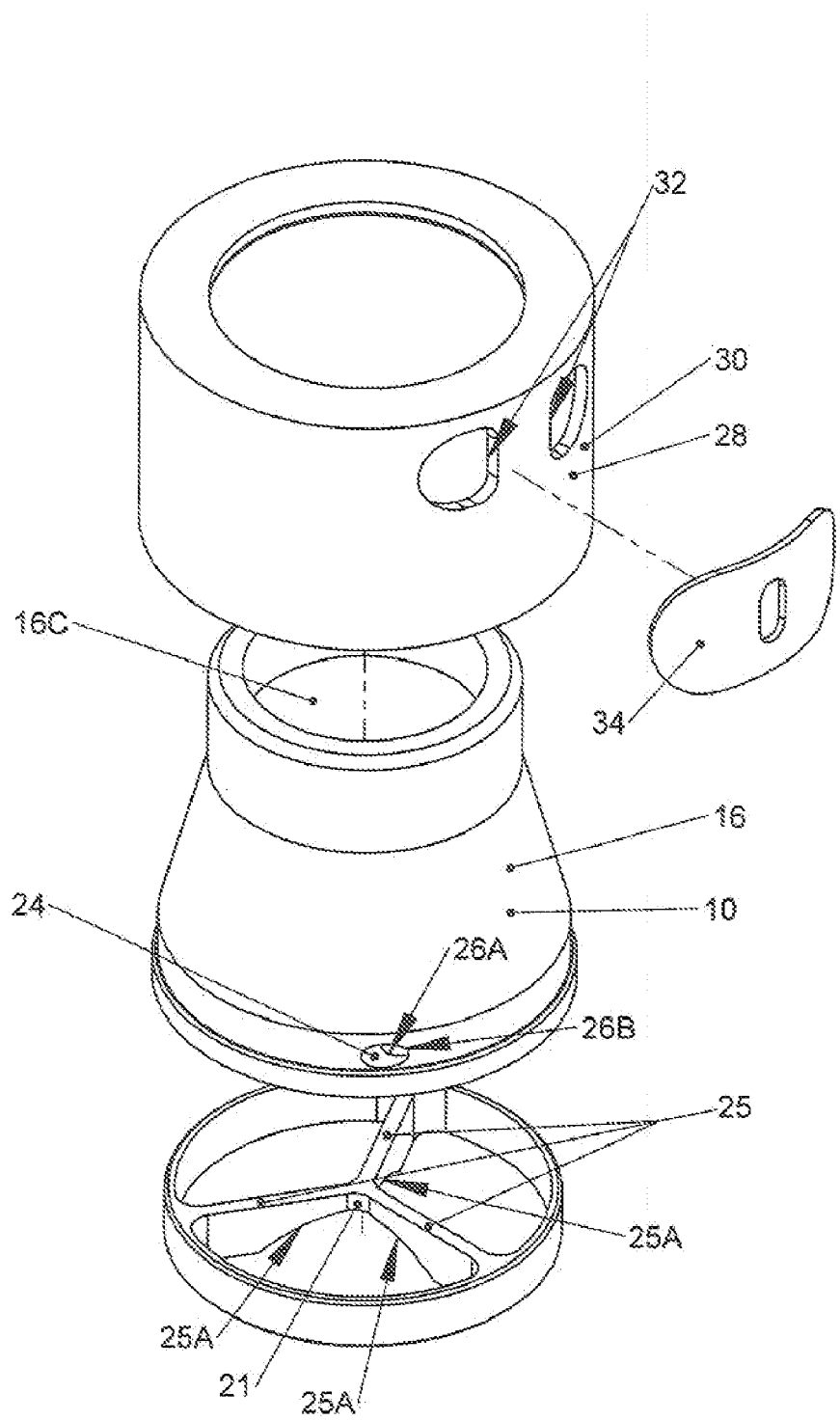
FIG. 6, shows, according to particular aspects of the present invention, an exploded perspective view of the exemplary particle dispersion chamber of FIG. 5, including the particle size filtering means and plenum member.

The embodiments of the particle dispersion chamber 10 depicted in FIGS. 2, 5 and 6, which include at least one ambient air channel 24 and corresponding inner orifice 26A may optionally comprise an outer housing 28 having a wall 30 defining a plenum space 31 between the outer housing wall 30 and wall 16A of the particle dispersion chamber 10. Preferably, the outer housing wall 30 comprises at least one opening 32, with optional one-way valve 34. Preferably, the at least one ambient air channel 24 and corresponding orifice 26A communicate with the at least one opening 32 by means of the plenum space 31, such that, during inhalation by user, inhaled air enters through opening 32 (see, e.g., FIG. 6), and is directed through the plenum space 31 and further through the ambient air channel 24 and orifice 26A and into the internal channel 22 of the particle dispersion chamber 10 to impart a flow pattern to particles within and exiting the channel 22.

Intermediate Compressed Fluid Channel 40

In the embodiment depicted in FIGS. 7, 11, 14, and 19, the secondary compressed fluid channel 8 communicates directly with the particle dispersion chamber 10 via an intermediate compressed fluid channel 40. In addition to the secondary compressed fluid channel 8 for particle generation, the atomization means 11 may include a particle dispersion chamber feed channel 12 configured to communicate between the compressed fluid channel 8 and one or more directed fluid channels that include 'directed' compressed fluid outlets 14 with corresponding compressed fluid outlet channel 18 and compressed fluid outlet orifices 20 within the wall 16A of the particle dispersion chamber 10 to provide for imparting a velocity vector pattern (e.g., 'vortical,' turbulent, randomized, etc.) to particles within and exiting the particle dispersion chamber 10 and integrated atomizer 1.

In particular embodiments, the directed compressed fluid outlets 14 comprise an outlet channel 18 through the wall 16A of the particle dispersion chamber 10. The outlet channel 18 has a compressed fluid outlet orifice 20 opening into the internal channel 22 of the particle dispersion chamber 10. The outlet channel 18 and orifice 20 are configured to operatively direct compressed fluid tangentially and at an acute forward angle with respect the longitudinal axis of the internal channel 22 of the particle dispersion chamber; that is, in such embodiments the compressed fluid flow vector from the outlet orifice 20 is directed tangentially with respect to the internal channel 22 configuration, the flow vector having both radial and longitudinal components with respect to the internal channel axis, such that the flow is suitable to impart, for example, a 'vortical' flow to aerosolized particles within and exiting the particle dispersion chamber 10. In alternate embodiments, the outlet channels 18 and compressed fluid outlet orifices 20 are configured (e.g., within the wall 16A of the particle dispersion chamber 10) to operatively impart a different (e.g., randomized, turbulent, etc.) flow to aerosolized particles within and exiting the particle dispersion chamber 10. According to preferred aspects of the present invention, optimal particle size and velocity vector patterns afford targeted delivery of aerosolized particles (e.g., atomized particles) to, for example the nasal cavity and to regions thereof.

In particular embodiments, the at least one compressed fluid outlet channel 18 and compressed fluid outlet orifice 20 is located in the wall 16A at or near the upper end (output opening) of the particle dispersion chamber 10 and channel 22. Alternatively, the at least one outlet channel 18 and compressed fluid outlet orifice 20 is located in the wall 16A at any wall position along the longitudinal channel 22 axis suitable to impart a velocity vector flow pattern to particles within and exiting the particle dispersion chamber 10 and channel 22 opening thereof.

In particular preferred embodiments, and with reference to FIGS. 7 and 11, there is a compressed fluid plenum space 36 defined by a dispersion chamber collar member 38. The compressed fluid plenum space 36 communicates between the particle dispersion chamber feed channel 12 and the at least one compressed fluid outlet channel 18 and compressed fluid outlet orifice 20. In particular embodiments, the compressed fluid plenum space 36 communicates with the particle dispersion chamber feed channel 12 through an intermediate compressed fluid channel 40, which may run externally, internally, or integrally with respect to the other device elements.

In the embodiment depicted in FIGS. 14, and 19, the atomizer embodiment 1 includes an extender portion 16E having a generally tube-like shape with an input aperture 16F and an exit aperture 16G formed therein. The extender portion 16E is coupled to the wall 16A of the particle dispersion chamber 10 and extends the top of the particle dispersion chamber 10 thereby increasing the height of the particle dispersion chamber 10. The extender portion 16E receives particles into its input aperture 16F from the exit aperture 16C of the particle dispersion chamber 10 and directs at least a portion thereof toward its exit aperture 16F. The extender portion may serve as the adapter for particle delivery to a user. Preferably, any of the adapters described below may be fitted to the extender portion 16E and positioned to receive particles from its exit aperture 16G for delivery to the user and/or surrounding environment. As shown in FIGS. 14, and 19, the dispersion chamber collar member 38 may be coupled to extender portion 16E thereby disposing the plenum space 36 between the dispersion chamber collar member 38 and the extender portion 16E.

In the embodiments shown in FIGS. 14, and 19, the compressed fluid outlets 14 are be formed in the extender portion 16E. The compressed fluid outlets 14 depicted include members 14A that extend between the channel 22 and the plenum space 36 through the extender portion 16E. The members 14A may include one or more inwardly extending portions 14B that extend into the particle dispersion chamber 10 or the extender portion 16E. The one or more inwardly extending portions 14A may be configured to direct the flow particles within the particle dispersion chamber 10. For example, the inwardly extending portions 14A may include aerodynamically shaped baffles or fins configured to impart the velocity vector pattern into the particle flow. The members 14A may be generally tube shaped having compressed fluid outlet channel 18 and its compressed fluid outlet orifice 20 formed therein.

With reference to FIGS. 7, 14, and 19, preferably, embodiments comprising one or more compressed fluid channels 18 and corresponding compressed fluid outlet orifices 20, additionally comprise at least one ambient air channel 24 and corresponding inner orifice 26A (also shown in FIGS. 2, 5B, and 12, which depict embodiments without the compressed fluid channels 18). Such embodiments may optionally comprise an outer housing 28 (see FIGS. 2, 6, and 7) having a wall 30 defining a plenum space 31 between the outer housing wall 30 and wall 16A of the particle dispersion chamber 10. The outer housing wall 30 has at least one opening 32 in communication with ambient air, such that the ambient air channel 24 and corresponding orifice 26B communicate with the at least one opening 32 by means of the plenum space 31. Preferably, there is a one-way valve 34 (see FIGS. 2 and 6) in operative association with the at least one opening 32 of the outer housing wall 30.

Filtering Member 21

The aerodynamic particle size filtering member 21, as described herein, is fundamentally different from prior art impactors or impaction baffles by virtue of its design and configuration and placement within or with respect to the atomization chamber 4 and primary orifice 7. According to preferred aspects, the aerodynamic member 21 functions as a particle size filter, by virtue of the fact that it is suitably positioned with respect to the fluid flow and particle flow along the projected axis "F," such that particles of desired size (e.g., 5 μm to 45 μm, 5 μm to 50 μm, 7.5 μm to 40 μm, or 10 μm to about 30 μm microns) follow the contour-directed fluid flow-stream and do not collide with the air-foil member surface, while larger particles (e.g., greater than about 60 μm) collide with the air-foil member surface and are returned by means of lateral re-directing means of the air-foil member to the holding means (e.g., liquid reservoir portion 6).

The instant aerodynamic filtering member 21 (e.g., air-foil members) fundamentally differs from prior art impaction/stagnation baffles (et orifice-proximate stagnation baffles) in that (i) a significant proportion of the atomized particles pass by the filtering member 21 in the deflected fluid flow stream without impacting the filtering member 21 providing for faster, more direct and efficient (less recycling, re-entrainment of liquid) particle delivery, and (ii) the filtering member 21 is sufficiently distanced (by distance "J") from the particle-generating orifices 7 and 17, such that while the larger particles collide with the air-foil and are redirected back to the holding means (e.g., liquid reservoir 6) for re-entrainment by the atomization means 11, they are not violently shattered into smaller particles (as in the case of prior art impaction baffles) so that the filtering member 21 serves as particle size filter and not as droplet-shattering stagnation baffle to provide respirable particles, thus providing for a broader size range of deliverable particles, including, in view of the inventive improved secondary liquid feed channel flow, particles from relatively viscous solutions not effectively handled by prior art devices.

The filter member 21 has a contoured surface (e.g., an aerodynamic surface contour) and is positioned at the distance "J" along the projected axis "F" from the primary orifice plane "P" to provide an aerodynamic fluid flow around the contoured surface. In the embodiment depicted in the figures, the distance "J" is greater than the distance "H." In particular embodiments, the distance "J" along the projected axis "F" from the primary orifice plane "P" is greater than or equal to 2×D1, 3×D1, 5×D1, 10×D1, 15×D1, 20×D1, 40×D1, or 50×D1.

According to preferred aspects, the configuration and positioning of the filter member 21 along the projected axis "F" operationally provides, depending on particle size and/or mass, for a proportion of atomized particles that collide with the member and a proportion of non-colliding particles (e.g., particles generated directly by the atomization means 11, and directed therefrom towards the delivery or open end 4A of the atomization chamber 4 but which do not collide with the filter member 21 by virtue of the relatively (compared to prior art) remote placement of the filter member 21 with respect to the primary compressed fluid orifice 7, and which non-colliding particles therefore do not depend on collisional generation or lateral redirection by an impaction or stagnation baffle element). Such aspects may additionally provide for non-colliding particles having paths near the surface of the particle filter that are carried in the aerodynamic fluid flow around the contoured surface of the filtering member 21.

Referring to FIG. 6, in some embodiments, the aerodynamic particle size filter member 21 is held at the distance "J" along the projected axis "F" by at least one filter support member 25 communicating with the wall 2A of the atomization chamber 4, the support member 25 is configured to operatively direct liquid accumulating on the filter member 21 away from the filter member for return to the liquid holding means. Preferably, there is a minimum number of such support members 25 to provide sufficient support, and they are minimally configured (e.g., one or a minimum number of thin/slender radial or spoke-like support elements) so that they minimally obstruct the particle flow path/volume, and minimally occlude the fluid and particle flow around the aerodynamic particle size filter member 21. In particular aspects the support members 25 are scalloped or otherwise contoured or slopped on the undersides 25A thereof, so as to direct liquid that accumulates on the filter member 21 back to the holding means (e.g., liquid reservoir 6) for re-entrainment by the atomization means 11.

For example, FIGS. 5A and 5B show a particle filter member 21 supported by three radial support arms 25. The support arms 25 support the filtering member 21 at its upper portion (compressed fluid orifice-distal portion), and have curved or scalloped undersides 25A (compressed fluid orifice-proximal surfaces) that direct liquid, generated by particle collisions on the contoured surface of the particle filter, laterally and downward to the holding means. In operation, the momentum of the colliding particles and the compressed fluid flow initially carries the resulting collisional liquid along the surface of the filter member 21, in a direction away from the atomization means 11, and further to the support arms 25 whereupon the liquid flow is redirected laterally by the contoured surface (curved undersides 25A) of the support arms 25, and in a direction generally towards the atomization means 11 and eventually to the holding means.

It will be appreciated by one of ordinary skill in the relevant art that a variety of support designs and configurations could be used to suitably support the filtering member 21, and provide collisional fluid redirecting means. For example, while three support arms 25 having curved or scallop undersides 25A are shown in the embodiment of FIGS. 5A and 5B, any number of support arms 25 (including just one arm) might be used, and such arms could have a variety of surface contours (e.g., angled, curved, grooved, ridged, convex, concave), and might be solid or alternatively comprised of sub-arm elements (e.g., multiple radial elements forming one, or each of a plurality of compound support arms). The essential aspect of such particle filter support means being that they suitably support the filtering member 21 at a distance of at least "H" from the compressed fluid orifice 7, and, at least preferably, provide collisional fluid redirecting means to return collisional fluid to the holding means for re-entrainment by the atomization means 11.

The support arms 25 of the filtering member 21 depicted in FIGS. 2, 5A, 5B, 6, 7, and 11 radiate outwardly from the filtering member 21, which is located near the center of the input opening 16B, in a substantially planar fashion like the spokes of a wheel. In other words, the support arms 25 may be substantially perpendicular to the wall 3 of the atomization chamber 4. In alternate embodiments, such as that depicted in FIGS. 12-14 and 18-19, the support arms 25 may extend upwardly or downwardly to support the filtering member 21 at a distance of at least "H" from the compressed fluid orifice 7. In other words, the support arms 25 may be at an angle other than substantially perpendicular with respect to the wall 3 of the atomization chamber 4. Further, the angle of the support arms 25 relative to the wall 3 of the atomization chamber may be adjustable.

Preferably, as shown in the embodiment of FIG. 11, the surface contour of the filtering member 21 is aerodynamic and provides for an aerodynamic flow of fluid around the contour. However, a variety of shapes and sizes of aerodynamic particle filters are encompassed. Preferably, the particle filter surface contour, and the configuration and positioning of the filtering member 21 along the projected axis "F" operationally provides (e.g., depending on particle size and/or mass) for a proportion of atomized particles that collide with the filtering member 21 and a proportion of non-colliding particles. Such non-colliding particles are particles that are generated directly by the atomization means 11 and directed therefrom towards the delivery end of the atomization chamber 4, but which do not collide with the filter member 21 by virtue the particle direction (velocity vector) and the relatively (compared to prior art) remote placement of the filtering member 21 with respect to the compressed fluid orifice 7. Such non-colliding particles therefore do not depend on collisional generation or lateral redirection by an impaction or stagnation baffle element. Preferred aerodynamic surface contour aspects additionally provide for non-colliding particles having paths near the surface of the filtering member 21 that escape collision with the filtering member 21 by virtue of being carried in the aerodynamic fluid flow around the surface of the filtering member 21.

Nasal Adapter 42

Certain embodiments, such as the atomizer embodiment 1 of, FIGS. 2 and 7, additionally comprise a nasal adapter 42 in fluid communication with the internal channel 22 (e.g., with the output opening 16C of the particle dispersion chamber 10) of the particle dispersion chamber 10 and thereby also in fluid communication with the atomization means 11 of atomization chamber 4. The nasal adapter 42 is configured to operatively receive, via the internal channel 22 and output opening 16C of the particle dispersion chamber 10, particles from the atomization means 11, and to sustain, and not disrupt, the particle flow or dispersion pattern generated within and exiting from the internal channel 22 of the particle dispersion chamber 10. In other words, the particles that exit the atomization means 11 first travel through the internal channel 22 where they are imparted with a predetermined flow pattern by the particle dispersion chamber 10, then the particles travel into the nasal adapter 42 where they are routed or channeled into the nostrils of the user without significant disruption of the predetermined flow pattern. As mentioned above, the extender portion 16E may be disposed between the nasal adapter 42 and the particle dispersion chamber 10. In such embodiments, the extender portion 16E may impart a predetermined particle flow pattern to the atomized particles or alternatively may simply allow at least a portion of the particles to flow from the particle dispersion chamber 10 to the nasal adapter 42 without significant disruption of the predetermined flow pattern imparted by the particle dispersion chamber 10.

Figure 8:
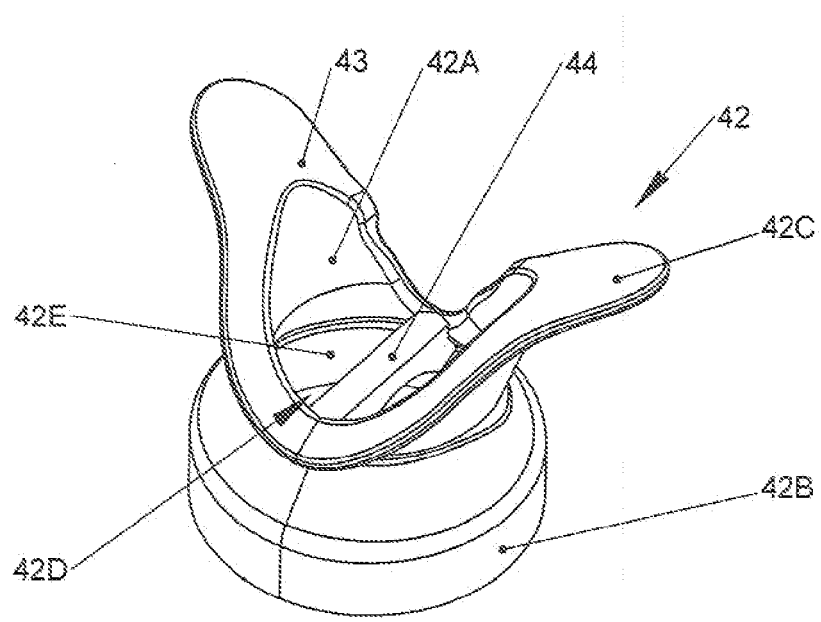
FIG. 8, shows, according to particular aspects of the present invention, a perspective view of an exemplary nasal adaptor embodiment.
Figure 9:
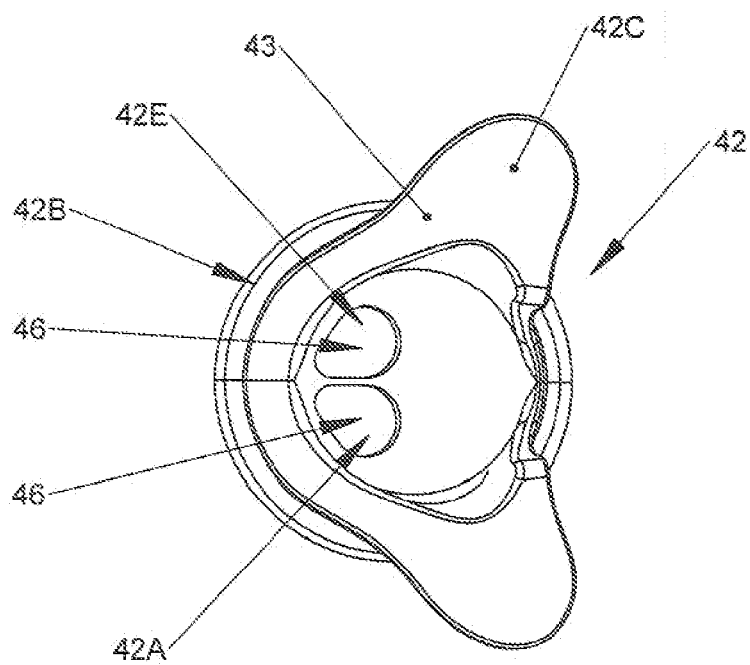
FIG. 9, shows, according to particular aspects of the present invention, a perspective view of another exemplary nasal adaptor embodiment.

For example, as shown in FIG. 7, the nasal adapter 42 communicates between the particle dispersion chamber 10 and the lower portion (base) of a user's nose (not shown). Turning to FIGS. 8 and 9, the nasal adapter 42 includes a first interface portion 42B and a second interface portion 42C. The nasal adapter 42 may include a channel portion 42A having an input aperture 42D formed in the first interface portion 42B and one or more exit apertures 42E formed in the second interface portion 42C.

In the embodiment shown in FIG. 7, the first interface portion 42B is configured to be coupled to the chamber wall 16 of the particle dispersion chamber 10 near its output opening 16C and to receive particles therefrom. In alternate embodiments, the first interface portion 42B is configured to be coupled to the extender portion 16E near its output opening 16G and to receive particles therefrom. In alternate embodiments, the nasal adapter 42 may include an integrally formed particle dispersion chamber (not shown) that performs substantially the same function(s) as the particle dispersion chamber 10. In such embodiments, the first interface portion 42B is configured to be coupled to the atomization chamber 4 and receives particles therefrom via the open portion 4A. In other words, the present invention includes embodiments in which the nasal adapter 42 and the particle dispersion chamber 10 are formed as a single unit and are coupled as a unit to the atomization chamber 4. Such a coupling may be effected using any method known in the art including using a connector such as a collar (not shown) substantially similar to the collar "C1," a collar "C2" (see FIG. 12 discussed below), and the like. Further, the filtering member 21 may be disposed between the nasal adapter 42 and open portion 4A of the atomization chamber 4.

The second interface portion 42C is configured to interface with the nostrils of the user and to deliver particles thereto via the exit aperture(s) 42E. Preferably, the second interface portion 42C of the nasal adapter 42 is anthropometrically designed to conform to a human nose and seal around the nasal tissue to prevent the escaping of particles/droplets, while simultaneously sustaining the imparted flow (e.g., 'vortical,' randomized or turbulent, etc., flow) for entry into the nasal aperture and subsequent penetration into the nasal cavity and targeted regions thereof. Preferably, the second interface portion 42C of the nasal adapter 42 is configured to conforms to the base of the nose. Preferably, the nasal adapter 42 provides a compact, portable, non-restrictive, non-invasive, easy to use device that provides a substantially conforming seal over a broad range of individual nose surface configurations to improve the efficiency of fluid, gas, or medicament delivery thereto, and to preclude leakage or improper delivery. The nasal adapter 42 provides for user comfort and suitable decorum in public use.

Turning to FIGS. 8 and 9, preferably, the nasal adapter 42 facilitates delivery of airborne particles to a user's nasal channels by providing for a temporary seal with the basal (underside) surface of the nose. It should be noted that FIGS. 8 and 9 depict two different exemplary embodiments of the nasal adapter 42. However, for illustrative purposes, like reference numerals have been used in these figures to identify identical or substantially identical structures. For example, the second interface portion 42C of the nasal adapter 42 is sized and structured to conform to the basal surfaces of the nose, sealing around the nostrils (nares) allowing deliverable gas, fluid, or medicament to travel to the nasal chambers and beyond with minimal leakage. In preferred embodiments, a contoured lip 43, located on or integral with the exit aperture(s) 42E of the channel portion 42A comes into contact with the tissue tracing the contours of the basal surface of the nose. The second interface portion 42C and lip 43 comprise a generally horizontal planar and deformable surface that is placed in sealed communication with the basal surface of the nose by application of upward pressure to hold the second interface portion 42C of the nasal adapter 42 against the basal surface of the nose. Preferably, the shape of the nasal adapter 42 is adaptable to a variety of different nose sizes and contours, and/or can be altered to fit noses of different sizes and contours. Sealing of the exit aperture(s) 42E of the second interface portion 42C of the nasal adapter 42 and the surrounding lip 43 to the basal surface of a user's nose is of significant utility. This aspect eliminates the difficulties associated with devices that completely cover or nearly completely cover the nose, or that are in contact with the internal mucous membranes of the nose.

Additionally, in preferred dual delivery channel embodiments, the lip 43 additionally sealably impinges on the columella nose base portion that runs between the nostrils, to provide for separate nostril delivery channels. Preferably, the nasal adapter 42 avoids the bulkiness and the possibility of infections associated with devices that are inserted into the nostrils, and allows for easy and comfortable communication with a small surface area of the nose to provide for relatively inconspicuous applications outside clinical settings. Preferred nasal adaptors are described in WO2004US0028874 (Pub. No. WO05023334A3; incorporated by reference herein in its entirety). In particular aspects, the nasal adapter 42, as shown in FIG. 8, may have a single divider 44 to help channel the particles (e.g., imparted droplet flow) into the appropriate nasal aperture. Alternatively, as shown in FIG. 9, the exit aperture(s) 42E of the nasal adapter 42 may include one or more, and preferably two, oriented openings 46, configured to channel the droplets/particles into a particular region of the naris plane (plane defined by the nasal opening), for example, the front part of the nasal apertures. Alternatively, oriented openings 46 are disposed at or near the rear of the second interface portion 42C to direct droplet/particle flow into the back part of the corresponding nasal apertures (closest to the lips).

According to particular aspects, such oriented openings 46 have substantial utility to more selectively target particle delivery within the nasal cavity, and regions thereof, of a user. For example, it has been shown that air that flows through a specific region of the nasal cavity originates at a specific location on the external naris plane (Zhao et al., *Chem. Senses*, 29:365-379, 2004; incorporated herein by reference in its entirety). For example, only air that enters the distal (ventral) tip of the nares reaches the olfactory region (Id; FIG. 7 at page 369). Therefore, nasal delivery using the inventive devices can be customizes with respect to left or right nostrils, and with respect to target regions within the respective nasal cavities, to provide for more precise and effective drug/agent targeting and delivery. Such embodiments comprising nasal adapters with, or in communication with oriented openings provide for additional olfactory utilities. For example, devices having oriented openings 46, configured to channel the droplets/particles into the front part of the naris plane have, according to additional inventive aspects, substantial utility for enhancing olfaction and effective olfactory sensitivity. For example, such embodiments have utility for facilitating olfaction of scented (e.g., perfume, fragrance, essential oil or cosmeceutical agent) and/or food and/or beverage (e.g., wine) products.

Nasal Adapter 60

FIGS. 13-17 depict a nasal adapter 60 configured for insertion into one or both nostrils of the user. The nasal adapter 60 includes a first interface portion 60B and at least one second interface portion 60C. The nasal adapter 60 may include a channel portion 60A having an input aperture 60D formed in the first interface portion 60B and one or more exit apertures 60E formed in each of the second interface portions 60C.

As is apparent to those of ordinary skill, the open portion 4A of the atomization chamber 4 may be larger than the nostril of the user. Consequently, as illustrated in FIGS. 13-15A and 16-17, the nasal adapter 60 configured for insertion into a single nostril may be generally cone or funnel shaped, tapering from the larger open portion 4A of the atomization chamber 4 to the smaller nostril of the user. However, as is appreciated by those of ordinary skill, the embodiments in which the open portion 4A of the atomization chamber 4 is substantially the same size or smaller than the nostril of the user are also within the scope of the present invention. Further, in embodiments in which the open portion 4A of the atomization chamber 4 is larger than the nostril of the user, the reduction in size from the first interface portion 60B to the second interface portion 60C need not be along a cone or equivalently tapered shape. Instead, any shape known in the art may be used, including a stepped-down shape, pyramidal shape, arbitrary shape, and the like.

In the embodiment depicted in FIGS. 13-15A and 16-17, the cone-shape of the nasal adapter 60 extends in a generally linear direction (e.g., the direction of the axis "F"). To use the nasal adapter 60, the user may hold his/her head in an upright position and insert the second interface portion 60C into his/her nostril.

In the embodiment shown in FIG. 14, the first interface portion 60B is configured to be coupled to the extender portion 16E near its output opening 16G and to receive particles therefrom. The nasal adapter 60 is in fluid communication with the internal channel 22 (e.g., with the output opening 16C of the particle dispersion chamber 10) of the particle dispersion chamber 10 via the extender portion 16E and is thereby also in fluid communication with the atomization means 11 of atomization chamber 4. The nasal adapter 60 is configured to operatively receive particles from the atomization means 11, and to sustain, and not disrupt, the particle flow or dispersion pattern of the particles received. In other words, the particles that exit the atomization means 11 first travel through the internal channel 22 where they are imparted with a predetermined flow pattern by the particle dispersion chamber 10, then the particles travel through the extender portion 16E and into the oral adapter 80 where they are routed or channeled into the nostril of the user without significant disruption of the predetermined flow pattern. After entering the nostril, the particles may be directed toward the user's nasal cavities for absorption into the body thereby, in a manner described above with respect to nasal adapter 42. The overall shape of the nasal adapter 60 and/or its exit aperture(s) 42E may be modified to selectively target particle delivery within the nasal cavity, and regions thereof, of a user, in a manner described above with respect to nasal adapter 42.

Figure 13:
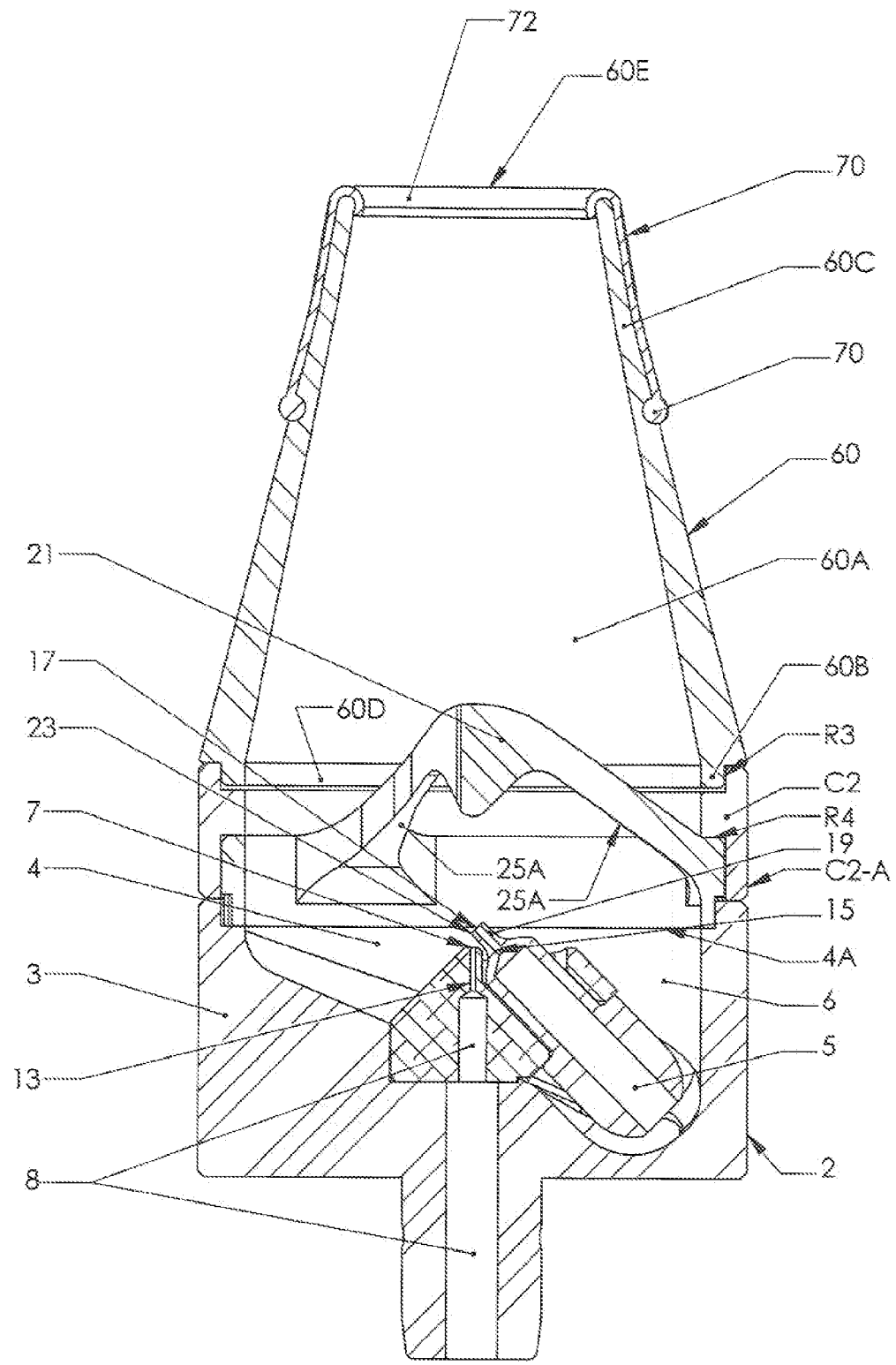
FIG. 13 shows, according to particular aspects of the present invention, a side cross sectional view of yet another exemplary nasal atomizer embodiment, comprising: atomization means; atomization chamber; aerodynamic particle size filtering means; and a nasal adapter having a second interface portion configured to be inserted into a nostril.

In alternate embodiments, such as the embodiment depicted in FIG. 13, the particle dispersion chamber 10 may be omitted. Alternatively, the nasal adapter 60 may include an integrally formed particle dispersion chamber (not shown) that performs substantially the same function(s) as the particle dispersion chamber 10. In such embodiments, the first interface portion 60B is configured to be coupled to the atomization chamber 4 and receives particles therefrom via the open portion 4A. In other words, the present invention includes embodiments in which the particle dispersion chamber 10 is omitted as well as embodiments in which the oral adapter 80 includes an integrally formed particle dispersion chamber 10. In such embodiments, the filtering member 21 may be disposed between the nasal adapter 60 and the open portion 4A of the atomization chamber 4.

In the embodiment depicted in FIG. 13, the connector or collar "C2" is disposed between the first interface portion 60B and the atomization chamber 4. The collar "C2" may include a recessed portion "R3" configured to receive the first interface portion 60B of the oral adapter 80 and position the input aperture 60D of the channel portion 60A adjacent to the open portion 4A formed in the top of the atomization chamber 4. The collar "C2" includes a recessed portion "R4" configured to receive a portion of the filtering member 21 and rest thereupon. The collar "C2" may also have a portion C2-A that rests upon an upper portion the wall 3 of the atomization chamber 4.

The second interface portion 60C is configured to interface with the nostril of the user and to deliver particles therein via the exit aperture(s) 60E. Preferably, the second interface portion 60C of the nasal adapter 60 is anthropometrically designed to fit inside a human nostril and to prevent adequately the escape of particles/droplets, while simultaneously sustaining the imparted flow (e.g., 'vortical,' randomized or turbulent, etc., flow) for entry into the nostril and subsequent penetration into the inside of the nasal cavity and targeted regions thereof.

As illustrated in FIG. 13, the nostril adapter 60 may include an optional sleeve 70 fitted over one or more of its second interface portions 60C. The sleeve 70 may include an aperture 72 located adjacent to the exit aperture(s) 60E for permitting the passage of particles/droplets therethrough. The sleeve 70 may be removable and reusable or disposable allowing the nasal adapter 60 to be used repeatedly between cleanings and/or replacement by simply replacing the sleeve 70 after one or more uses of the nasal adapter 60.

Figures 15A, 15B:
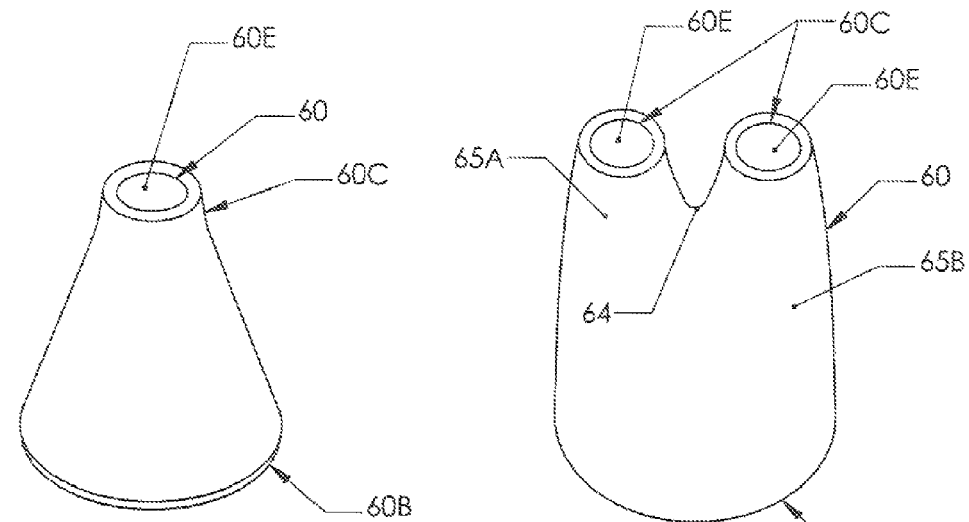
FIG. 15A shows, according to particular aspects of the present invention, an elevational perspective view of an exemplary embodiment of a nasal adapter having a second interface portion configured to be inserted into a nostril.
FIG. 15B shows, according to particular aspects of the present invention, an elevational perspective view of another exemplary embodiment of a nasal adapter configured for dual delivery and having a pair of second interface portions each configured to be inserted into one of the nostrils of a user.
Figure 16:
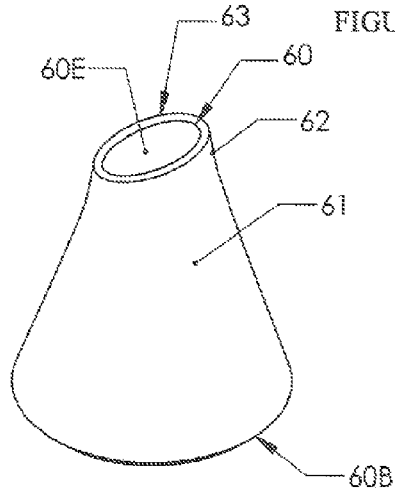
FIG. 16 shows, according to particular aspects of the present invention, an elevational perspective view of another exemplary embodiment of a nasal adapter having a second interface portion configured to be inserted into a nostril.
Figure 17:
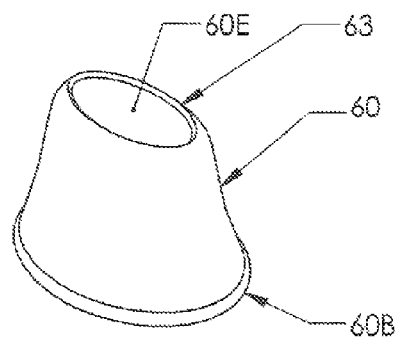
FIG. 17 shows, according to particular aspects of the present invention, an elevational perspective view of another exemplary embodiment of a nasal adapter having a second interface portion configured to be inserted into a nostril.
Figure 18:
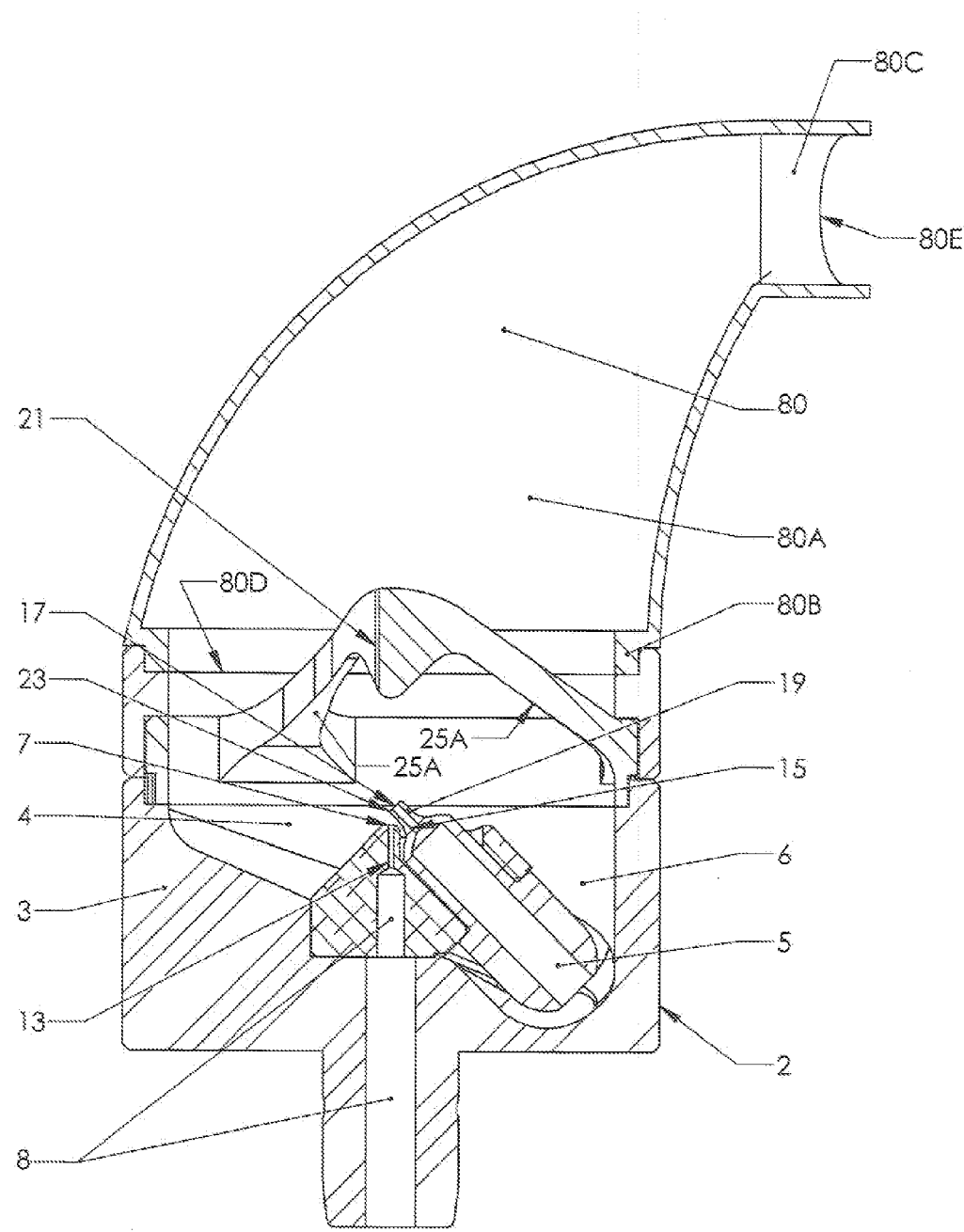
FIG. 18 shows, according to particular aspects of the present invention, a side cross sectional view of an exemplary oral atomizer embodiment, comprising: atomization means; atomization chamber; aerodynamic particle size filtering means; and an oral adapter.

FIGS. 15A and 16-17 provide several non-limiting examples of configurations of the nostril adapter 60 having a single second interface portion 60C. Each of these embodiments is configured to direct the particle flow to a particular selected area within the nasal cavity. FIG. 15 depicts a generally conically shaped nasal adapter 60 like that depicted in FIG. 13 (without the sleeve 70). The conically shaped nasal adapter 60 tapers along a generally linear direction (e.g., the direction of the axis "F") and includes a substantially centered single exit aperture 60E. FIG. 16 depicts a nasal adapter 60 having a substantially conically shaped portion 61 similar to that of the nasal adapter 60 depicted in FIG. 15. However, the second interface portion 60C of the nasal adapter 60 of FIG. 16 has an angled or bent portion 62 and a sloped upper portion 63 with a single exit aperture 16E formed therein. These structures may direct the particle flow toward a selected target area within the nostril and/or may make the nostril adapter 60 more comfortable to the user. The nasal adapter of FIG. 17 is somewhat cone-shaped and includes an off center exit aperture 60E as well as the sloped upper portion 63 with a single exit aperture 16E formed therein.

FIG. 15B depicts a nasal adapter 60 having a pair of second interface portions 60C, each configured to be inserted into one of the nostrils of the user. In other words, the nasal adapter 60 depicted in FIG. 15B is configured for dual delivery. The dual delivery nasal adapter 60 includes a portion 64 configured to receive a portion of the columella nose base portion that runs between the nostrils. The dual delivery nasal adapter 60 embodiment depicted includes a pair of substantially cone-shaped members 65A and 65B merged together below a location spaced from the exit aperture(s) 60E of each of the second interface portions 60C. The merged substantially cone-shaped members 65A and 65B define a continuous interior cavity (not shown) configured to receive particles from the extender portion 16E and/or the particle dispersion chamber 10. The portion 64 may be located between the substantially cone-shaped members 65A and 65B at the location where the substantially cone-shaped members 65A and 65B merge. The portion 64 may have general saddle-like shape.

With respect to each of the nasal adapters depicted in FIGS. 13-17, the exit aperture(s) 16E and/or second interface portion(s) 60C may be configured to selectively target particle delivery within the nasal cavity, and regions thereof, of a user in a manner identical to or similar to that discussed above with respect to the nasal adapter 42. The nasal adapter 60 may provide a compact, portable, non-restrictive, non-invasive, easy to use device that may be readily configured for a broad range of individual nostril configurations to improve the efficiency of fluid, gas, or medicament delivery thereto, and to preclude leakage or improper delivery. The nasal adapter 60 provides for user comfort and suitable decorum in public use.

Ocular Adapter 48

Figure 10:
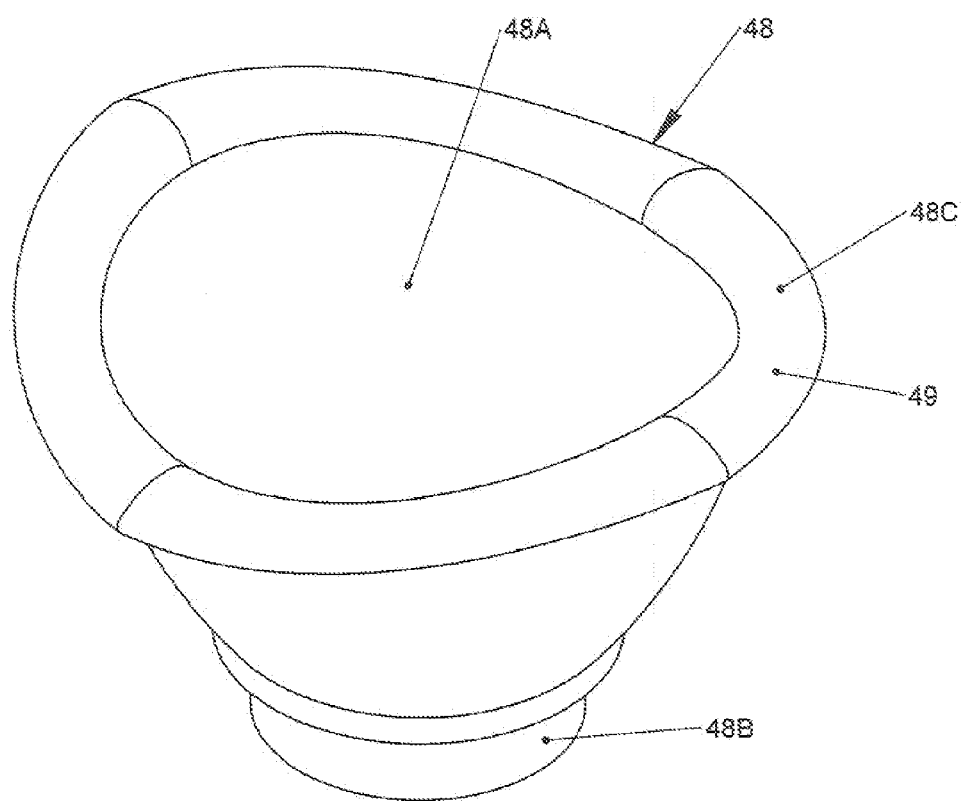
FIG. 10, shows, according to particular aspects of the present invention, a perspective view of an exemplary ocular adaptor embodiment.

As show in FIGS. 10 and 11, particular embodiments comprise an ocular adapter 48. The ocular adapter 48 is configured to operatively receive particles from the atomization means 11, and to sustain, and not disrupt, the particle flow or dispersion pattern generated within and exiting from the internal channel 22 of the particle dispersion chamber 10. In the embodiment depicted in the drawings, the particles that exit the atomization means 11 first travel through the internal channel 22 where they are imparted with a predetermined flow pattern by the particle dispersion chamber 10, then the particles travel into the ocular adapter 48 where they are routed or channeled onto the surface of the eye of the user without significant disruption of the predetermined flow pattern. The filtering member 21 may be disposed between the ocular adapter 48 and output opening 16C of the particle dispersion chamber 10. Optionally, the extender portion 16E may be disposed between the particle dispersion chamber 10 and the ocular adapter 48.

Like the nasal adapter 42, the ocular adapter 48 includes a first interface portion 48B and a second interface portion 48C. The ocular adapter 48 may include a channel portion 48A having an input aperture 48D formed in the first interface portion 48B and one or more outlet openings 48E formed in the second interface portion 48C.

The first interface portion 48B is configured to be coupled to the chamber wall 16 of the particle dispersion chamber 10 near its output opening 16C and to receive particles therefrom. In alternate embodiments, the ocular adapter 48 may include an integrally formed particle dispersion chamber (not shown) that performs substantially the same function(s) as the particle dispersion chamber 10. In such embodiments, the first interface portion 48B is configured to be coupled to the atomization chamber 4 and receives particles therefrom via the open portion 4A. In other words, the present invention includes embodiments in which the ocular adapter 48 and the particle dispersion chamber 10 are formed as a single unit and are coupled as a unit to the atomization chamber 4. Such a coupling may be effected using any method known in the art including using a connector such as a collar (not shown) substantially similar to the collar "C1," the collar "C2" (see FIG. 12 discussed below), and the like. In such embodiments, the filtering member 21 may be disposed between the ocular adapter 48 and open portion 4A of the atomization chamber 4.

The second interface portion 48C is configured to interface with the surface of the eye of the user and to deliver particles thereto via the outlet opening(s) 48E. Preferably, the second interface portion 48C of the ocular adapter 48 is anthropometrically designed to conform to a human eye socket and seal around the tissue or surfaces surrounding the eye to prevent the escaping of particles/droplets, while simultaneously sustaining the imparted flow (e.g., 'vortical,' randomized or turbulent, etc., flow) for delivery to the eye and/or targeted regions thereof.

Preferably, the second interface portion 48C of the ocular adapter 48 conforms to the facial portions surrounding the eye socket. Preferably, the ocular adapter 48 provides a compact, portable, non-restrictive, non-invasive, easy to use device that provides a good conforming seal over a broad range of individual eye socket surface configurations to improve the efficiency of fluid, gas, or medicament delivery thereto, and to preclude leakage or improper delivery. The ocular adapter 48 provides for user comfort and suitable decorum in public use. Preferably, the ocular adapter 48 facilitates delivery of airborne particles to a user's eye by providing for a temporary seal with the facial surfaces surrounding the eye.

For example, the second interface portion 48C of the ocular adapter 48 is sized and structured to conform to the surfaces around the eye allowing deliverable gas, fluid, or medicament to travel to the eye with minimal leakage. In preferred embodiments, a lip 49, located on or integral with the outlet opening(s) 48E of the chann the user's cheeks. Particles that encounter the inside of the cheeks of the user may be absorbed thereby.

In embodiments that include the oral adapter 80, the atomizer embodiment 1 may be "driven" by a compressed fluid originating from the compressed fluid source (not shown) and flowing through the primary compressed fluid channel 13. Alternatively, the user may "drive" the device by inhaling through the oral adapter 80 thereby drawing fluid inwardly through the primary compressed fluid channel 13. This fluid may encounter the liquid in the primary liquid feed channel 15 in a manner similar to that described above with respect to compressed gas supplied by the compressed gas source.

The oral adapter 80 may provide a compact, portable, non-restrictive, non-invasive, easy to use device that provides a substantially conforming seal over a broad range of individual mouth configurations to improve the efficiency of fluid, gas, or medicament delivery thereto, and to preclude leakage or improper delivery. The oral adapter 80 may also provide for user comfort and suitable decorum in public use.

Alternate Embodiment

Figure 22:
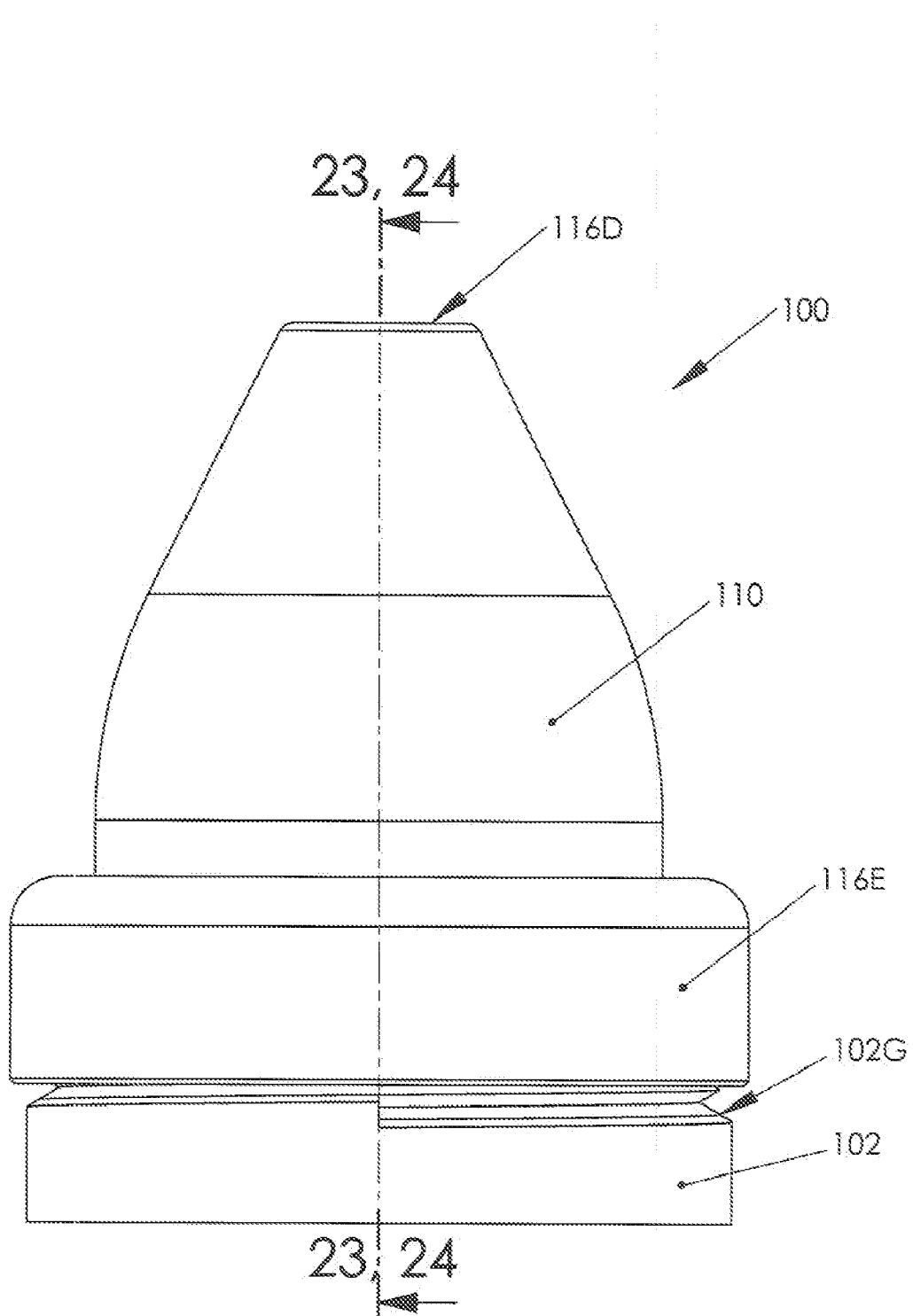
FIG. 22 shows, according to particular aspects of the present invention, a side view of another exemplary embodiment of a dispersion chamber and/or a delivery adapter (e.g., a dispersion chamber and/or a vicinity adapter for delivery of aerosolized particles to the vicinity of a user or to desired target surfaces (e.g., for delivery of perfume, fragrance, essential oil or cosmeceutical agent and the like)).
Figure 23:
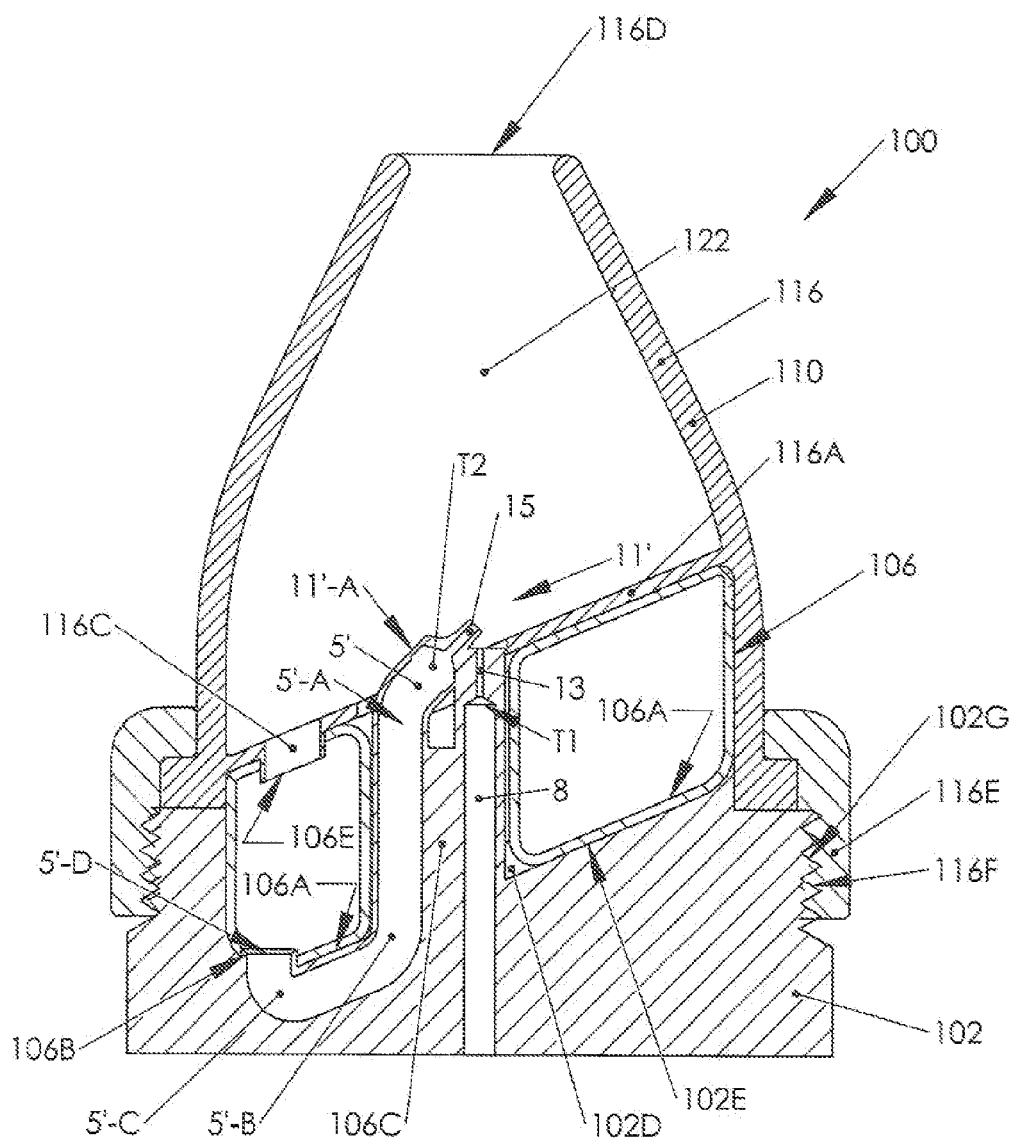
FIG. 23 shows, according to particular aspects of the present invention, a side cross-sectional view of an additional exemplary atomizer embodiment, comprising: atomization means; particle dispersion chamber and/or vicinity adapter; and angled removable (e.g., modular) liquid holding container with upper and lower apertures for liquid return and liquid entrainment, respectively.
Figure 24:
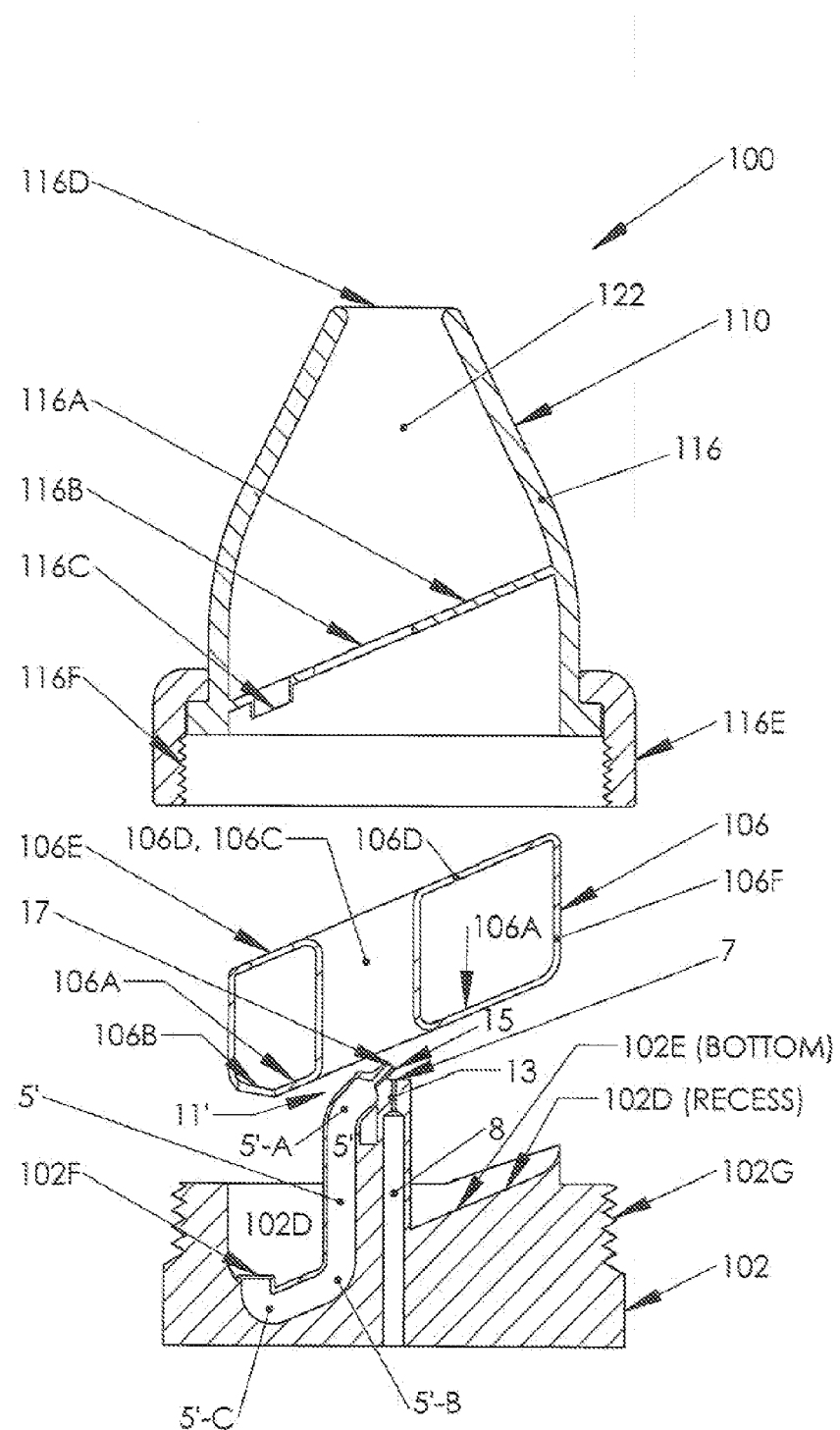
FIG. 24 shows a side elevational exploded sectional view of the exemplary embodiment of FIG. 23.

FIGS. 22-24 depict an alternate embodiment of the inventive atomizer, an atomizer 100, configured to deliver aerosolized particles into the atmosphere. The atomizer 100 includes an atomization housing 102 configured to house a portion of the component of the atomizer 100, such as the atomization means 11'. The atomization means 11' functions in substantially the same manner as atomization means 11 (described above). The atomization means 11' is substantially similar to the atomization means 11 described above and differs therefrom only with respect to the shape and positioning of its components. Like components have been identified with identical reference numerals. Only components that differ from those of the atomization means 11 are described in detail.

Unlike, the atomizer 1 described above, which includes the housing 2 having an atomization chamber 4 formed therein, the housing 102 includes a recessed portion 102D configured to receive the liquid holding means, such as an ampoule, a container 106, and the like, that may be at least partially filled with the liquid (not shown), such as a perfume, fragrance, essential oil or cosmeceutical agent, medicament, air freshener, insect repellent, insecticide, sanitizer, paint, and the like. The recessed portion 102D may circumscribe a portion of the atomization means 11'. A bottom surface 102E of the recessed portion 102D may be tapered toward an aperture 102F formed therein. The container 106, which is configured to be received inside the recessed portion 102D may have a hollow ring-like shaped housing 106F with a tapered bottom portion 106A that tapers toward an aperture 106B formed in tapered bottom portion 106A. The aperture 106B is juxtaposed with the aperture 102F formed in the recessed portion 102D when the container 106 is received therein. The tapered bottom portion 106A may cause the liquid stored inside the container 106 to flow toward the aperture 106B, through the aperture 106B, and into the aperture 102F. The container 106 has a tapered top portion 106D that tapers toward an aperture 106E formed in tapered top portion 106D. The tapered top portion 106D may be approximately parallel with the tapered bottom portion 106A.

In the embodiment depicted in the drawings, the container 106 has an open-ended channel 106C configured to receive a portion of the atomization means 11' when the container 106 is received inside the recessed portion 102D. A portion 11'-A of the atomization means 11' extends upwardly above the container 106.

The atomization means 11' includes a primary liquid feed channel 15 in communication with the liquid held in the container 106. The primary liquid feed channel 15 may receive the liquid from a secondary liquid feed channel 5' that is in fluid communication with the container 106. In other words, the secondary liquid feed channel 5' is intermediate between the primary liquid feed channel 15 and the container 106. The secondary liquid feed channel 5' differs from the secondary liquid feed channel 5 of the atomizer 1, which is generally linear in shape, in that the secondary liquid feed channel 5' includes one or more bent portions 5'-A, 5'-B, and 5'-C. The bent portions 5'-A, 5'-B, and 5'-C are configured to position an inlet 5'-D of the secondary liquid feed channel 5' in fluid communication with the aperture 106B of the container 106. Liquid exiting the container 106 is received into the secondary liquid feed channel 5' through the inlet 5'-D and is transported by the secondary liquid feed channel 5' up to the primary liquid feed channel 15 in the same manner liquid is transported by the secondary liquid feed channel 5 of the atomizer 1 (described above).

The atomization means 11' may be driven by a compressed fluid source (not shown). In such embodiments, the atomization means 11' includes a primary compressed fluid channel 13 in communication with an external or internal compressed fluid source (not shown). As described above, the primary compressed fluid channel 13 has the corresponding orifice 7 defining a projectable longitudinal compressed fluid feed channel axis "F," in operative communication with the primary liquid feed channel 15 and its corresponding orifice 17. The primary compressed fluid channel 13 receives compressed fluid from a secondary compressed fluid channel 8 in fluid communication with the compressed fluid source (not shown). In other words, the secondary compressed fluid channel 8 is intermediate between the primary compressed fluid channel 13 and a source of compressed fluid. The atomization means 11' is suitably configured to entrain a liquid in a fluid flow stream (not shown) to generate a particle (e.g., aerosolized liquid droplet) flow along (e.g., centered along) the projected axis "F."

Optionally, the atomizer 100 may include a combination atomization chamber and particle dispersion chamber 110 mounted to the housing 102. The chamber 110 is in fluid communication with the atomization means 11'. The portion 11'-A of the atomization means 11' may extend up into the chamber 110.

The chamber 110 may help define the particle size after the droplets are created by and received from the atomization means 11'. The chamber 110 includes a housing 116 having an internal laterally extending wall 116A. The wall 116A abuts the tapered top portion 106D of the container 106 when the chamber 110 is mounted to the housing 102. The wall 116A includes an opening 116B, configured to receive the portion 11'-A of the atomization means 11' and allow the portion 11'-A to extend into the chamber 110 thereby allowing the liquid stored in the container 106 to be atomized inside the chamber 110. The wall 116A includes a liquid return aperture 116C juxtaposed with the aperture 106E formed in tapered top portion 106D of the container 106. To reduce evaporation of the liquid housed inside the container 106, a one-way valve (not shown) or seal (not shown) may be disposed inside the liquid return aperture 116C and/or the aperture 106E. The wall 116A may taper toward the liquid return aperture 116C to encourage liquid on the wall 116A inside the chamber 110 to flow into the liquid return aperture 116C, through the aperture 106E, and into the container 106. Particles contacting the inside surface of the of the housing 116 may travel downward to the internal laterally extending wall 116A, flow down the wall 116A into the liquid return aperture 116C, flow through the aperture 116C into the aperture 106E, and finally return to the container 106 for re-atomization by the atomization means 11'.

The chamber 110 includes an atomization chamber-distal output opening 116D, and an internal particle dispersion channel 122 communicating between the portion 11'-A of the atomization means 11' and the output opening 116D. In some embodiments, the chamber 110 helps impart a velocity vector or flow pattern (e.g., 'vortical,' randomized, turbulent, etc. flow) to the aerosolized particles (e.g., atomized particles) received within and exiting from the chamber 110. Methods and structures for imparting a desired velocity vector or flow pattern are described above with respect to the particle dispersion chamber 10 and any methods or structures discussed above may be used with or incorporated into chamber 110.

The chamber 110 may include a connector portion 116E configured to operably couple the chamber 10 to the housing 102. In the embodiment depicted in the drawings, the housing 102 includes a threaded portion 102G formed along a portion of its outside surface. The connector portion 116E includes a threaded portion 116F configured for threaded engagement with the threaded portion 102G of the housing 102. The threaded portions 102G and 116F may be configured to position the liquid return aperture 116C adjacent to the aperture 106E formed in tapered top portion 106D when fully engaged with one another (i.e., the threaded connection between threaded portions 102G and 116F is tight). Alternatively, the chamber 10 may be coupled to the housing 102 by a collar (not shown) like the collar "C1" or its equivalent.

The atomizer 100 may optionally include the aerodynamic particle-size filtering means or filtering member 21 (e.g., air-foil member) suitably configured and positioned at a distance "J" from the primary orifice plane "P" to direct fluid flow around its contour, and thereby non-collisionally redirect particle flow of the desired particle size range around its contour, while simultaneously blocking larger particles for return to the container 106 and re-entrainment. As is apparent to those of ordinary skill in the art, the filtering member 21 may be installed inside the particle dispersion chamber 110 at distance "J" from the primary orifice plane "P." Particles filtered from the particle flow may travel down the inside surface of the housing 116, along the internal laterally extending wall 116A, into the liquid return aperture 116C, into the aperture 106E, and finally into the container 106.

The internal channel 122 of the chamber 110 may be configured so as to sustain, and not disrupt, the particle flow or dispersion pattern generated therein and exiting therefrom through the output opening 116D. Therefore, the internal channel 122 is, for example, cylindrical or substantially cylindrical (e.g., slightly tapered), smooth tapered cylindrical, etc., such that there are no abrupt discontinuities along the internal surface thereof, or surface structures or elements extending within the internal channel 122, or end caps, restrictions or elements that restrict the output opening 116D of the channel 122, that would disrupt the flow pattern imparted to the particles within the internal channel 122 and exiting the output opening 116D thereof.

As is apparent to those of ordinary skill, atomizers and nebulizers may be configured for use with various accessories, adapters, and the like and the atomizer 100 is not limited to use with any particular accessories, adapters, and the like. For example, using the techniques described herein, the nasal adapter 42 (or any adapter described herein) may be coupled to the chamber 110 and configured to receive atomized particles from output opening 116D.

Alternate Embodiment

Figure 25:
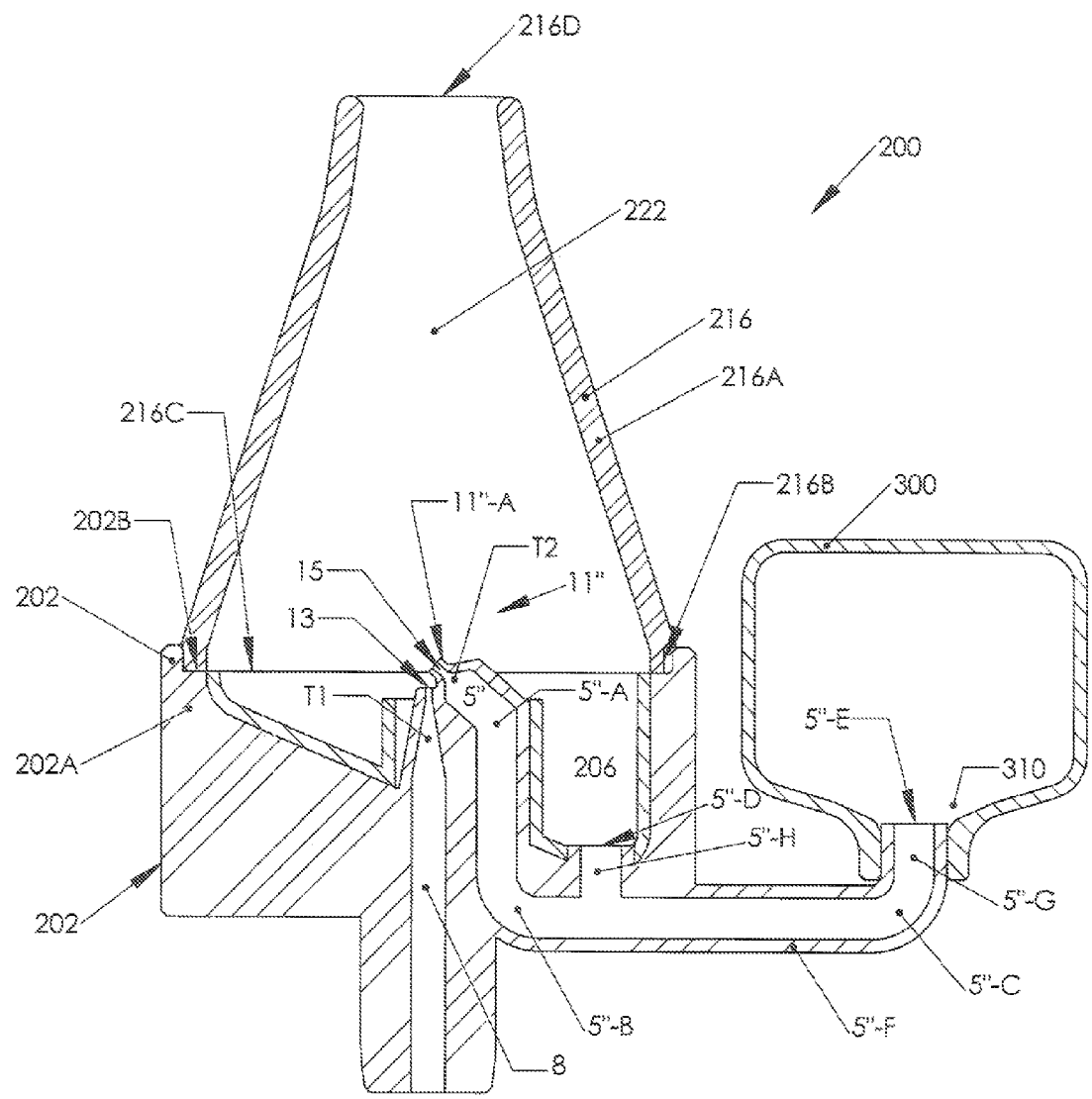
FIG. 25 shows, according to particular aspects of the present invention, a side cross-sectional view of an additional exemplary atomizer embodiment, comprising: atomization means; particle dispersion chamber and/or vicinity adapter; removable internal container, and external modular liquid holding container.
Figure 26:
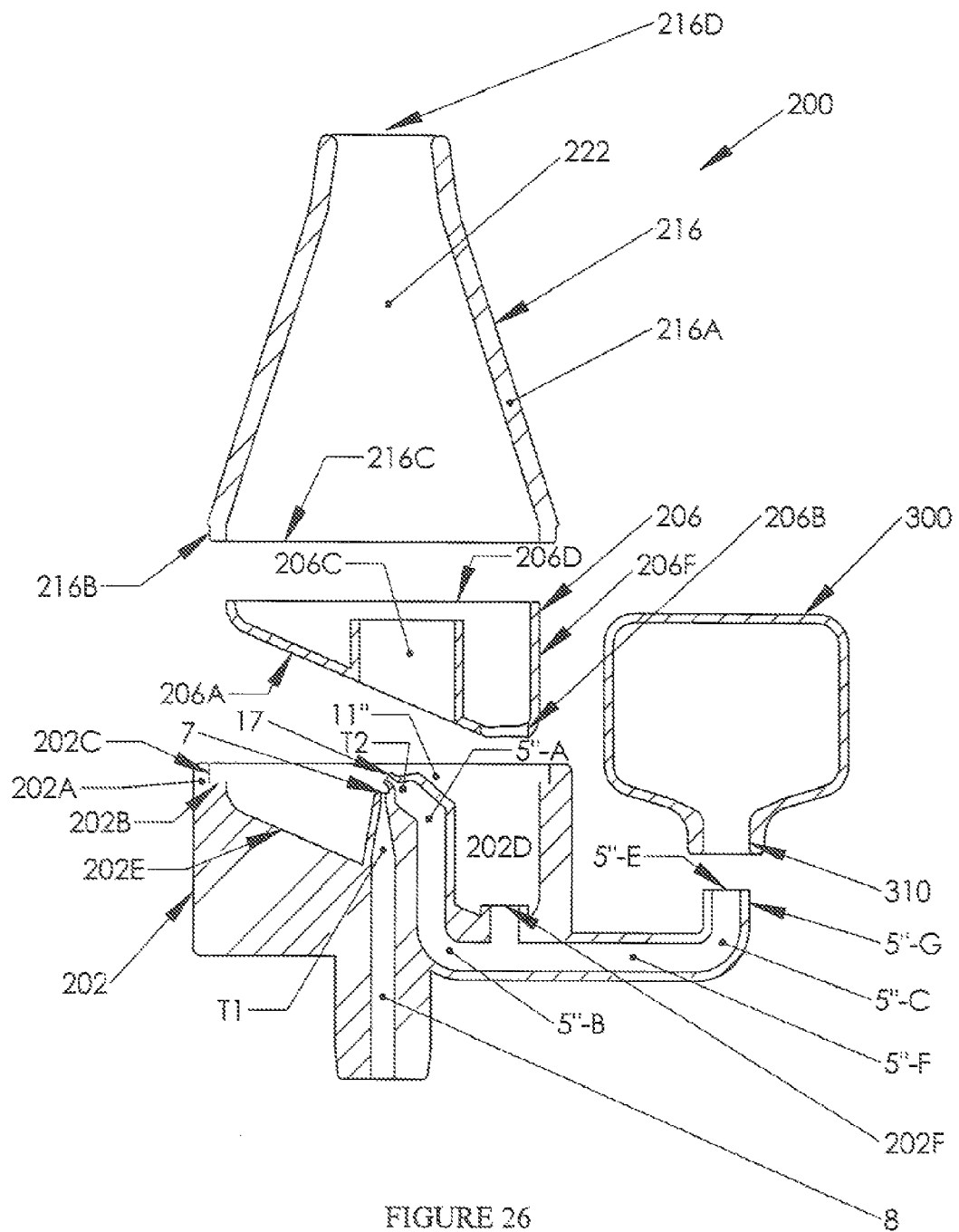
FIG. 26 shows a side elevational exploded sectional view of the exemplary embodiment of FIG. 25.

FIGS. 25-26 depict another alternate embodiment of the inventive atomizer, an atomizer 200, configured to deliver aerosolized particles into the atmosphere. The atomizer 200 includes an atomization housing 202 configured to house a portion of the component of the atomizer 200, such as the atomization means 11". The atomization means 11" functions in substantially the same manner as atomization means 11 (described above). The atomization means 11' is substantially similar to the atomization means 11 described above and differs therefrom only with respect to the shape and positioning of its components. Like components have been identified with identical reference numerals. Only components that differ from those of the atomization means 11 are described in detail.

Unlike, the atomizer 1 described above, which includes the housing 2 having an atomization chamber 4 formed therein, the housing 202 includes a recessed portion 202D configured to receive the liquid holding means, such as an ampoule, a container 206, and the like, that may be at least partially filled with the liquid (not shown), such as a perfume, fragrance, essential oil or cosmeceutical agent, medicament, air freshener, insect repellent, insecticide, sanitizer, and the like. The recessed portion 202D may circumscribe a portion of the atomization means 11". A bottom surface 202E of the recessed portion 202D may be tapered toward an aperture 202F formed therein. The container 206, which is configured to be received inside the recessed portion 202D may have a ring-like shaped housing 206F with a tapered bottom portion 206A that tapers toward an aperture 206B formed in tapered bottom portion 206A. The aperture 206B is juxtaposed with the aperture 202F formed in the recessed portion 202D when the container 206 is received therein. The tapered bottom portion 206A may cause the liquid stored inside the container 206 to flow toward the aperture 206B, through the aperture 206B, and into the aperture 202F. The exemplary container 206 has an open top portion 206D.

In the embodiment depicted in the drawings, the container 206 has an open-ended channel 206C configured to receive a portion of the atomization means 11" when the container 206 is received inside the recessed portion 202D. A portion 11"-A of the atomization means 11" extends upwardly above the container 206.

The atomization means 11" includes a primary liquid feed channel 15 in communication with the liquid held in the container 206. The primary liquid feed channel 15 may receive the liquid from a secondary liquid feed channel 5" that is in fluid communication with the container 206 and an external reservoir 300 such as an ampoule, a container, and the like. In other words, the secondary liquid feed channel 5" is intermediate between the primary liquid feed channel 15 and both the container 206 and the external reservoir 300.

The secondary liquid feed channel 5" differs from the secondary liquid feed channel 5 of the atomizer 1, which has a single inlet, in that the secondary liquid feed channel 5" has an inlet 5"-D in communication with the container 206 and an inlet 5"-E in communication the external reservoir 300. The secondary liquid feed channel 5" also includes a channel section 5"-H that branches from the majority portion of the secondary liquid feed channel 5" to position the inlet 5"-D in communication with the container 206. Further, a portion 5"-F of the secondary liquid feed channel 5" exits the housing 202 and extends laterally therefrom. The external reservoir 300 is mounted to a distal end portion 5"-G of the secondary liquid feed channel 5". The external reservoir 300 has an exit aperture 310 configured to supply the liquid to the inlet 5"-E.

The secondary liquid feed channel 5" also differs from the secondary liquid feed channel 5 of the atomizer 1, which is generally linear in shape, in that the secondary liquid feed channel 5' includes one or more bent portions 5"-A, 5"-B, and 5"-C. The bent portions 5"-A, 5"-B, and 5"-C are configured to position an inlet 5"-D of the secondary liquid feed channel 5" in fluid communication with the aperture 206B of the container 206 and inlet 5"-E in fluid communication with the external reservoir 300. Liquid received into the container 206 exits therefrom through the aperture 206B and enters into the secondary liquid feed channel 5" through the inlet 5"-D. Liquid housed in the external reservoir 300 exits therefrom through the exit aperture 310 and enters into the secondary liquid feed channel 5" through the inlet 5"-E. Liquid in the secondary liquid feed channel 5" is then transported by the secondary liquid feed channel 5" up to the primary liquid feed channel 15 in the same manner liquid is transported by the secondary liquid feed channel 5 of the atomizer 1 (described above).

The atomization means 11" may be driven by a compressed fluid source (not shown). In such embodiments, the atomization means 11" includes a primary compressed fluid channel 13' in communication with an external or internal compressed fluid source (not shown). As described above, the primary compressed fluid channel 13 has the corresponding orifice 7 defining a projectable longitudinal compressed fluid feed channel axis "F," in operative communication with the primary liquid feed channel 15 and its corresponding orifice 17. The primary compressed fluid channel 13 receives compressed fluid from a secondary compressed fluid channel 8 in fluid communication with the compressed fluid source (not shown). In other words, the secondary compressed fluid channel 8 is intermediate between the primary compressed fluid channel 13 and a source of compressed fluid. The atomization means 11" is suitably configured to entrain a liquid in a fluid flow stream (not shown) to generate a particle (e.g., aerosolized liquid droplet) flow along (e.g., centered along) the projected axis "F."

In the embodiments depicted in the figures, a tapered section is located between the primary and secondary channels of the atomization means 11, atomization means 11', and atomization means 11". In other words, a first tapered section T1 is located between the primary compressed fluid channel 13 and the secondary compressed fluid channel 8 and a second tapered section T2 is located between the primary liquid feed channel 15 and the secondary liquid feed channel 5. Similarly, the second tapered section T2 is located between the primary liquid feed channel 15 and the secondary liquid feed channel 5' and the second tapered section T2 is located between the primary liquid feed channel 15 and the secondary liquid feed channel 5". The lengths of each channel 13, 8, 15, and 5 may vary depending upon the application. Further, the length of the first tapered section T1 and the second tapered section T2 may also vary. In the embodiments depicted in the figures, the second tapered section T2 of the atomizer 200 is substantially larger than the second tapered section T2 of the other embodiments. Each of the first and second tapered sections T1 and T2 may taper along a linear path, an arcuate path, and a combination thereof. Further, embodiments in which the first tapered section T1 and/or the second tapered section T2 is omitted are within the scope of the present invention. Further, embodiments in which the first tapered section T1 extends all the way to the orifice 7 thereby omitting the primary compressed fluid channel 13 are within the scope of the present invention. Embodiments in which the second tapered section T2 extends all the way to the orifice 17 thereby omitting the primary liquid feed channel 15 are within the scope of the present invention.

Optionally, the atomizer 200 may include a combination atomization chamber and particle dispersion chamber 210 mounted to the housing 202. The chamber 210 is in fluid communication with the atomization means 11". The portion 11"-A of the atomization means 11" may extend up into the chamber 210.

The chamber 210 may help define the particle size after the droplets are created by and received from the atomization means 11". The housing 202 may include an upper portion 202A having a recessed portion 202B formed along the inside of the housing defining a lip 202C formed along the outside of the housing. The chamber 210 includes a housing 216 having an internal laterally extending wall 216A. The wall 216A has a lower portion 216B configured to be received inside the recessed portion 202B and maintained in place by the lip 202C when the chamber 210 is mounted to the housing 202.

The wall 216A includes an opening 216C, configured to receive the portion 11"-A of the atomization means 11" and allow the portion 11"-A to extend into the chamber 210 thereby allowing the liquid stored in the container 206 and/or external reservoir 300 to be atomized inside the chamber 210. Particles contacting the inside surface of the of the housing 216 may travel down the wall 216A and into the container 206. As mention above, liquid in the container 206 may exit therefrom through the aperture 206B into the secondary liquid feed channel 5" for re-atomization by the atomization means 11".

The chamber 210 includes an atomization chamber-distal output opening 216D, and an internal particle dispersion channel 222 communicating between the portion 11"-A of the atomization means 11" and the output opening 216D. In some embodiments, the chamber 210 helps impart a velocity vector or flow pattern (e.g., 'vortical,' randomized, turbulent, etc. flow) to the aerosolized particles (e.g., atomized particles) received within and exiting from the chamber 210. Methods and structures for imparting a desired velocity vector or flow pattern are described above with respect to the particle dispersion chamber 10 and any methods or structures discussed above may be used with or incorporated into chamber 210.

The atomizer 200 may optionally include the aerodynamic particle-size filtering means or filtering member 21 (e.g., air-foil member) suitably configured and positioned at a distance "J" from the primary orifice plane "P" to direct fluid flow around its contour, and thereby non-collisionally redirect particle flow of the desired particle size range around its contour, while simultaneously blocking larger particles for return to the container 206 and re-entrainment. As is apparent to those of ordinary skill in the art, the filtering member 21 may be installed inside the particle dispersion chamber 210 at distance "J" from the primary orifice plane "P." Particles filtered from the particle flow may travel down the inside surface of the housing 216, along the internal laterally extending wall 216A and into the container 206.

The internal channel 222 of the chamber 210 may be configured so as to sustain, and not disrupt, the particle flow or dispersion pattern generated therein and exiting therefrom through the output opening 216D. Therefore, the internal channel 222 is, for example, cylindrical or substantially cylindrical (e.g., slightly tapered), smooth tapered cylindrical, etc., such that there are no abrupt discontinuities along the internal surface thereof, or surface structures or elements extending within the internal channel 222, or end caps, restrictions or elements that restrict the output opening 216D of the channel 222, that would disrupt the flow pattern imparted to the particles within the internal channel 222 and exiting the output opening 216D thereof.

As is apparent to those of ordinary skill, atomizers and nebulizers may be configured for use with various accessories, adapters, and the like and the atomizer 200 is not limited to use with any particular accessories, adapters, and the like. For example, using the techniques described herein, the nasal adapter 42 (or any adapter described herein) may be coupled to the chamber 210 and configured to receive atomized particles from output opening 216D.

Particle Size

As shown in exemplary FIGS. 2-21, the inventive atomization devices provide a variable configuration that allows for generating particles suitable to target, for example, specific areas of the nasal cavity. In particular aspects, the variable configuration is associated with the compressed fluid channel 8 and the liquid/solution feed channel 15. For example, in particular embodiments, the adjustment of at least one of "D1," "D2," "D3," "D4," "D5," "L1," "L2," "L3," "L4," "O," "S," "A," "H" and "J" allow for highly efficient generation of particles with, for example, a MMAD of between about 10 and about 30 microns, and even with solutions having relatively high viscosity (e.g., up to about 80, or to about 105 centipoise).

In particular aspects, the delivered atomized particles are comprised of particles substantially having a mean diameter of, e.g., 5 μm to 45 μm, 5 μm to 50 μm, 7.5 μm to 40 μm, or 10 μm to about 30 μm microns. Typically, for example, about 10 μm to about 30 μm. In some embodiments, the delivered particles are comprised of particles substantially having a mean diameter of about 10 μm to about 15 μm (e.g., for optimal targeting the olfactory region and the paranasal sinuses). In other embodiments, the delivered particles are comprised of particles substantially having a mean diameter of about 15 μm to about 30 μm (e.g., for targeting the overall nasal cavity).

According to further aspects, particle size can be varied, and is determined by several factors (in addition to the pressure and or volume of compressed fluid flow) including: the length ("L1" and "L2") and internal diameter (e.g., "D1" and "D2") of the primary compressed fluid feed 13 and primary liquid feed 15 channels and corresponding orifices 7 and 17, respectively; the outer diameter ("D3") of the primary liquid feed channel at the orifice end (i.e., the outside diameter of the primary liquid feed channel end wall face 23); the diameter D4 and length L3 of the secondary liquid feed channel 5; the distance "H" from the primary liquid feed channel end wall face 23 to the primary orifice plane "P" (defined by the primary orifice 7); the angle A of approach between the liquid feed channel axis "L" and the compressed fluid feed channel axis "F"; the selected distance S, as defined herein; the 'offset' distance O, as defined herein; the distance "J" as defined herein between the particle size filtering member and the primary orifice plane "P"; and the physical characteristics of the liquid, such as, surface tension, viscosity, density, etc. Additionally, the design, configuration and spatial placement of the particle size filtering member or 'splitter' and the design (e.g., length, taper, etc) of the dispersion chamber contribute to the particle size.

TABLE 1 illustrates data showing device performance when the nozzle diameter and feed pin angle are changed. The first data set is a 40 degree droplet generator where the nozzle diameter is varied from 0.012 to 0.015 to 0.0165. The second data set is a group of 0.012 nozzles with the feed pin angle varied from 40 to 60 degrees in 5 degree intervals.

Therefore, according to particular aspects of the present invention, how configurational variables can be adjusted to obtain tailored particle sizes. Similarly, Applicants have shown that: as the inner diameter of the feed pin increases the atomization rate and droplet sizes increase; as the height of the feed pin tip increases the atomization rate decreases; and as the air pressure in the nozzle increase the atomization rate increases and droplet sizes decrease. Therefore the inventive devices offer a substantial improvement in the ability to generate a broad range of particle sizes.

TABLE 1

Data showing device performance when the nozzle diameter and feed pin angle are changed.

| | Rate (g/min) | Dv(50) (microns) |
|---|---|---|
| 40 Degree Setup Nozzle D (in) | | |
| 0.0120 | 0.58 | 16.4 |
| 0.0150 | 0.74 | 19.3 |
| 0.0165 | 0.84 | 22.0 |
| 0.0120 Nozzle Angle (Degrees) | | |
| 40 | 0.58 | 16.44 |
| 45 | 0.63 | 16.73 |
| 50 | 0.57 | 15.10 |
| 55 | 0.84 | 19.12 |
| 60 | 0.86 | 29.55 |

In preferred aspects, the inventive integrated devices provide appropriately sized particle distributions having suitable dynamic outflow properties to target specific areas, such as in the nasal cavity and particular regions thereof, such as the paranasal sinuses, or for ocular delivery.

Preferably, the fluid is air or another suitable compressible gas, or combinations thereof. According to preferred aspects of the present invention, the delivered nebulized particles are comprised of particles substantially having a mean diameter of about 2 to about 50 μm, about 5 to about 50 μm, about 5 to about 40 μm, about 5 to about 35 μm, about 5 to about 30 μm, about 5 to about 20 μm, about 5 to about 17 μm, about 5 to about 15 μm, about 8 to about 30 μm, about 8 to about 25 μm, about 8 to about 20 μm, about 10 to about 30 μm, about 10 to about 25 μm, about 10 to about 20 μm, about 10 to about 17 μm, about 10 to about 15 μm, about 11 to about 40 μm, about 11 to about 30 μm, about 11 to about 20 μm, about 11 to about 15 μm, about 12 to about 17 μm, about 15 to about 25 μm, about 15 to about 20 μm, and about 17 to about 23 μm. Preferably, the delivered nebulized particles are comprised of particles substantially having a mean diameter of about 5 to about 30 μm, about 8 to about 25 μm, about 10 to about 20 μm, about 10 to about 17 μm, about 10 to about 15 μm, and about 12 to about 17 μm. Preferably, the delivered nebulized particles are comprised of particles substantially having a mean diameter of about 8 to about 25 μm, about 10 to about 15 μm, or about 12 to about 15 μm.

Improved Performance Over the Prior Art

The follow is a discussion comparing the instant devices to those of the prior art in terms of: (A) configurational and operational differences; (B) atomization rates; and (C) efficiency of delivery to, and retention by, the delivery target.

(A). Configurational and Operational Differences:

The instant novel atomization devices differ from prior art nebulization and atomization devices in at least nine fundamental ways that give rise to substantially improved performance and utility. However, as is apparent to those of ordinary skill in the art, particular embodiments of the devices may not include all of these enumerated differences. Further, additional differences beyond those discussed herein exist that distinguish one or more of these novel devices from the prior art.

First, the configuration of the atomization means is unique, in that: the primary compressed fluid channel orifice 7 and the primary liquid channel orifice 17 are separated by at least a distance "H" along the projected longitudinal axis "F" of the primary compressed fluid feed channel 13; and the respective projected axes "F" and "L" of the fluid and liquid channels intersect at the angle "A" (e.g., right, or oblique including acute or obtuse). Preferably, the angle "A" is acute. Moreover, in preferred embodiments, at the distance "H", the plane "I"-intersecting portion 23B of the perimeter 23A of the end-wall face 23 is positioned within a selected or selectable distance "S" from the projected longitudinal axis "F" that is less than or equal to diameter "D1" or less than or equal to ½×D1. This configuration not only affords a high rate of particle generation, but also affords generation of a broad range of desired MMAD particle size ranges, without the need for prior art impaction/stagnation baffles to violently shatter the particles providing a relatively limited MMAD particle size range.

Second, in preferred embodiments, the instant devices comprise a particle filtering member 21 (e.g., an aerodynamic member, for example, an air-foil member) that serves as a particle size filter by non-collisionally redirecting flow of the desired particle size range around its contour while simultaneously blocking larger particles, providing an aerosolized particle filter function that does not rely on impaction or stagnation baffles to violently shatter impacting droplets into the desired particle size range. This feature affords the ability to provide for a much broader range of MMAD particle size ranges (e.g., not just the limited ranges attainable using impaction/shattering) by means of appropriate design and spatial configuring of the air-foil member with respect to the atomization means.

Third, because of the inventive positioning of the air-foil or filtering member 21 relative to the atomization means 11, while larger particles collide with the filtering member 21, a significant proportion of the desired size of atomized particles do not collide with the filtering member 21, and rather follow a non-colliding slightly redirected particle flow path along the contour of the filtering member 21. This feature results in relatively faster delivery of the desired particles because they are directed in non-collisional paths toward the user (no collision, shattering and transverse re-direction as with prior art impaction/stagnation baffles).

Fourth, in preferred embodiments of the instant devices, the primary liquid feed channel 15 communicates with the liquid to be nebulized (e.g., in the liquid holding portion of the atomization chamber 4) via an intermediate secondary liquid feed channel 5 (see in more detail below) that is has significantly better flow properties (e.g., larger channel diameter "D4," resulting in less drag) than corresponding secondary liquid feed channels of prior art nebulizers and atomizers, which are relatively constricted (e.g., narrow, with high surface area to cross-section ratios). This affords a substantial improvement over prior art devices, in that the instant devices are capable of generating particles from liquids that are significantly more (e.g., 20-30 times more) viscous than can be handled by prior art devices.

Fifth, preferred embodiments of the instant devices comprise a particle dispersion chamber 10 having a chamber wall 16 and having an input opening 16B and an output opening 16C with an internal channel 22 therebetween, the input opening 16B in fluid communication with the atomization means 11, the dispersion chamber 10 having at least one directed fluid output 20, 26 operative to impart a fluid flow pattern to aerosolized particles received within and exiting the dispersion chamber output opening 16C. By imparting an appropriate flow pattern (e.g., 'vortical,' turbulent, randomized, etc.), the particle dispersion chamber 10 provides not only for more effective delivery of aerosolized particles, but for effective targeted delivery of the suitably dispersed particles.

Sixth, preferred embodiments of the instant devices comprise not only comprise a nasal 42, 60, and oral adapters 80, that directs particle flow to the respective delivery cavity while preserving the particle flow dynamics (e.g., vortical, turbulent, or randomized flow pattern), but also provide nasal adapters having oriented openings disposed within the adapter (e.g., at or near the front or rear of the nose piece) to direct droplet/particle flows into, for example, the front or back part of the nasal aperture (e.g., farthest from, or closest to the lips), or laterally to the cheeks (oral adapter oriented openings). According to additionally preferred aspects, such oriented openings provide substantial additional means to target particle delivery within the nasal and oral cavities of a user.

Seventh, particular embodiments comprise the nasal adapter 60 having numerous single flow embodiments as well as dual flow embodiments. The nasal adapter 60 directs particle flow to the nasal cavity while preserving the particle flow dynamics (e.g., vortical, turbulent, or randomized flow pattern). The exit aperture(s) 60E of the second interface portion(s) 60C of the nasal adapter 60 may be configured to direct droplet/particle flows into, for example, the front or back part of the nasal aperture (e.g., farthest from, or closest to the lips). According to additionally preferred aspects, such oriented openings provide substantial additional means to target particle delivery within the nasal cavity of a user.

Eighth, particular embodiments comprise the ocular adapter 48 to facilitate ocular delivery of aerosolized particles. For the first time, such embodiments provide for effective targeted delivery of aerosolized particles (e.g., medicament-containing aerosolized particles) to a user's eye.

Ninth, particular embodiments comprise the oral adapter 80 to facilitate oral delivery of aerosolized particles. For the first time, such embodiments provide for effective targeted delivery of aerosolized particles (e.g., medicament-containing aerosolized particles) to a user's mouth including the inside surfaces of the cheeks.

(B) Substantially Enhanced Atomization Rate Over the Prior Art:

The atomizer technology described herein may be configured to produce significantly higher atomization rates and/or efficiencies than prior art jet style atomizers. Without being limited by theory, it is believed that atomization of the liquid (including higher viscosity liquids) occurs for two primary reasons.

First, the atomized particles or droplets generated travel in a relatively narrow particle stream directed at the nasal opening(s) of the user. In contrast, prior art jet style nebulizers, by virtue of the impactor element, project droplets laterally in a radial path shaped much like an umbrella. Therefore, the droplets that are not collisionally absorbed on the sides of the atomization chamber must change direction converge before they can be delivered to, the user. Unfortunately, only a small percentage of the droplets avoid impacting the inner wall(s) of the jet style nebulizer to be redirected to the user. Because the droplets of the inventive technology are created by an atomization means that produces a linear droplet stream, the drops produced do not need to change direction before exiting the atomizer causing fewer droplets to contact the inner wall(s) thereby allowing more droplets to exit the device, increasing the atomization rate and delivery efficiency substantially.

Second, the flow path of the liquid from the reservoir(s) to the point of droplet generation (e.g., atomization means 11) in the inventive technology is significantly less restrictive than that of prior art jet style nebulizers. In general, atomization rate, or mass flow rate, may be determined by at least three factors: (1) the physical properties of the liquid; (2) the vacuum pressure created from the venturi effect; and (3) the flow path of the liquid. Therefore, to provide an accurate comparison of the present technology and jet style nebulizers, the same liquid and vacuum pressures should be used. Thus, differences in mass flow rate may be attributed to differences in the liquid flow paths of the devices.

The flow path of the liquid from the reservoir(s) to the point of droplet generation (e.g., atomization means 11) in the inventive technology differs from that of the prior art jet nebulizers in at least two respects. First, the cross-sectional area of one or more portions of the flow path of the instant devices is/are larger than corresponding portion of the flow path in prior art nebulizers. Increasing the cross-sectional area of the flow path, or portions thereof increases mass flow rate. For example, the cross-sectional area of the secondary liquid feed channel 5" is considerably larger than corresponding liquid feed channels found in prior art nebulizers. Second, the flow path of the liquid in the inventive technology has less internal surface area than the flow path found in prior art nebulizers. In other words, the amount of channel surface engaged by the liquid as it travels from the reservoir to the atomization means is less in the inventive technology than is found in the prior art. As a fluid flows over a surface, flow of the fluid is restricted by shear forces between the fluid and the surface. The liquid flow path of a typical prior art jet nebulizer, for example, has approximately three times more surface area than the inventive technology. Therefore, the flow path of a jet nebulizer is three times more restrictive. Therefore, a linear style atomizer having a liquid flow path with a larger cross-sectional area and less adjacent surface area is capable of a higher mass flow rate as well as providing for atomizing liquids having substantially higher viscosities.

The following TABLE 2 provides data obtained by Applicants comparing the flow rate of the inventive linear nebulizer with a representative prior art jet nebulizer.

TABLE 2

Comparison of flow rate between prior art nebulizer and an exemplary inventive atomizer, and where comparisons are made with liquids of different viscosity.

| Viscosity (centipoise) | Jet Nebulizer (grams per minute of inhalation) | Linear Atomizer (grams per minute of inhalation) |
| --- | --- | --- |
| 1 | 0.13 | 0.42 |
| 5 | 0.06 | 0.4 |
| 10 | 0 | 0.35 |
| 20 | 0 | 0.3 |

TABLE 2-continued

Comparison of flow rate between prior art nebulizer and an exemplary inventive atomizer, and where comparisons are made with liquids of different viscosity.

| Viscosity (centipoise) | Jet Nebulizer (grams per minute of inhalation) | Linear Atomizer (grams per minute of inhalation) |
| --- | --- | --- |
| 40 | 0 | 0.26 |
| 60 | 0 | 0.22 |
| 80 | 0 | 0.18 |
| 100 | 0 | 0.14 |

Therefore, not only is the flow rate of the instant inventive atomizer over three times greater than that of the prior art jet nebulizer, but the instant devices can also deliver fluids having viscosities up to 100 centipoise or greater.

(C). Substantially Enhanced Efficiency of Delivery to, and Retention by, the Delivery Target:

The instant devices provide for delivery of multiple optimized boluses to provide for substantially enhanced delivery to and retention by the delivery target surfaces.

Prior art spray bottles, for example are typically used to deliver a maximum dose of 1 or 2 boluses of about 0.10 ml per nostril (more boluses cannot typically be delivered because of saturation of the delivery target and 'run-off'. That is, for a variety of reasons among which is the fact the predominant mass of delivered liquid comprises drops of relatively large size that collide with the target surface, exceed the saturation point of the tissues and immediately fall off the tissues and drain/run out the nose. In this situation, most of the delivered agent or drug is actually wasted. In simplistic terms, use of prior art spray bottles is like throwing 'water balloons' of paint against at wall, as opposed to spray painting the wall.

By contrast, the instant devices allow for delivery more than 2, and normally 8 to 15 boluses of droplets each of which may have about 0.01 ml of drug, or a greater amount. Because of the optimal size and more extensive and uniform penetration of the droplets, the droplets are layered on the tissue multiple times (through multiple inspirations), each droplet finding a surface space that is not yet saturated for deposition (like evenly spray painting a wall without 'running' of the paint). In preferred embodiments, the droplet size is optimized to provide for delivery of 0.10 ml of drug (per nostril) over 8 to 15 inhalation cycles.

Therefore, with respect to the total amount of drug delivered to the nasal cavity, spray bottles, based on the concept above (and as widely recognized in the art), maximally deliver about 0.40 ml (two bolus sprays of 0.10 ml per nostril). With two nostrils you get the 0.4 ml. By contrast, because the instant devices do not have the 'splatter' effect with immediate saturation and run off, the instant devices can in fact deliver much more, depending on the number of inhalation cycles used. Applicants have, for example, determined that the instant devices are capable of delivering as much as 1 to 1.5 ml without run-off. According to particular aspects, this has substantial and important consequences for drug delivery, and particularly for systemic delivery. The ability to deliver an increase volume of liquid provides for formulations to move from a suspension to a solution, based on solubility of the active ingredient. Additionally, this capability provides for administration of combinations of drugs which previously could not be combined for delivery due to the requirement to formulate them in a smaller 0.1 ml spray. According to preferred aspects, with the instant devices relative to the prior art devices, more drug over a larger surface provides for substantially more effective topical treatment, as well as greater systemic absorption.

Nasal mucosa absorption. While not being bound by mechanism, and as recognized in the art, it is not surprising that a formulated volume of more than 0.40 ml could be deposited in the nasal cavities. Generally speaking, while the amount and distribution of hygroscopic material on the surface of the nasal mucosa is difficult to precisely determine and will depend, at least to some extent on the particular location and time (nasal status). For example, the amount of hygroscopic material may depend on how a person was breathing (e.g., in/out through the mouth, or through the nose). It may additionally depend upon the atmospheric temperature and moisture content, on the composition and amount of surface secretions of the nose and their 'age' since secretion, and on how these secretions have been transported across the nasal surface and thus the regional thickness thereof.

Practically speaking, however, and despite the imprecise characterization generally available for a particular nasal mucosa regions, the dynamics of the hydration of the mucosa are likely very significant in determining the amount of delivery volume that can be absorbed. A coarse nasal spray, for example, will deliver a quantity of large droplets on the surface that will not rapidly be incorporated into the depths or evenly distribute over the surrounding surface. Rather, the surface becomes locally overburdened, resulting in and run-off. By contrast, by delivering a finer spray, local absorption characteristics will be improved (no immediate saturation) and the surface will be more uniformly covered relative to the use of larger drops. Additionally, with smaller drops there is a much greater contact area per unit mass of drop beneath it and a greater perimeter per unit mass around its edge. Any surface tension-driven spreading of the drop itself would therefore be more effective, improving the overall rate of absorption per unit mass. Moreover, relative to smaller droplets, larger droplets are more subject to inertial deposition in the frontal aspects of the airway, whereas finer droplets are more readily travel into the depths of the turbinate region. Furthermore, the imparted particle vector flow provided by the instant dispersion chambers provides for deep penetration/delivery in this region. Finally, given a time-gap between the delivered boli of drops (multiple inhalations), there is sufficient time between breaths for surface absorption and for diffusion into the depths of the lining material, thus reducing or eliminating run off.

When exposed to water, frank mucus 'swells' substantially. For example, if one places an amount of relatively dried up nasal secretion in water, the dried material will substantially swell. Obviously, where such dried material (or partially hydrated material) is distributed over the nasal mucosal surface, it provides a matrix for significant water retention. Where the nasal secretion is less dried out, it would be expected to absorb water at a different rate compared to a drier sample at the same degree of swelling.

According to particular aspects, the thickness of a water layer deposited on the nasal mucosa can be approximated. Given a length of the inner nasal cavity of 8 cm and an overall height of 4 cm, two nasal cavities each having two lateral walls provides for an area of 4×8×2=120 cm². Moreover the convolutions of the turbinates would be expected to double the overall surface area, thus providing an area of about 120 cm for the whole surface of both nasal cavities. If a 2 ml aliquot was distributed uniformly over this surface, it would only be 0.1 mm thick. Where such layer is bound/absorbed to the mucosa beneath, it would not be expected to run-off to any appreciable extent.

According to further aspects, in the case of relatively insoluble drugs, passage of the carrier water into the mucosal substrate would mechanically 'pull' ultrafine drug-bearing particles with it, thereby entrapping them in the matrix, holding them in place even if some of the suspending water was lost (which would be unlikely). According to particular aspects, labeled water and suspended marked drug particles are used to show a slower nasal clearance relative to prior art devices.

Particular aspects of the present invention provide method of nasal delivery of aerosolized particles, comprising: obtaining a subject inspiring through the nose; delivering, over a plurality of nasal inspirations, aerosolized particles of a liquid formulation into at least one nasal passage of the subject, wherein a volume in the range of 0.2 to 2.0 ml, 0.4 to 1.5 ml, 0.6 to 1.2 ml, 0.8 to 1.1 ml, or 0.9 to 1 ml is delivered, wherein the number of inspirations is from about 8 to about 16, and wherein at least about 30%, about 50%, about 60%, about 70%, about 80% about 90% or about 100% of the delivered volume is retained in the at least one nasal passage. In particular embodiments of the method, the average tidal volume ($V_t$) is about 0.7 ml/Kg. Applicants note, as appreciated in the art that the tidal volume is the volume of air inspired into the lungs or expired out of the lungs during one breath, and that the typical resting value is 500 ml (or about 7 ml/kg), increasing dramatically during exercise (e.g., 0.8 to 1.6 L). In certain embodiments, a volume in the range of about 0.4 to 1.5 ml, 0.6 to 1.2 ml, 0.8 to 1.1 ml, or 0.9 to 1 ml is delivered. Applicants note, as appreciated in the art that the 'respiratory minute volume' of an average subject (in a 70 kg adult, at rest) is approximately 6 L/min. In certain embodiments between 1 and 3 ml is delivered, wherein the number of inspirations is from about 16 to about 32, and wherein at least about 30%, about 50%, about 60%, about 70%, about 80% about 90% or about 100% of the delivered volume is retained in the at least one nasal passage.

Systemic Delivery Applications

International application PCT/US2004/029001 (published as WO 2005/023335) is incorporated herein by reference in its entirety.

Current topical drug delivery methods are ineffective at penetrating very far into the nasal cavity and not at all into the paranasal sinuses. Further, systemic delivery via inhalation utilizing the nasal mucosa and mucosa in the paranasal sinuses is desired for many targeted disease states. Preferred aspects of the present invention provide an integrated nebulizer and particle dispersion chamber apparatus that has the ability to deliver the same drugs presently prescribed for many diseases and conditions as very tiny particle doses of medicine via a nasal adapter that allows more efficacious sinus penetration and systemic delivery for the user.

Examples of diseases that can be treated by systemic delivery with the inventive apparatus and methods include, but are not limited to, endocrine and metabolic disorders, migraines, sleep disorders, autoimmune diseases, osteoporosis, neurological diseases and disorders, obesity, sexual dysfunctions, and cardiovascular diseases and episodes.

According to the present invention, the particle sizes, time of application and particle dispersion technology allow the medicine to reach and permeate the nasal cavity and most of the paranasal sinuses. These factors also allow the medicine to enter the user's system via the nasal cavity. All medicines currently applied by direct action to the nasal cavity and paranasal sinuses could be adapted for use with the inventive integrated nebulizer embodiments, including over-thecounter nasal medicines for allergy and colds and flu. Additionally, many medicines currently taken orally, by skin patch, or parenterally could be adapted for use with the inventive integrated nebulizer embodiments.

Significantly, according to the present invention, the integrated nebulizer is used for both topical and systemic delivery of drugs, therapeutics and other beneficial compounds.

For a user with a secondary condition of nasal polyps, the inventive apparatus and methods allow far more effective application of the medicine, which is otherwise blocked or precluded using contemporary systems. Nasal inhalers and spray bottles used to deliver corticosteroids are designed to also slow the re-growth of polyps following their removal. Currently, however, such devices are largely ineffective at accomplishing this, often not slowing polyp growth at all. According to the present invention, the apparatus and methods described herein are significantly more effective in slowing polyp re-growth following their removal.

Many of the side effects of some medicines are eradicated by the inventive devices and methods. With many sprays, for example, the propellant causes a drying of the nasal passages leading to bleeds. With the use of contemporary devices that lead to bleeds, a secondary spray of saline is added to the treatment to try and control the bleeding. Furthermore, steroids in pill form have many unpleasant side effects such as internal bleeding, a redistribution of fluid to the head, neck and back causing unsightly "humps," and easy bruising, to name a few. An effective use of the inventive integrated nebulizer does not have these side effects associated with steroids in pill form.

The inventive integrated nebulizer will allow medicine to be administered to the nasal cavity and paranasal sinuses via very small particles that will penetrate deeply into the nasal cavity, most regions of the paranasal sinuses, and allow for both topical and systemic delivery. The inventive integrated nebulizer will also provide the patient with a more effective absorption of the drug, increasing effectiveness, and will allow multiple conditions to be treated in a far more effective manner.

Typically, since the medicine is delivered in a treatment and not an attack scenario, the application or delivery time is only 0.5-3 minutes, rather than the 10-15 minutes used during an asthma attack. Multiple dose levels of the medicine can be placed in the inventive integrated nebulizer, a week supply for example, and the unit will run for a prescribed time, for example but not limited to three minutes, and will then, in particular embodiments, shut itself off. Preferably, the inventive integrated nebulizer is designed with multiple dose capability and a timer with a pause feature. The pause feature allows the user to stop the treatment under way to deal with a short, minor happenstance and then resume the treatment for the remaining time. The timer is variable to accommodate the drug being administered and/or prescribed by the physician.

In preferred aspects, the nasally delivered nebulized particles are comprised of particles substantially having a mean diameter of about 2 to about 50 μm, about 5 to about 50 μm, about 5 to about 40 μm, about 5 to about 35 μm, about 5 to about 30 μm, about 5 to about 20 μm, about 5 to about 17 μm, about 5 to about 15 μm, about 8 to about 30 μm, about 8 to about 20 μm, about 10 to about 30 μm, about 10 to about 25 μm, about 10 to about 20 μm, about 10 to about 17 μm, about 10 to about 15 μm, about 11 to about 40 μm, about 11 to about 30 μm, about 11 to about 20 μm, about 11 to about 15 μm, about 12 to about 17 μm, about 15 to about 25 μm, about 15 to about 20 μm, and about 17 to about 23 μm.

Preferably, the nasally delivered nebulized particles are comprised of particles substantially having a mean diameter of about 5 to about 30 the delivered nebulized particles are comprises of particles substantially having a mean diameter of about 5 to about 30 μm, about 10 to about 20 μm, about 10 to about 17 μm, about 10 to about 15 μm, and about 12 to about 17 μm.

Preferably, the nasally delivered nebulized particles are comprised of particles substantially having a mean diameter of about 10 to about 15 μm, or about 12 to about 15 μm.

The phrase "substantially having a mean diameter," as used herein with respect to preferred particle diameter ranges, refers to the use of particle collections, wherein at least 50%, at least 60%, at least 70%, at least 80%, at least 90%, at least 95%, or at least 98% have the preferred diameter range. Preferably, at least 60%, at least 70%, at least 80%, at least 90% or at least 95% of the nebulized particles are of the preferred particle diameter range. Preferably, at least 70%, at least 80%, at least 90% or at least 95% of the nebulized particles are of the preferred particle diameter range.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the claimed invention is not limited except as by the appended claims.

The invention claimed is:

1. An aerosol generating and delivery device comprising:
a liquid feed tube having a liquid feed channel with a liquid feed channel exit orifice, an end-wall face and a sidewall, wherein the end wall face between the liquid feed channel exit orifice and a perimeter of the liquid feed tube is substantially normal to a diverting portion of the sidewall of the liquid feed tube; and
a compressed fluid feed channel having a compressed fluid exit orifice, the compressed fluid exit orifice being spaced from the diverting portion of the sidewall, the compressed fluid exit orifice being configured to direct a stream of compressed fluid toward the diverting portion of the sidewall, the diverting portion of the sidewall being configured to disrupt a portion of the stream of compressed fluid, the disrupted portion of the stream of compressed fluid being configured to atomize a liquid from the liquid exit orifice.

2. The device of claim 1, wherein the atomized liquid comprises particles, and the device further comprises a filtering member configured aerodynamically to filter particles from the atomized liquid having a size greater than a predetermined maximum size.

3. The device of claim 1, further comprising a particle dispersion chamber configured to receive the atomized liquid and impart a predetermined flow pattern thereto.

4. The device of claim 3, wherein the predetermined flow pattern is vortical.

5. The device of claim 1, wherein the liquid feed tube comprises a liquid supply member comprising the liquid feed channel, the liquid feed channel having an inlet, a liquid supply member exit orifice, and the end-wall face having an outside diameter disposed about the liquid supply member exit orifice, the liquid supply member feed channel defining a projected longitudinal axis L,
wherein the end wall face liquid feed channel exit orifice is separated by a distance of at least H from the compressed fluid channel exit orifice, H being measured along a projected axis F that is normal to a plane P defined by the compressed fluid channel exit orifice,
H is equal to or greater than ¼ times the inner diameter D1 of the compressed fluid channel adjacent the compressed fluid channel exit orifice,
the projected longitudinal axis L intersects the projected axis F at an angle, defining an intersection plane I, and wherein
at the distance H along projected axis F, the plane I-intersecting portion of the perimeter of the end-wall face is positioned at a distance S in a normal direction from the projected axis F, S being equal to or less than 2 times the inner diameter D1 of the primary compressed fluid channel.

6. The device of claim 1, wherein the liquid comprises at least one selected from the group consisting of medicaments, small or large molecule pharmaceutical agents, liquids, solutions, suspensions, emulsions, perfumes, fragrances, essential oils, cosmeceutical agents, oils, cosmeceutical agents, moisturizing agents, water, lotions, air fresheners, deionizing agents, aromatherapeutic agents, beverages, and skin treatments.

7. The device of claim 1, further comprising a nasal, ocular, oral or vicinity adapter in communication with the atomization means.

8. The device of claim 1, comprising:
a reservoir configured to hold a liquid;
a liquid supply member comprising the liquid feed tube having the sidewall with the diverting portion and comprising the liquid feed channel, the liquid feed channel having an inlet in communication with the reservoir and the liquid feed channel-exit orifice, the liquid feed channel being configured to draw liquid from the reservoir and transport it to the liquid feed channel exit orifice for aerosolization therefrom by a compressed fluid; and
a compressed fluid supply member comprising the compressed fluid feed channel having the compressed fluid exit orifice, the diverting portion being located between the exit orifice of the liquid feed channel and the exit orifice of the compressed fluid feed channel, the compressed fluid feed channel being configured to receive a compressed fluid and conduct a portion of the compressed fluid through the exit orifice and into engagement with the diverting portion of the liquid supply member, the portion of the compressed fluid engaging the diverting portion being diverted by the diverting portion before aerosolizing the liquid from the exit aperture of the feed channel.

9. The device of claim 8, wherein the compressed fluid channel and the diverting portion are configured such that a second portion of the compressed fluid conducted through the compressed fluid exit orifice does not engage the diverting portion of the liquid supply member.

10. The device of claim 8, wherein the diverting portion has a surface, the portion of the compressed fluid engaging the diverting portion engages the surface of the diverting portion, and the surface is configured to divert the portion of the compressed fluid engaging it non-uniformly.

11. The device of claim 8, wherein the liquid supply member comprises a tube section, the liquid feed channel comprises a first portion disposed inside the tube section, the exit aperture of the liquid feed channel is formed in the tube section, and the tube section comprises an outside surface, and the diverting portion comprises a portion of the outside surface of the tube section located between the exit orifice of the feed channel and the exit orifice of the compressed fluid channel.

12. The device of claim 8, wherein the portion of the compressed fluid conducted through the compressed fluid exit orifice exits the orifice along an axis F, the liquid feed channel has a projected longitudinal axis L, and the axis F intersects the axis L.

13. The device of claim 8, wherein the liquid supply member is coupled to the compressed fluid supply member between the inlet of the liquid supply member and the exit orifice of the liquid supply member, the inlet of the liquid supply member being supported within the reservoir.

14. The device of claim 8, further comprises a particle dispersion chamber configured to impart a flow pattern to the aerosolized liquid.

15. The device of claim 8, comprising the liquid feed tube end-wall face having an outside diameter disposed about the liquid feed channel exit orifice, wherein the liquid feed channel defines a projected longitudinal axis L,
the liquid feed tube end wall face and the liquid feed channel exit orifice are separated by a distance of at least H from compressed fluid channel exit orifice, H being measured along a projected axis F that is normal to a plane P defined by the compressed fluid channel exit orifice, H is equal to or greater than ¼ times the inner diameter D1 of the compressed fluid channel adjacent the compressed fluid channel exit orifice, the projected longitudinal axis L intersects the projected axis F at an angle, defining an intersection plane I, and wherein at the distance H along projected axis F, the plane I-intersecting portion of the perimeter of the end-wall face is positioned at a distance S in a normal direction from the projected axis F, S being equal to or less than 2 times the inner diameter D1 of the primary compressed fluid channel.

16. The device of claim 8, wherein the liquid for which the reservoir is configured to hold comprises at least one selected from the group consisting of medicaments, small or large molecule pharmaceutical agents, liquids, solutions, suspensions, emulsions, perfumes, fragrances, essential oils, cosmeceutical agents, oils, cosmeceutical agents, moisturizing agents, water, lotions, air fresheners, deionizing agents, aromatherapeutic agents, beverages, and skin treatments.

17. The device of claim 8, further comprising a nasal, ocular, oral or vicinity adapter in communication with the atomization means.

18. The aerosol generating and delivery device of claim 1, comprising:
   a reservoir configured to hold a liquid;
   a liquid supply member comprising the liquid feed channel comprising:
      a first portion with a first diameter and the liquid feed channel exit orifice, and
      a second portion with a second diameter and an inlet aperture in communication with the reservoir, the first portion diameter being smaller than the second portion diameter, the liquid feed channel being configured to draw liquid from the reservoir into the inlet aperture of the second portion and transport it to the liquid feed channel exit orifice of the first portion for aerosolization therefrom by a compressed fluid; and
   a compressed fluid supply member comprising the compressed fluid feed channel and the compressed fluid channel exit orifice configured to direct a compressed fluid flow passed the exit orifice of the first portion of the liquid feed channel thereby aerosolizing the liquid therefrom.

19. The device of claim 18, wherein the liquid held in the reservoir has a surface, at least a portion of the liquid supply member is located inside the reservoir, a first section of the second portion is below the surface of the liquid, and a second section of the second portion is above the surface of the liquid.

20. The device of claim 18, comprising the liquid feed tube end-wall face having an outside diameter disposed about the liquid supply member orifice, wherein the liquid feed channel first portion defines a projected longitudinal axis L, the liquid feed tube end wall face and the liquid feed channel exit orifice are separated by a distance of at least H from the compressed fluid channel exit orifice, H being measured along a projected axis F that is normal to a plane P defined by the compressed fluid channel exit orifice, H is equal to or greater than ¼ times the inner diameter D1 of the compressed fluid channel adjacent the compressed fluid channel exit orifice, the projected longitudinal axis L intersects the projected axis F at an angle defining an intersection plane I, and wherein at the distance H along projected axis F, the plane I-intersecting portion of the perimeter of the liquid feed tube end-wall face is positioned at a distance S in a normal direction from the projected axis F, S being equal to or less than 2 times the inner diameter D1 of the primary compressed fluid channel.

21. The device of claim 18, wherein the liquid for which the reservoir is configured to hold comprises at least one selected from the group consisting of medicaments, small or large molecule pharmaceutical agents, liquids, solutions, suspensions, perfume, fragrance, essential oil or cosmeceutical agents, oils, cosmeceutical agents, moisturizing agents, water, lotions, air fresheners, deionizing agents and skin surface treatments.

22. The device of claim 18, further comprising a nasal, ocular, oral or vicinity adapter.

23. The aerosol generating and delivery device of claim 1, comprising:
   a housing having a wall defining an atomization chamber in which a liquid or solution is atomizable, and comprising holding means suitable for holding a liquid or solution to be atomized; and
   atomization means comprising a primary compressed fluid feed channel having a length and inner diameter, and the compressed fluid exit orifice at a first end thereof in fluid communication with the atomization chamber and defining a primary compressed fluid exit orifice plane P, the compressed fluid feed channel at a second end in fluid communication with a compressed fluid source and defining a projectable compressed fluid feed channel axis F, the atomization means further comprising a primary liquid feed channel having a length, inner diameter and liquid feed channel wall, and at a first primary liquid feed channel end having the liquid feed channel end-wall face having an outside diameter disposed about the liquid feed channel orifice in fluid communication with the atomization chamber, the primary liquid feed channel at a second end in communication with the liquid holding means, the primary liquid feed channel defining a projectable longitudinal liquid feed channel axis L, wherein
   the liquid feed channel end wall face and the liquid feed channel orifice are separated by a distance of at least H from the primary orifice plane P, H being measured along the projected axis F and H being equal to or greater than ¼ times the inner diameter D1 of the primary compressed fluid feed channel, wherein
   the projected longitudinal axis L intersects the projected longitudinal axis F at an angle, defining an intersection plane I, and wherein
   at the distance H along projected longitudinal axis F, the plane I-intersecting portion of the perimeter of the liquid feed channel end-wall face is positioned at a distance S in a normal direction from the projected longitudinal axis F, S being equal to or less than 2 times the inner diameter D1 of the primary compressed fluid feed channel.

24. The aerosol generating and delivery device of claim 23, further comprising a particle filter member in fluid communication with the particle atomization means, the particle filter member having a surface contour and positioned at a distance of at least J along the projected axis F from the primary orifice plane P to provide an aerodynamic fluid flow around the surface, and wherein the distance J is greater than the distance H.

25. The aerosol generating and delivery device of claim 24, wherein the distance J along the projected axis F from the primary orifice plane P is equal to or greater than 2 times D1.

26. The aerosol generating and delivery device of claim 24, wherein the configuration and positioning of the filter member along the projected axis F operationally provides, depending on particle size and/or mass, for a proportion of atomized particles that collide with the member and a proportion of non-colliding particles with velocity vectors that avoid the surface and/or are carried in the aerodynamic fluid flow around the surface.

27. The aerosol generating and delivery device of claim 24, wherein the particle filter member is held at the distance J along the projected axis F by at least one filter support member communicating with the wall of the atomization chamber, the support member configured to operatively direct liquid accumulating on the filter away from the filter member for return to the liquid holding means.

28. The aerosol generating and delivery device of claim 23, further comprising a secondary liquid feed channel having a length and an inner diameter D4, and communicating between the second end of the primary liquid feed channel and the liquid holding means, wherein the inner diameter D4 is larger than the inner diameter D2 of the primary liquid feed channel.

29. The aerosol generating and delivery device of claim 28, wherein D4 is equal to or greater than 2 times D2.

30. The aerosol generating and delivery device of claim 28, wherein D4 is from about 1 mm to about 5 mm.

31. The aerosol generating and delivery device of claim 23, wherein the distance S from projected axis F is less than or equal to ½ times D1.

32. The aerosol generating and delivery device of claim 23, wherein the selected distance S is such that there is overlap of axis F with the plane I-intersecting portion of the perimeter of the liquid feed channel end wall face, wherein overlap is defined as being present if the projected axis F intersects the liquid feed channel end wall face or the liquid feed channel orifice thereof.

33. The aerosol generating and delivery device of claim 32, wherein the distance S from projected axis F is less than or equal to ½ times D1.

34. The aerosol generating and delivery device of claim 23, wherein H is less than D1.

35. The aerosol generating and delivery device of claim 34, wherein H is equal to or greater than D1.

36. The aerosol generating and delivery device of claim 23, wherein H is less than D2.

37. The aerosol generating and delivery device of claim 36, wherein H is equal to or greater than D2.

38. The aerosol generating and delivery device of claim 23, wherein H is equal to, or greater than D3.

39. The aerosol generating and delivery device of claim 38, wherein H is less than D3.

40. The aerosol generating and delivery device of claim 23, wherein H is less than D3, and greater than at least one of D1 and D2.

41. The aerosol generating and delivery device of claim 23, wherein H is greater than any one of D1, D2 or D3.

42. The aerosol generating and delivery device of claim 23, wherein D2 is equal to or greater than D1.

43. The aerosol generating and delivery device of claim 23, further comprising a particle dispersion chamber having a chamber wall and having an input opening and an output opening with an internal channel therebetween, the input opening in fluid communication with the atomization chamber, the dispersion chamber having at least one directed fluid output operative to impart a fluid flow pattern to aerosolized particles within and exiting the dispersion chamber output opening.

44. The aerosol generating and delivery device of claim 43, wherein the imparted fluid flow pattern is vortical flow, turbulent flow or randomized flow.

45. The aerosol generating and delivery device of claim 43, wherein the at least one directed fluid output comprises an ambient air channel that at one end is in communication with ambient air, and having at the other end an ambient air channel orifice in communication with the internal channel.

46. The aerosol generating and delivery device of claim 45, further comprising an outer housing having an outer housing wall defining a plenum space between the outer housing wall and the wall of the particle dispersion chamber, the outer housing wall comprising at least one ambient air input opening in communication with ambient air, such that the ambient air channel and corresponding ambient air channel orifice communicate with the at least one ambient air input opening by means of the plenum space.

47. The aerosol generating and delivery device of claim 46, further comprising a one-way valve in operative association with the at least one opening of the outer housing wall.

48. The aerosol generating and delivery device of claim 43 wherein the at least one directed fluid output comprises a compressed fluid output channel that at one end is in communication with a source of compressed fluid, and having at the other end a compressed fluid outlet orifice in communication with the internal channel of the particle dispersion chamber.

49. The aerosol generating and delivery device of claim 48, additionally comprising: a secondary compressed fluid channel intermediate between the primary compressed fluid feed channel and a source of compressed fluid; and a particle dispersion chamber feed channel communicating between the secondary compressed fluid channel and the at least one directed compressed fluid outlets and corresponding orifices.

50. The aerosol generating and delivery device of claim 43, comprising a plurality of directed fluid outputs, the plurality comprising at least one ambient air channel that at one end is in communication with ambient air, and having at the other end an ambient air channel orifice in communication with the internal channel of the particle dispersion chamber, the plurality further comprising at least one compressed fluid output channel that at one end is in communication with a source of compressed fluid, and having at the other end a compressed fluid channel outlet orifice in communication with the internal channel of the particle dispersion chamber.

51. The aerosol generating and delivery device of claim 50, further comprising an outer housing having an outer housing wall defining a plenum space between said outer housing wall and the wall of the particle dispersion chamber, the outer housing wall comprising at least one ambient air opening in communication with ambient air, such that the ambient air channel and corresponding ambient air channel orifice communicate with the at least one ambient air opening by means of the plenum space.

52. The aerosol generating and delivery device of claim 51, further comprising a one-way valve in operative association with the at least one opening of the outer housing wall.

53. The aerosol generating and delivery device of claim 43, additionally comprising: a secondary compressed fluid channel intermediate between the primary compressed fluid feed channel and a source of compressed fluid; and a particle dispersion chamber feed channel communicating between the secondary compressed fluid channel and the at least one directed compressed fluid outlets and corresponding orifices.

54. The aerosol generating and delivery device of claim 43, further comprising a nasal adapter in fluid communication with the output opening of the particle dispersion chamber.

55. The aerosol generating and delivery device of claim 54, wherein the nasal adapter comprises at least one oriented opening, configured to channel particles into a sub-region of the nasal apertures to more selectively target particle delivery within the nasal cavity, and regions thereof, of a user.

56. The aerosol generating and delivery device of claim 43, further comprising an ocular adapter in fluid communication with the output opening of the particle dispersion chamber.

57. The aerosol generating and delivery device of claim 43, comprising:
a housing having a wall defining an atomization chamber in which a liquid or solution is atomizable, and comprising holding means suitable for holding a liquid or solution to be atomized;
atomization means comprising a primary compressed fluid feed channel having a length and inner diameter, and the compressed fluid exit orifice at a first end thereof in fluid communication with the atomization chamber and defining a primary compressed fluid orifice plane P, the primary compressed fluid feed channel at a second end in fluid communication with a compressed fluid source and defining a projectable compressed fluid feed channel axis F, the atomization means further comprising a primary liquid feed channel having a length, inner diameter and primary liquid feed channel wall, and at a first primary liquid feed channel end having the liquid feed channel end-wall face having an outside diameter disposed about the liquid feed channel orifice in fluid communication with the atomization chamber, the primary liquid feed channel at a second end in communication with the liquid holding means, the primary liquid feed channel defining a projectable longitudinal liquid feed channel axis L; and
a particle filter member in fluid communication with the particle atomization means, the filter member positioned at a distance J, greater than or equal to 10 times the inner diameter D1 of the primary compressed fluid feed channel, along the projected axis F from the primary orifice plane P, wherein
the projected longitudinal axis L intersects the projected longitudinal axis F at an acute or obtuse angle, defining an intersection plane I, wherein
the liquid feed channel end wall face and the liquid feed channel orifice are separated by a distance of at least H from the primary orifice plane P, H being measured along the projected axis F and H being equal to or greater than ¼ times D1, and wherein
at the distance H along projected longitudinal axis F, a plane I-intersecting portion of the perimeter of the end-wall face is positioned at a distance S in a normal direction from the projected longitudinal axis F, S being equal to or less than 2 times D1.

58. The aerosol generating and delivery device of claim 57, wherein the projected longitudinal axis L intersects the projected longitudinal axis F at an acute angle.

59. The aerosol generating and delivery device of claim 57, further comprising a particle dispersion chamber having a chamber wall and having an input opening and an output opening with an internal channel therebetween, the input opening in fluid communication with the atomization chamber, the dispersion chamber having at least one directed fluid output operative to impart a fluid flow pattern to aerosolized particles within and exiting the dispersion chamber output opening.

60. The aerosol generating and delivery device of claim 1, comprising:
a housing having a wall defining an atomization chamber in which a liquid or solution is atomizable, and comprising holding means suitable for holding a liquid or solution to be atomized;
atomization means comprising a primary compressed fluid feed channel having a length and inner diameter, and the compressed fluid exit orifice at a first end thereof in fluid communication with the atomization chamber and defining a primary compressed fluid orifice plane P, the primary compressed fluid feed channel at a second end in fluid communication with a compressed fluid source and defining a projectable primary compressed fluid feed channel axis F, the atomization means further comprising a primary liquid feed channel having a length, inner diameter and channel wall, and at a first channel end having the liquid feed channel end-wall face having an outside diameter disposed about the liquid feed channel orifice in fluid communication with the atomization chamber, the primary liquid feed channel at a second end in communication with the liquid holding means, the primary liquid feed channel defining a projectable longitudinal liquid feed channel axis L; and
a secondary liquid feed channel having a length and an inner diameter D4, and communicating between the second end of the primary liquid feed channel and the liquid holding means, wherein the inner diameter D4 is equal to or greater than 5 times the inner diameter D2 of the primary liquid feed channel, wherein
the projected longitudinal axis L intersects the projected longitudinal axis F at an acute or obtuse angle, defining an intersection plane I, wherein
the liquid feed channel end wall face and the liquid feed channel exit orifice are separated by a distance of at least H from the primary orifice plane P, H being measured along the projected axis F and H being equal to or greater than ¼ times D1, and wherein
at the distance H along projected longitudinal axis F, a plane I-intersecting portion of the perimeter of the liquid feed channel end-wall face is positioned at a distance S in a normal direction from the projected longitudinal axis F, S being equal to or less than 2 times the inner diameter D1 of the primary compressed fluid feed channel.

61. The aerosol generating and delivery device of claim 60, wherein the projected longitudinal axis L intersects the projected longitudinal axis F at an acute angle.

62. The aerosol generating and delivery device of claim 60, further comprising a particle dispersion chamber having a chamber wall and having an input opening and an output opening with an internal channel therebetween, the input opening in fluid communication with the atomization chamber, the dispersion chamber having at least one directed fluid output operative to impart a fluid flow pattern to aerosolized particles within and exiting the dispersion chamber output opening.

* * * * *